United States Patent
Alauddin et al.

(10) Patent No.: US 10,463,453 B2
(45) Date of Patent: Nov. 5, 2019

(54) ORTHODONTIC APPLIANCES AND METHODS OF MAKING AND USING SAME

(71) Applicant: Ormco Corporation, Orange, CA (US)

(72) Inventors: Sammel Shahrier Alauddin, Rancho Cucamonga, CA (US); Jason Anthony Mohr, Fontana, CA (US); Benjamin Mark Nazeck, San Dimas, CA (US); Nathan Wong, San Dimas, CA (US)

(73) Assignee: Ormco Corporation, Orange, CA (US)

( * ) Notice: Subject to any disclaimer, the term of this patent is extended or adjusted under 35 U.S.C. 154(b) by 327 days.

(21) Appl. No.: 14/478,271

(22) Filed: Sep. 5, 2014

(65) Prior Publication Data

US 2015/0072299 A1    Mar. 12, 2015

Related U.S. Application Data

(60) Provisional application No. 61/874,571, filed on Sep. 6, 2013.

(51) Int. Cl.
*A61C 7/14* (2006.01)
*A61C 7/20* (2006.01)
(Continued)

(52) U.S. Cl.
CPC ............... *A61C 7/20* (2013.01); *A61C 7/141* (2013.01); *A61C 7/18* (2013.01); *A61C 7/22* (2013.01);
(Continued)

(58) Field of Classification Search
CPC .... A61C 7/18; A61C 7/20; A61C 7/22; A61C 7/28; A61C 7/30; A61C 7/141;
(Continued)

(56) References Cited

U.S. PATENT DOCUMENTS

| 4,177,372 A | 12/1979 | Kotera et al. |
| 5,092,941 A | 3/1992 | Miura |

(Continued)

FOREIGN PATENT DOCUMENTS

| EP | 1930480 A1 | 6/2008 |
| JP | 2009522057 A | 6/2009 |

(Continued)

OTHER PUBLICATIONS

International Searching Authority, International Search Report and Written Opinion in International Application No. PCT/US2014/054295, dated Dec. 24, 2014.

(Continued)

*Primary Examiner* — Wade Miles
*Assistant Examiner* — Matthew P Saunders
(74) *Attorney, Agent, or Firm* — Wood Herron & Evans LLP

(57) ABSTRACT

An orthodontic appliance includes a portion made of a shape memory alloy having a base alloy composition of at least two different metallic elements and a treated region having an alloy composition that is depleted in at least one of the metallic elements. The base alloy may include a nickel titanium alloy (NiTi), a copper chromium nickel titanium alloy (CuCrNiTi), or a copper aluminum nickel (CuAlNi) alloy. The treated region may be depleted in at least one of copper, aluminum, nickel, and titanium relative to the base alloy composition by exposing the base alloy to a source of energy. The base alloy composition has a first austenitic finish temperature and the treated region has an austenitic finish temperature that may be different than the first austenitic finish temperature. The treated region may form a part of an archwire, a stop, a hook, a crown, a band, or an orthodontic bracket.

17 Claims, 43 Drawing Sheets

(51) Int. Cl.
  *C22C 19/00* (2006.01)
  *A61C 7/18* (2006.01)
  *C22C 30/02* (2006.01)
  *A61C 7/22* (2006.01)
  *A61C 7/28* (2006.01)
  *C22C 19/03* (2006.01)
  *C22C 30/00* (2006.01)
  *A61C 7/30* (2006.01)
  *A61B 17/00* (2006.01)

(52) U.S. Cl.
  CPC .............. *A61C 7/28* (2013.01); *C22C 19/007* (2013.01); *C22C 19/03* (2013.01); *C22C 30/00* (2013.01); *C22C 30/02* (2013.01); *A61B 2017/00526* (2013.01); *A61B 2017/00867* (2013.01); *A61C 7/30* (2013.01); *A61C 2201/007* (2013.01)

(58) Field of Classification Search
  CPC ... A61C 2201/007; C22C 30/00; C22C 30/02; C22C 19/03; C22C 19/007
  USPC .......................................................... 433/20
  See application file for complete search history.

(56) References Cited

U.S. PATENT DOCUMENTS

| | | | |
|---|---|---|---|
| 5,683,245 A * | 11/1997 | Sachdeva | A61C 7/20 433/20 |
| 5,728,240 A | 3/1998 | Yamamoto et al. | |
| 6,548,013 B2 * | 4/2003 | Kadavy | B22F 3/22 419/28 |
| 6,554,612 B2 | 4/2003 | Georgakis et al. | |
| 6,582,226 B2 | 6/2003 | Jordan et al. | |
| 6,663,385 B2 | 12/2003 | Tepper | |
| 6,669,794 B1 | 12/2003 | Bellouard et al. | |
| 7,192,496 B2 * | 3/2007 | Wojcik | C22C 19/007 148/669 |
| 7,267,545 B2 | 9/2007 | Oda | |
| 7,677,887 B2 | 3/2010 | Nicholson | |
| 8,414,292 B2 | 4/2013 | Lopes | |
| 2006/0003282 A1 | 1/2006 | Nicholson | |
| 2007/0137740 A1 * | 6/2007 | Johnson | A61L 31/022 148/562 |
| 2007/0154859 A1 | 7/2007 | Hilliard | |
| 2007/0178422 A1 | 8/2007 | Voudouris | |
| 2009/0187243 A1 * | 7/2009 | Johnson | A61L 27/047 623/11.11 |
| 2011/0114230 A1 * | 5/2011 | Syed | C22C 14/00 148/563 |
| 2011/0189624 A1 | 8/2011 | Wong | |
| 2012/0048432 A1 * | 3/2012 | Johnson | A61C 7/20 148/563 |
| 2012/0148974 A1 | 6/2012 | Chester | |
| 2012/0192999 A1 * | 8/2012 | Khan | B23K 26/0006 148/402 |
| 2015/0044084 A1 * | 2/2015 | Hofmann | B32B 15/01 419/7 |
| 2016/0008043 A1 | 1/2016 | Bonutti et al. | |
| 2016/0287354 A1 | 10/2016 | Viecilli et al. | |
| 2017/0224444 A1 | 8/2017 | Viecilli et al. | |

FOREIGN PATENT DOCUMENTS

| | | |
|---|---|---|
| WO | 2007018189 A1 | 2/2007 |
| WO | 2007081708 A2 | 7/2007 |
| WO | 2013/115831 A1 | 8/2013 |

OTHER PUBLICATIONS

The International Bureau of WIPO, International Preliminary Report on Patentability issued in International Application No. PCT/US2014/054295 dated Mar. 8, 2016.

Extended European Search Report conducted by Reddie & Grose LLP.

Material World Magazine, "Multiple Memories for Shape Memory Alloys," Oct. 8, 2010.

Japanese Patent Office, Office Action in corresponding Japanese Patent Application No. 2016-540421 dated Jun. 18, 2018.

* cited by examiner

ORTHODONTIC APPLIANCES AND METHODS OF MAKING AND USING SAME

CROSS REFERENCE TO RELATED APPLICATIONS

This application claims priority to U.S. Provisional Patent Application Ser. No. 61/874,571, filed Sep. 6, 2013, the disclosure of which is incorporated by reference herein in its entirety.

TECHNICAL FIELD

The invention relates generally to orthodontic appliances and, more particularly, to metallic orthodontic appliances and methods for making and using them.

BACKGROUND

Orthodontic treatment often involves attaching an appliance to the tooth or attaching one appliance to another orthodontic appliance previously attached to the tooth. Forces applied to the appliance(s) are then transferred to, and thus move, the tooth. As such, orthodontic appliances represent a principal component of corrective orthodontic treatment devoted to improving a patient's dentition. Orthodontic appliances may include brackets, archwires, hooks, bands, and other devices.

Using the orthodontic bracket as an example, an orthodontist may affix orthodontic brackets to the patient's teeth with an adhesive and then engage an archwire into a slot of each bracket. The archwire exerts flexural and/or torsional stresses on the orthodontic brackets to create restorative forces, including rotation, tipping, extrusion, intrusion, translation, and/or torque forces, tending to bring the teeth toward a desired, aesthetic position. Traditional ligatures, such as small elastomeric O-rings or fine metal wires, may be employed to retain the archwire within each bracket slot. Due to difficulties encountered in applying an individual ligature to each bracket, self-ligating orthodontic brackets have been developed that eliminate the need for ligatures by relying on a movable portion or member, such as a latch, clip, or slide, for retaining the archwire within the bracket slot.

In a typical sequence of orthodontic treatment, a small diameter round metallic archwire is used for preliminary tooth movement, followed by the use of rectangular metallic archwires at the later stages of treatment. The final stage may involve the use of an archwire of rectangular cross-section which fills the slot in the bracket. For example, a small (e.g., 0.014 inch diameter) round archwire may be used initially and a rectangular cross-sectioned (e.g., 0.021 inch by 0.025 inch) archwire may be introduced when torque is required to precisely orient the teeth, usually at or near the end of treatment. Since its rectangular shape renders it non-rotatable with respect to each bracket, the archwire imposes torquing or uprighting forces on the teeth. As a result, the rectangular wire may be slightly twisted between adjacent teeth. Other archwires of different sizes may be introduced during intermediate stages of treatment.

Where malocclusion is severe, it is generally not practical to commence treatment with large cross-sectional archwires for several reasons. Most significantly, the bracket slots are generally not in alignment with each other so that the archwire must be substantially twisted or deflected at the commencement of treatment. Since large cross-sectioned archwires undergo permanent deformation more easily than smaller wires, initial twisting or deflection may render them nearly useless at the beginning of treatment. Large wires may also exert unpredictably large forces during the initial phase of treatment, which may be extremely painful for the patient. For at least this reason, it is often necessary to use smaller archwires initially and then replace the small archwires with larger cross-sectional archwires as treatment progresses. For the patient, this means frequent appointments and significant time spent in "the chair." For the clinician, this means increased costs and reduced treatment capacity.

Early stage wires are typically made of shape memory alloys (SMAs) with superelastic properties. SMAs undergo a reversible crystalline phase transformation from a martensitic phase to an austenitic phase when heated through a particular temperature range. Generally, martensite is soft and ductile while austenite is rigid and elastic. Because these two phases provide individually unique mechanical properties, the temperature of the alloy during use dictates the mechanical properties of the alloy according to the proportions of martensite and austenite. Therefore, the phases present when an orthodontic appliance is used at the temperature of the human body will determine the mechanical properties of the appliance.

In this regard, the temperature at which the martensite-to-austenite phase change starts is generally denoted as $A_s$, referred to as the "austenitic start temperature," and the temperature at which the phase changes finishes upon heating is denoted as $A_f$, referred to as the "austenitic finish temperature." Above $A_f$, the stable phase in the alloy is the austenitic phase. During cooling, the temperature at which the phase change from austenite to martensite starts is denoted as $M_s$, referred to as the "martensitic start temperature," and the temperature at which the phase change finishes is denoted as $M_f$, referred to as the "martensitic finish temperature." The reversible phase transformation permits SMAs to be deformed at one temperature and then heated to an elevated temperature where the SMA recovers all or nearly all of its predeformed or original shape. NiTi-based alloys are well-known shape memory alloys and are alloys of nickel (Ni) and titanium (Ti). For example, one type of NiTi-based alloy is nitinol, which is an alloy of approximately 50/50 nickel to titanium.

In addition, SMAs often exhibit superelastic characteristics. Superelasticity results from stress-induced phase transformation of austenite to martensite at or slightly above $A_f$. Reversion to austenite occurs as the strain is reduced or removed. The stress-strain behavior of superelastic materials used in orthodontics takes full advantage of this phase change and often allows recovery of up to 6% strain, well beyond conventional stainless steels.

Current manufacturing technology focuses on a pre-defined process that controls the composition of the alloy, the thermal treatment of the alloy, and the stresses induced into the alloy during manufacturing of the orthodontic appliance. Collectively these parameters establish the transformation properties, i.e., the shape of the transformation curve defined by the temperatures $A_s$, $M_s$, $A_f$ and $M_f$ of the SMA.

While orthodontic appliances have been generally successful, manufacturers of orthodontic appliances continually strive to improve the performance of their appliances. In this regard, there remains a need for superelastic and/or shape memory orthodontic appliances that provide improved performance during orthodontic treatment.

SUMMARY OF THE INVENTION

The present invention overcomes the foregoing and other shortcomings and drawbacks of orthodontic brackets. While the present invention will be described in connection with certain embodiments, it will be understood that the present invention is not limited to these embodiments. On the contrary, the present invention includes all alternatives, modifications and equivalents as may be included within the spirit and scope of the present invention.

In accordance with the principles of the present invention, an orthodontic appliance comprises a portion made of a shape memory alloy having a base alloy composition of at least two metallic elements and a treated region having an alloy composition that is depleted in at least one of the metallic elements of the base alloy composition.

In one embodiment, the shape memory alloy is a nickel titanium alloy (NiTi) and the alloy composition of the treated region is depleted in nickel relative to the base alloy composition.

In one embodiment, the shape memory alloy is a copper chromium nickel titanium alloy (CuCrNiTi) and the alloy composition of the treated region is depleted in one of copper, nickel, and titanium relative to the base alloy composition.

In one embodiment, the shape memory alloy is a copper aluminum nickel alloy (CuAlNi) and the alloy composition of the treated region is depleted in at least aluminum relative to the base alloy composition.

In one embodiment, the shape memory alloy is a copper aluminum nickel alloy (CuAlNi) and the alloy composition of the treated region is depleted in at least copper relative to the base alloy composition.

In one embodiment, the base alloy composition has a first austenitic finish temperature and the treated region has an austenitic finish temperature that is greater than the first austenitic finish temperature.

In one embodiment, the portion forms a part of an archwire, a stop, a hook, a crown, a band, or an orthodontic bracket.

In one embodiment, the orthodontic application is an archwire having a length as measured from one end to another end and wherein the portion includes a first zone along the length of the archwire.

In one embodiment, the archwire includes an untreated region that forms a second zone, the untreated region having the base alloy composition and the second zone being adjacent the first zone.

According to one aspect of the present invention, there is orthodontic appliance for placement on a tooth. The orthodontic appliance comprises a body made of a shape memory alloy having a base alloy composition of at least two metallic elements. The body includes a sidewall having an apical margin that defines an opening for receiving the tooth. The sidewall further includes a treated region that is depleted in at least one of the metallic elements of the base alloy composition.

In one embodiment, the body further comprises an inner surface configured to contact the tooth and the inner surface includes the treated region.

In one embodiment, the treated region of the inner surface has a greater ductility than an untreated region of the body at temperatures at or near the temperature of the human body.

In one embodiment, the treated region of the inner surface is configured to plastically deform when compressed against the tooth.

In one embodiment, the body is configured to remain in a position relative to the tooth without an adhesive.

In one embodiment, at least one cross-sectional dimension of the body is larger than a cross-sectional dimension of the tooth prior to being subjected to an oral temperature.

In one embodiment, the body has an annular cross sectional shape.

In one embodiment, the body is configured to transition from a deformed, enlarged state to a contracted state when heated to an operating temperature.

According to another aspect of the present invention, there is an orthodontic appliance for placement on an orthodontic archwire. The orthodontic appliance comprises a C-shaped body made of a shape memory alloy having a base alloy composition of at least two metallic elements. The C-shaped body is configured to engage the archwire. The C-shaped body comprises first and second opposing portions that define an opening therebetween. A third portion extends between the first and second portions and opposes the opening. A treated region forms a portion of at least one of the first, second, and third portions. The treated region is depleted in at least one of the metallic elements of the base alloy composition.

In one embodiment, the body is configured to transition between an opened position and a closed position when heated and the body is configured to engage the archwire in the closed position.

In one embodiment, the body is configured to transition between the opened and closed positions without mechanical input during heating.

In one embodiment, the treated region is exposed along an inner surface of at least one of the first portion, the second portion, or the third portion.

In one embodiment, the inner surface of at least one of the first portion, the second portion, or the third portion includes at least one rib that is configured to plastically deform when the rib contacts the archwire.

In one embodiment, the at least one rib is parallel to a peripheral edge of the body.

In one embodiment, the at least one rib is transverse to a peripheral edge of the body.

According to another aspect of the present invention, an orthodontic bracket for coupling an archwire with a tooth comprises a bracket body made of a shape memory alloy having a base alloy composition of at least two metallic elements. The bracket body includes an archwire slot that is configured to receive the archwire therein and a treated region that forms at least a portion of the bracket body. The treated region is depleted in at least one of the metallic elements of the base alloy composition.

In one embodiment, the bracket body further comprises an integral ligating member having an opened position in which the archwire is insertable into the archwire slot and a closed position in which the integral ligating member is configured to prevent removal of the archwire from the archwire slot. The orthodontic bracket is a self-ligating orthodontic bracket, wherein the integral ligating member includes the treated region.

In one embodiment, the treated region is configured to exhibit superelastic properties during orthodontic treatment.

In one embodiment, the orthodontic bracket includes untreated regions that do not exhibit superelastic properties during orthodontic treatment.

In one embodiment, the treated region has shape memory properties in a temperature range below the normal operating temperature of the oral cavity.

In one embodiment, the bracket body further includes a mesial portion and a distal portion separated by a central portion, each of the mesial portion, the distal portion, and the central portion define the archwire slot. The central portion includes the integral ligating member.

In one embodiment, the bracket body further includes a gingival body portion and an occlusal body portion that are separated by the archwire slot. The integral ligating member extends from only one of the gingival body portion or occlusal body portion.

In one embodiment, the integral ligating member is in the form of an integral ligating clip having a first portion that extends over the archwire slot in the closed position, a second portion at which the integral ligating clip is formed with the bracket body, and a third portion between the first and the second portion, at least the second portion includes the treated region.

In one embodiment, the bracket body further comprises a plurality of tie wings extending from the bracket body. At least part of the treated region is disposed on at least one of the tie wings.

In one embodiment, the bracket body includes a plurality of the treated regions. Each region has a different alloy compositions and from the base alloy composition. The plurality of treated regions is configured to absorb the shock from impact on the bracket body.

In one embodiment, each of the plurality of treated regions differ in the proportion of martensite to austenite present at the temperature of the oral cavity and, in one or more of the treated regions, the austenite transforms to martensite when subject to an impact on the bracket body.

According to another aspect of the present invention, a method of manufacturing an orthodontic appliance comprises exposing the orthodontic appliance made of a shape memory alloy having a base alloy composition of at least two metallic elements to a source of energy. The method further includes treating a surface of the orthodontic appliance with the source of energy to remove at least one of the metallic elements from a region including the surface to form a treated region being depleted in at least one metallic element relative to the base alloy composition.

In one embodiment, exposing the orthodontic appliance includes exposing one of a group consisting of an archwire, a stop, a hook, a band, a crown, and an orthodontic bracket to the source of energy.

According to another aspect of the present invention, a method of using an orthodontic appliance made of a shape memory alloy having a base alloy composition of at least two metallic elements and including a treated region having a composition that is depleted in at least one metallic element from the base alloy composition comprises storing the orthodontic appliance at a temperature that is different than the normal temperature of the oral cavity. The method further includes installing the orthodontic appliance into a patient's mouth whereby the phase composition of the treated region differs from the phase composition of the base alloy composition.

In one embodiment, storing further includes storing at a temperature that is less than the normal temperature of the oral cavity.

In one embodiment, after installing and during treatment, the method further comprises reducing the temperature of the orthodontic appliance to increase the proportion of martensite relative to austenite and then plastically deforming the appliance including a portion of the cooled treated region.

In one embodiment, the orthodontic appliance is a band or the crown and installing the band or the crown on a tooth plastically deforms the treated region and the installation is free of an adhesive between the band or the crown and the tooth.

BRIEF DESCRIPTION OF THE DRAWINGS

The accompanying drawings, which are incorporated in and constitute a part of this specification, illustrate embodiments of the invention and with the general description given above, together with the detailed description given below, serve to explain the invention.

DETAILED DESCRIPTION

Archwires

Archwires of shape memory alloys (SMAs) that exhibit superelastic properties are available for use in orthodontic treatment. Currently, archwire manufacturers target specific austenitic finish temperatures, $A_f$, depending upon the desired force to be exerted upon all of the teeth of the patient's dental arch during use. By reducing $A_f$, the wire exhibits greater stiffness and elasticity during use. By increasing $A_f$, the wire becomes softer and more ductile. Therefore, by targeting a desired $A_f$, the archwire will provide a targeted, known loading performance on all of the teeth during treatment.

In addition to archwires having generally uniformly formed properties along their lengths, archwires having variations in properties along their lengths have been developed to target different regions or zones of the patient's dental arch with different corrective forces. To that end, in an effort to provide an archwire with variations in mechanical properties, such as within different zones or sections having different elasticities, some manufacturers have joined individual sections of wire together with each section having a different austenitic finish temperature. Other manufacturers have developed localized heat treatment methods to generate a difference in $A_f$ along the length of the archwire or alternatively have manufactured archwires with different cross-sectional configurations along the length of the archwire. Yet another technique utilized to address variations in the teeth in the patient's dental arch includes locally bending the archwire so that it provides a unique corrective force to a specific tooth according to that tooth's required reorientation. Each of these techniques, while providing variation in mechanical properties along the length of the archwire, is process intensive and, as a consequence, generally not cost-effective.

Figure 1:
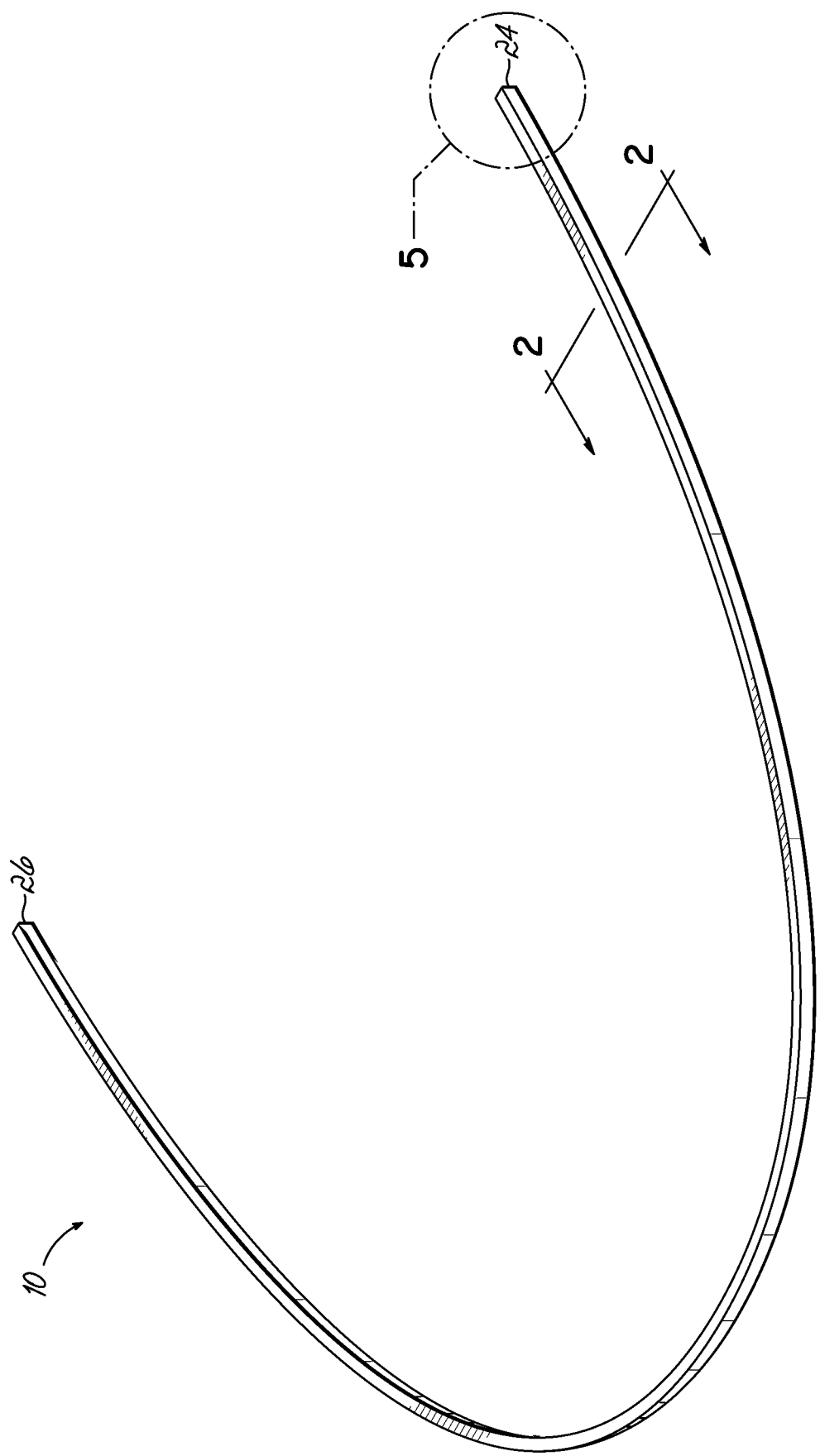
FIG. 1 is a perspective view of an orthodontic archwire according to one embodiment of the invention.
Figure 2:
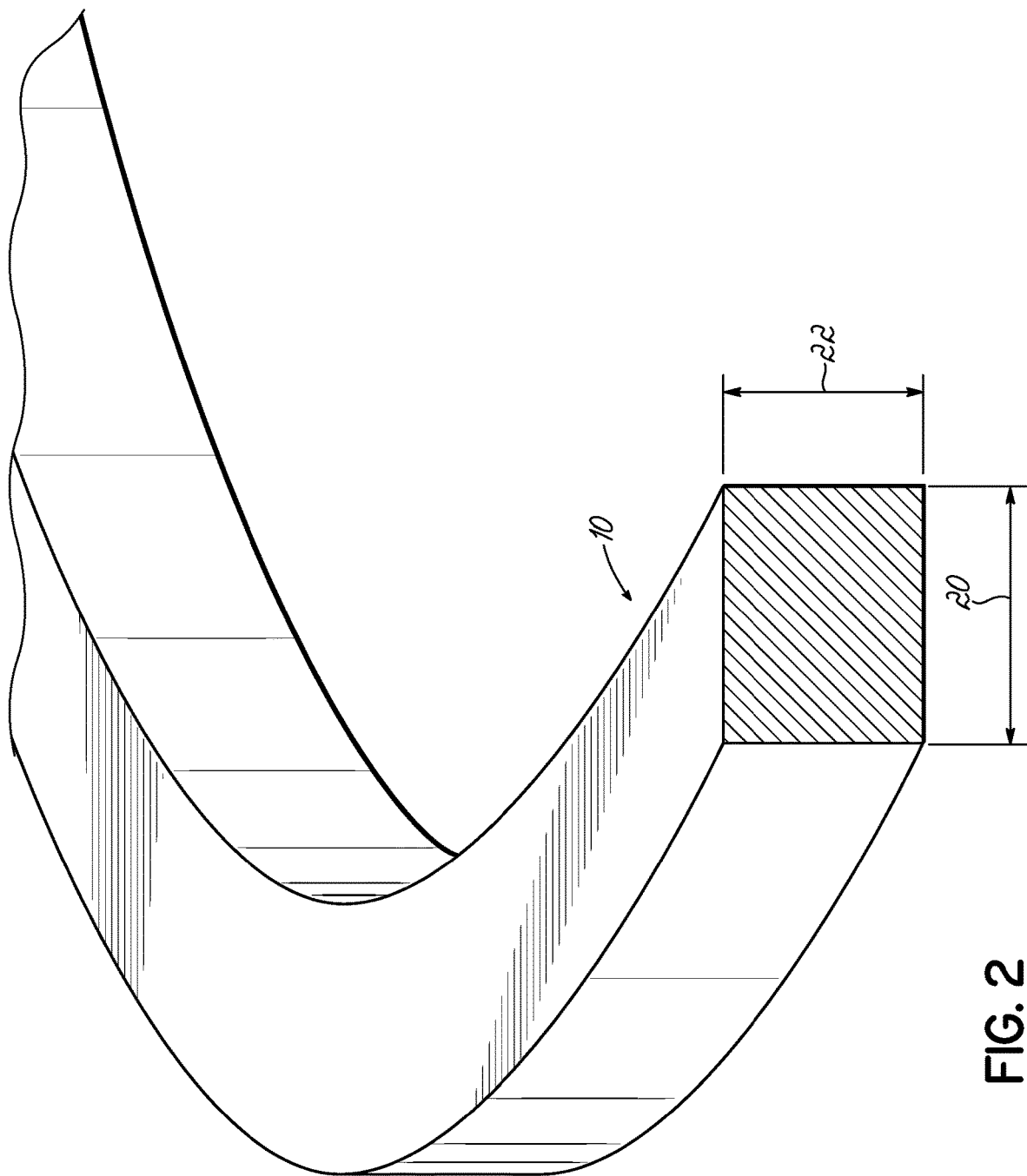
FIG. 2 is a cross-sectional perspective view of the orthodontic appliance of FIG. 1 taken along section line 2-2.
Figure 3:
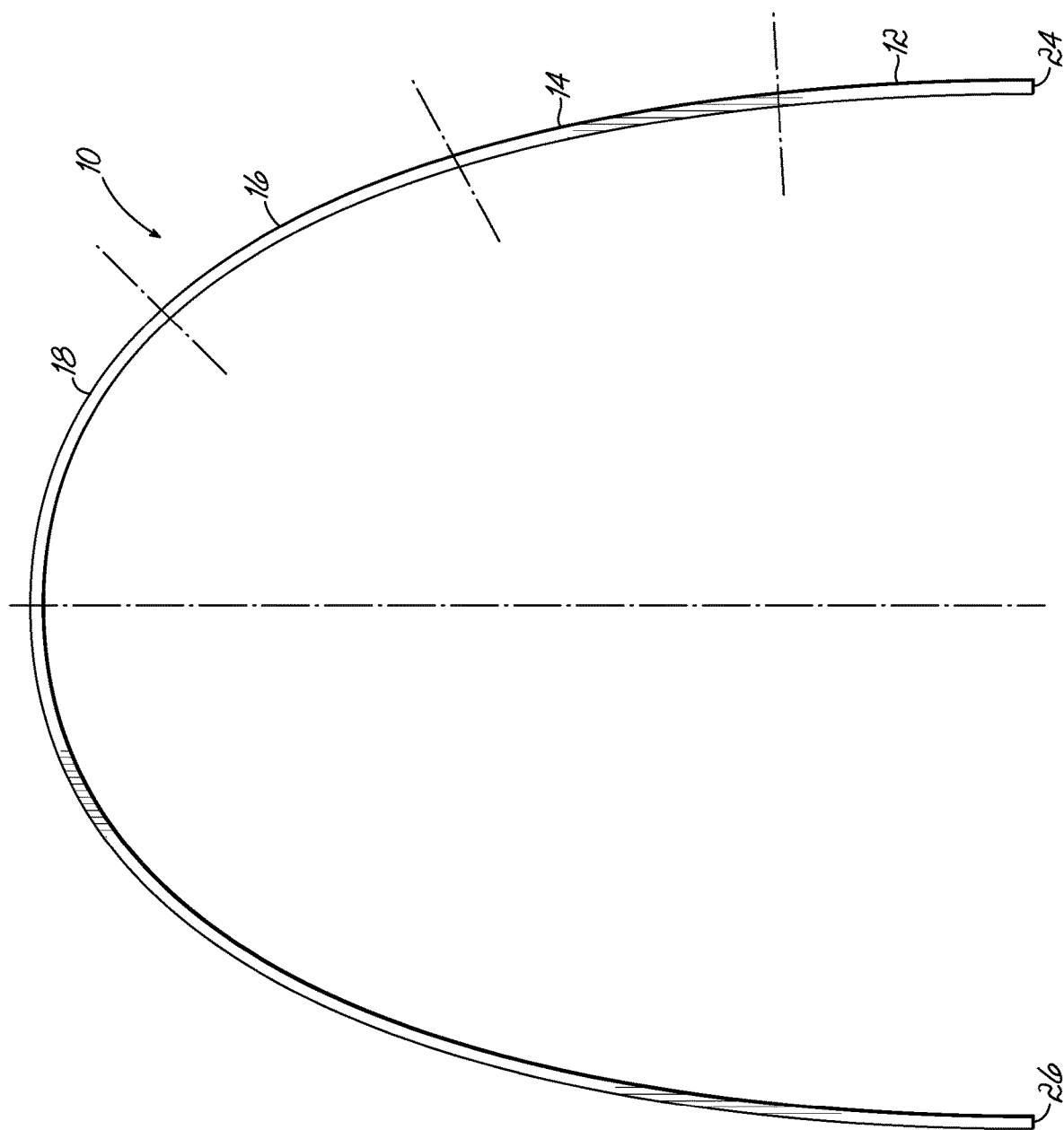
FIG. 3 is an elevation view of an orthodontic archwire according to one embodiment of the invention schematically illustrating different treated regions or zones.

Referring now to the drawings, and to FIGS. 1-3 in particular, one embodiment of the invention includes an orthodontic archwire 10 for use in orthodontic treatment. The archwire 10 includes multiple regions or zones 12, 14, 16, and/or 18. As set out in detail below, at least any two of the zones 12, 14, 16, and/or 18 differ in mechanical properties by virtue of a variation in the alloy composition in those zones. For example, the posterior zone 12 may generate a high load on the molars while the anterior zone 18 generates a lower load on the incisors. The mechanical properties of at least any two of the zones is predetermined by selectively changing the composition (i.e., the weight percentages of the elements present) of the SMA within that zone such that, during use, the zone applies a predetermined load to a corresponding tooth or group of teeth. As a result, any two of the zones 12, 14, 16, and/or 18 differ in composition so as to increase or decrease the $A_f$ for all or a portion of that zone from the $A_f$ of the base alloy or composition. Changing the composition of the SMA along the length of the archwire may allow the clinician to selectively produce different forces on different teeth. The process of selectively producing different zones having different properties within a SMA may be referred to as Multiple Memory Material Technology (MMMT) herein. For example, assuming there are 14 teeth in a dental arch, each archwire may be custom manufactured to deliver a unique force to each of the 14 teeth or any combination thereof. The clinician may therefore customize the archwire for the patient's specific malocclusion. By customizing treatment at the individual tooth level, the clinician may more quickly bring each tooth into its desired, aesthetic position.

To that end, according to one embodiment of the invention, and as set forth in more detail below, the archwire 10 is selectively treated with a laser in one or more of the zones 12, 14, 16, and/or 18. Laser treatment of shape memory materials is described in U.S. Pub. No. 2012/0192999, which is incorporated by reference herein in its entirety. Generally, applying energy via a laser beam to the surface of a SMA may cause a local change to the chemistry of the SMA. This local change in constituents may be by way of removal of a selected element or selected elements or by addition of a selected element. In either case, the relative atomic ratio of the elements in the treated area is changed from the original relative atomic ratio.

In the embodiment shown, the orthodontic archwire has a rectangular cross-section, shown best in FIG. 2, such that the archwire has a width 20 and a height 22 that defines the rectangular cross-section. It will be appreciated, however, that embodiments of the present invention are not limited to archwires having rectangular cross-sections, as other archwire cross-sections are known in the art, for example, circular cross-sectional configurations. Embodiments of the present invention specifically include round archwires.

According to embodiments of the present invention, the archwire 10 is made of a unitary piece of SMA, such as NiTi. In other words, and as will be described in more detail below, the archwire 10 is not a collection of individual sections of a SMA that are welded or brazed together to form an archwire. Furthermore, in one embodiment, the archwire 10 has a uniform cross-sectional configuration from one end 24 to the other end 26. For example, where the archwire 10 has dimensions of width 20 and height 22 corresponding to a rectangular cross-sectional configuration, the width 20 and height 22 are substantially constant from the one end 24 to the other end 26, as shown. In other words, the difference in mechanical properties between at least any two of the zones 12, 14, 16, 18 is not achieved by heat treating individual sections of SMA wire and then assembling those sections into the configuration of an archwire or by changing the cross-sectional dimensions of the archwire 10 along its length.

Figure 4:
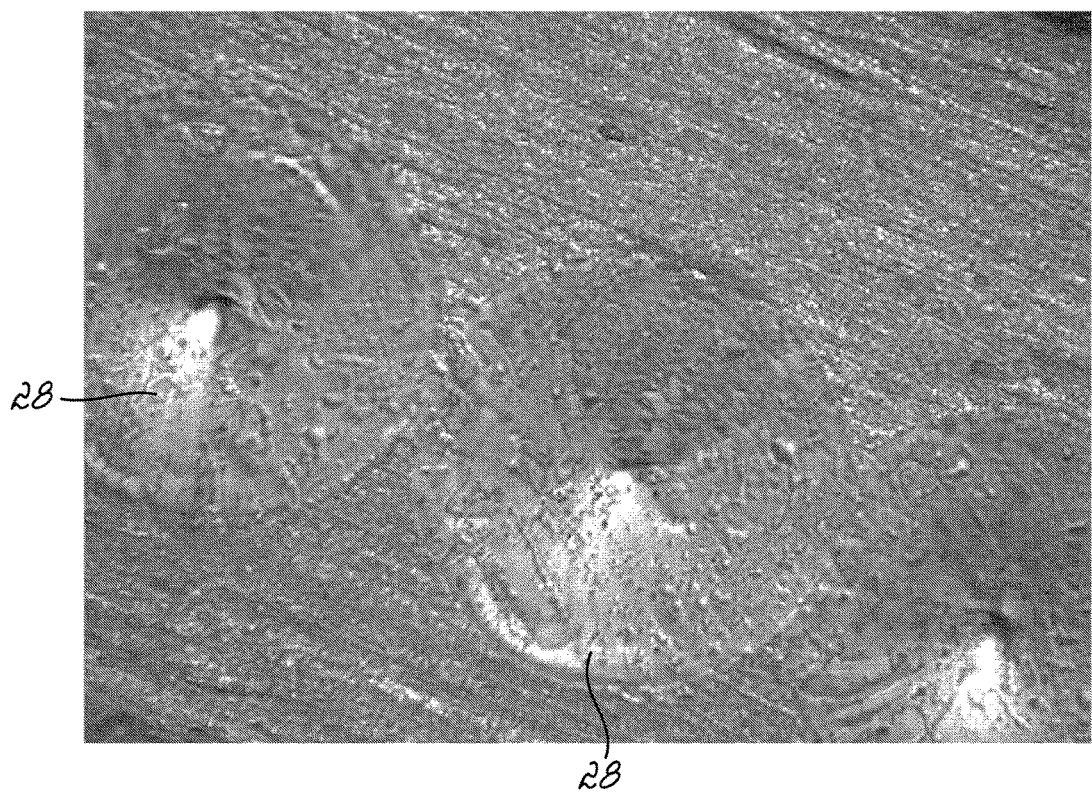
FIG. 4 is a Scanning Electron Microscope (SEM) micrograph of multiple treated regions according to one embodiment of the invention.
Figure 5:
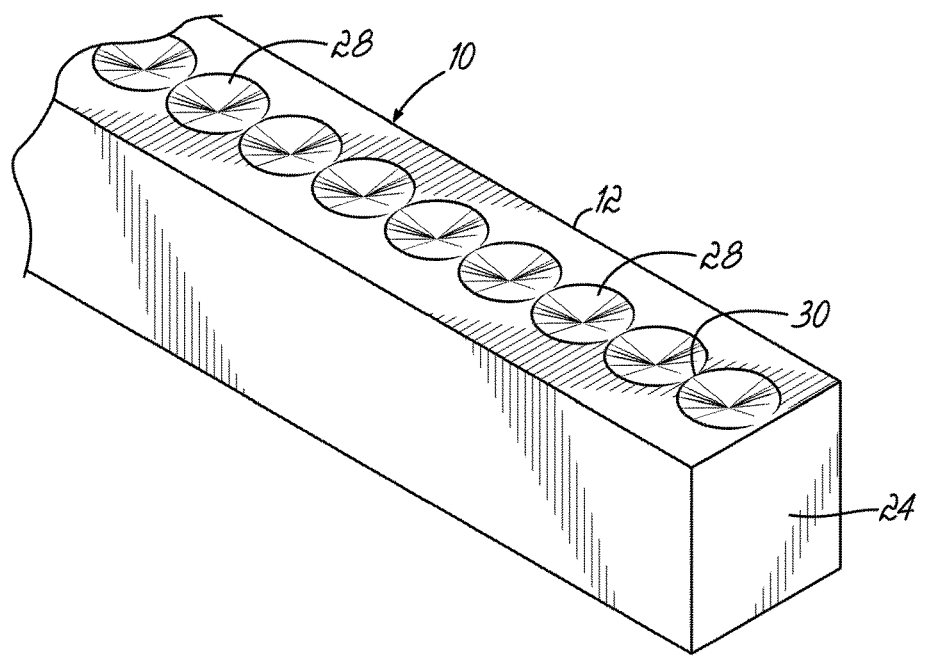
FIG. 5 is a perspective view of the encircled area 5 of FIG. 1 schematically illustrating a plurality of treated areas within one treated region or zone.

In one embodiment of the present invention, the archwire 10 is made of a SMA and is treated so as to change the composition of the alloy within one or more of the regions or zones 12, 14, 16, 18 (FIG. 3) to be different than the original, base alloy composition. By way of example, and with reference to FIGS. 4 and 5, in one embodiment, a laser beam may be utilized to treat one or more zones 12, 14, 16, 18, such as zone 12, of the archwire 10. With reference to FIGS. 4 and 5, the laser beam (not shown) may be focused on the surface of the archwire 10 to produce roughly circular treatment areas 28. The repetition of treated areas 28, by pulsing the laser beam across the surface of archwire 10, may result in overlap areas 30 between adjacent areas 28. By way of example only, and not limitation, the laser beam may be focused to produce an area 28 having dimensions as small as about 5 μm in diameter up to about 1000 μm (1 mm) in diameter. Furthermore, although not shown, the treatment areas 28 may be arranged so as to cover all or a fraction of the surface of the archwire 10. Therefore, by forming the treatment areas 28 with or without overlap areas 30, one or more treated regions or zones 12, 14, 16, and/or 18 or any portion thereof may be formed with the laser beam along the archwire 10. Multiple treated regions may be adjacent one another or separated by regions of the archwire 10 left untreated (i.e., untreated regions are of the base alloy composition.)

Treatment of the SMA with the laser beam may selectively remove one or more constituent elements of the alloy and therefore changes the composition of the alloy in the treated area 28. By changing the composition of the alloy, a local shift in the $A_f$ in the treatment area may be achieved relative to an untreated base alloy composition. For example, for NiTi, the laser beam may selectively remove nickel resulting in a fractional increase in titanium of the alloy composition in the treated area relative to the original bulk alloy composition. Selective removal of the nickel from a 50-50 NiTi alloy, for example, may result in an alloy having greater than 50 wt. % titanium in the treated area. The $A_f$ for the treated area may increase relative to the bulk or base alloy composition. By way of further example, for CuAlNi, processing with the laser or other localized high energy is believed to selectively remove copper and/or nickel resulting in a fractional increase in the aluminum of the alloy composition in the treated area relative to the original bulk alloy composition. For this alloy, however, the $A_f$ for the treated area may decrease relative to the bulk or base alloy composition. Further, the relative proportion of aluminum in the treated region scales with the plateau stress of a stress-strain response for the treated region.

Treatment may increase the concentration of a selected metallic element by addition of that element to a base alloy composition. This may be achieved by surrounding the base alloy composition with an alloy having the selected metallic element. For example, surrounding may include sandwiching a base alloy composition between sheets of foil of the selected metallic element to be added to the base alloy. Once surrounded, a laser may be used to locally heat the foil so as to selectively sublime or otherwise vaporize at least the selected metallic element. The vaporized element may then diffuse into the base alloy with the aid of the thermal energy supplied by the laser. The base alloy therefore receives a spike of a selected metallic element so as to form a treated region that differs from the base alloy composition by the selective increase in the metallic element.

In addition, laser treatment, which causes sublimation of one or more of the constituent metallic elements, may provide improved surface properties. For example, increasing the fractional percentage of titanium may induce growth of a tenacious oxide layer. The benefits of the oxide layer may include improved corrosion resistance and/or a reduction in any release of nickel from nickel-containing alloys. Other benefits to changing the surface chemistry of the alloy include formation of precipitants at the surface. For example, in NiTi alloys, a reduction in nickel may allow formation of titanium-rich nickel precipitants, such as $Ti_2Ni$, which are relatively hard compared to the base NiTi alloy composition. Such precipitants at the surface may reduce binding/friction dynamics at the wire-bracket contact regions. While NiTi alloys are specifically referred to, other alloys may be utilized for manufacturing orthodontic appliances according to embodiments of the invention including, but not limited to, copper nickel titanium (CuNiTi), copper chromium nickel titanium (CuCrNiTi), copper aluminum nickel (CuAlNi), copper aluminum manganese (CuAlMn), copper aluminum beryllium (CuAlBe), iron palladium (FePd), nickel manganese gallium (NiMnGa), and iron manganese silicon (FeMnSi) as well as other alloy compositions in which selected constituent elements may be sublimated or otherwise removed from a region or zone to thereby produce a localized change in the alloy composition in that region or zone.

In order to facilitate a more complete understanding of the embodiments of the invention, the following non-limiting examples are provided.

Example 1

Figure 6:
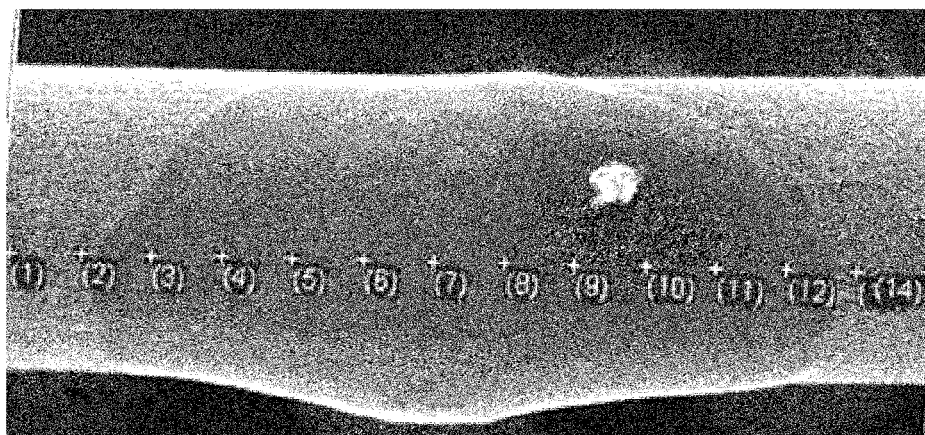
FIG. 6 is a SEM micrograph of a region of a round archwire treated with a laser beam according to one embodiment of the invention.
Figure 7:
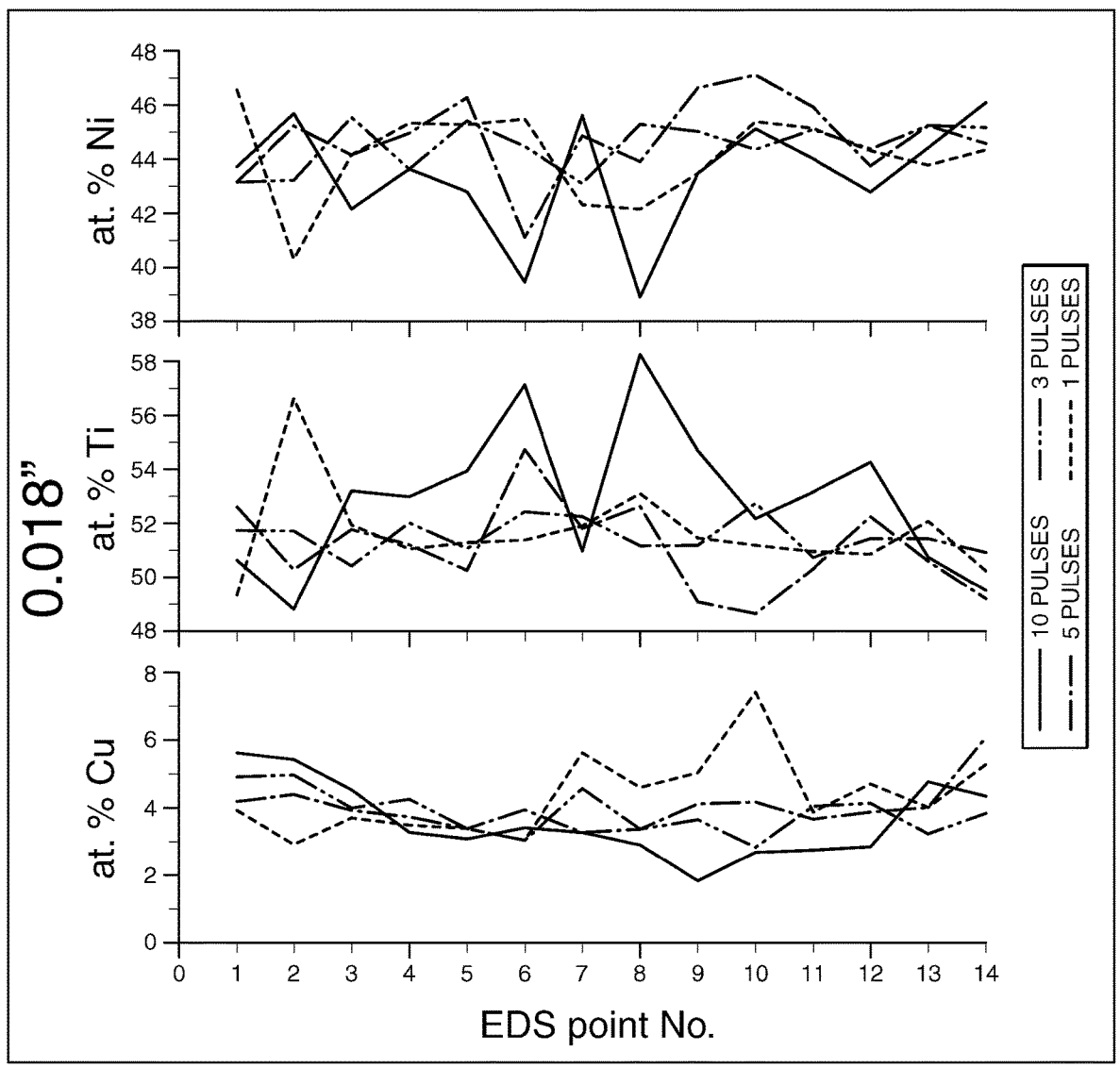
FIG. 7 graphically illustrates a change in the alloy composition of the archwire through the region treated with the laser beam shown in FIG. 6.

A round CuNiTi archwire shown in FIG. 6 was treated with a laser for a predetermined number of pulses. The base alloy composition of the CuNiTi archwire was 5 at. % Cu, 44.8 at. % Ni, 49.8 at. % Ti, and 0.2 at. % Cr. The CuNiTi archwire was commercially available from Ormco Corporation and sold under the trademark Damon Copper Ni—Ti®. The archwire was treated with a Fiber Laser with a laser beam spot size of 50 µm operating at a 30% peak power with 0.01 ms dwell time. The archwire shown in FIG. 6 was treated with one pulse of the laser and then the archwire was analyzed with an energy dispersive spectrometer (EDS) at the points indicated in FIG. 6. The EDS information is plotted in FIG. 7. Similarly, the archwire was treated with 3 total pulses, 5 total pulses, and 10 total pulses with each additional corresponding laser treatment being analyzed with the EDS. As shown in FIG. 7, generally between the EDS points 3 and 12, there is a relative increase in the atomic percent titanium and corresponding general decreases in the atomic percent nickel and atomic percent copper. These relative changes indicate that nickel and copper are removed from the treated area, presumably via sublimation.

As described above, the archwire 10 of the present invention may include one or more zones 12, 14, 16, 18 in which the composition of the alloy differs between any two or more of the zones. This is illustrated in Example 1, in which the treated area has an alloy composition with generally higher titanium content relative to the starting alloy content. And, after treatment, the treated area has a different composition than the composition of either of the adjacent, untreated areas. As a consequence, following laser treatment of selected zones 12, 14, 16, and 18, (FIG. 3) each may differ in $A_f$ and thus each zone may differ in the load produced by the zone during use. Specifically, as is shown in more detail below, changing the composition of the alloy along the length of the archwire changes the corresponding transformation plateau stress upon unloading of the archwire 10 in a tensile test. By way of example, a change in the composition of the alloy relative to the original bulk alloy may reduce the transformation plateau stress by up to about 75%, up to about 50%, or up to about 20%. It will be appreciated that the change in the transformation plateau stress may depend upon the composition of the original bulk alloy and the treatment selected.

Example 2

Figure 8:
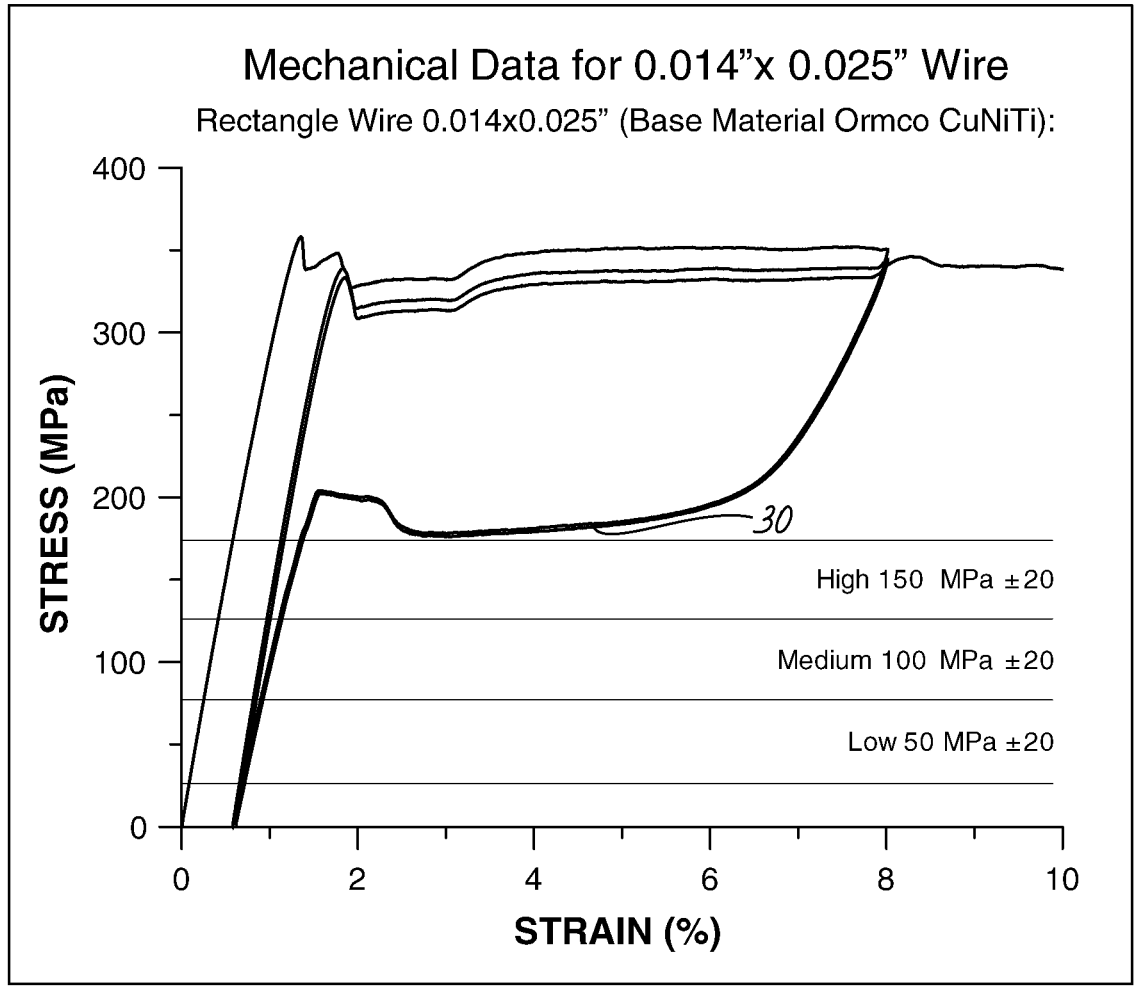
FIG. 8 is a graph of strain versus stress of an untreated region of an archwire.

With reference now to FIGS. 3 and 8-11, selected zones of a 0.014 inch by 0.025 inch rectangular CuNiTi archwire with the same composition as described in Example 1 were treated with the Fiber Laser. Zone 12 was left untreated. The mechanical data for untreated zone 12 is shown in FIG. 8. As shown, the transformation plateau stress upon unloading (indicated at 30) exceeds about 175 MPa.

Figure 9:
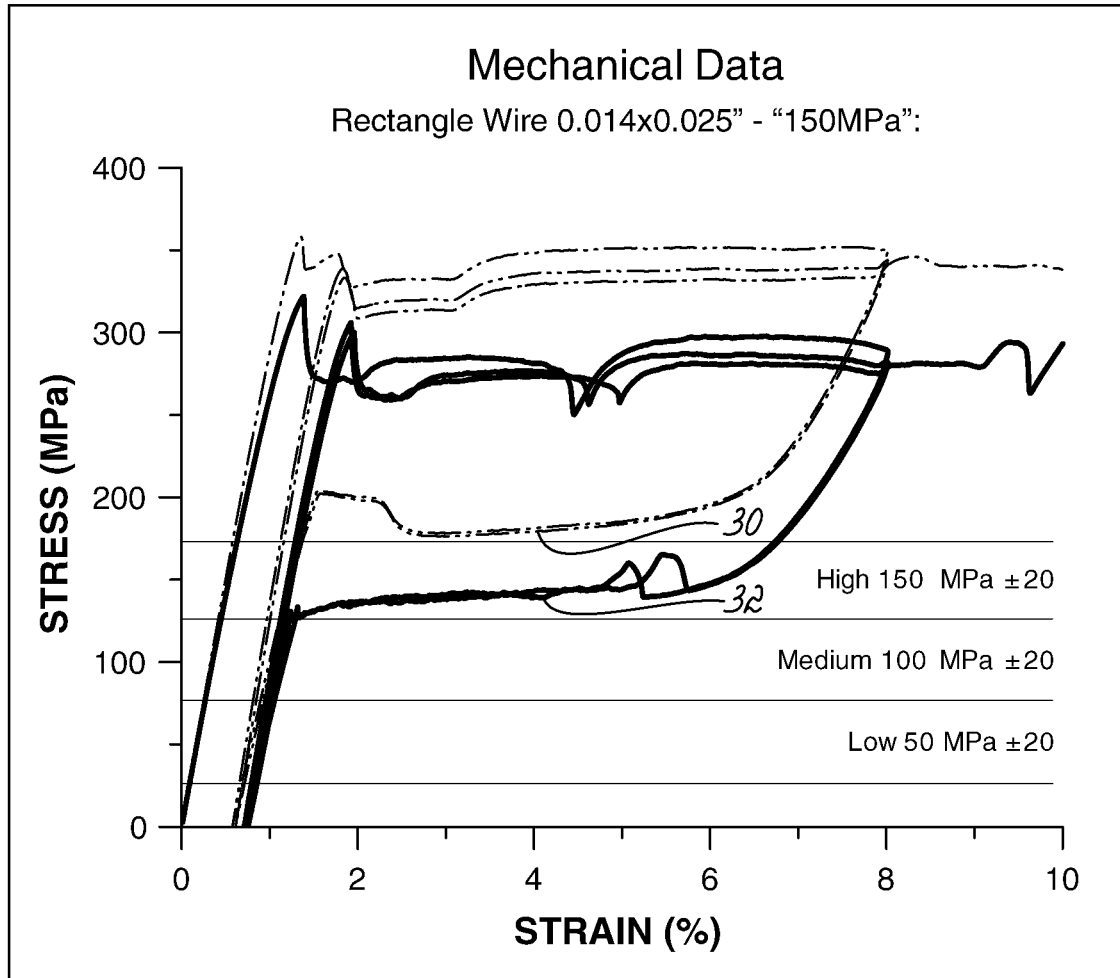
FIG. 9 is a graph of strain versus stress for the untreated region of the archwire as shown in FIG. 8 in comparison to a treated region of the archwire according to one embodiment of the invention.
Figure 10:
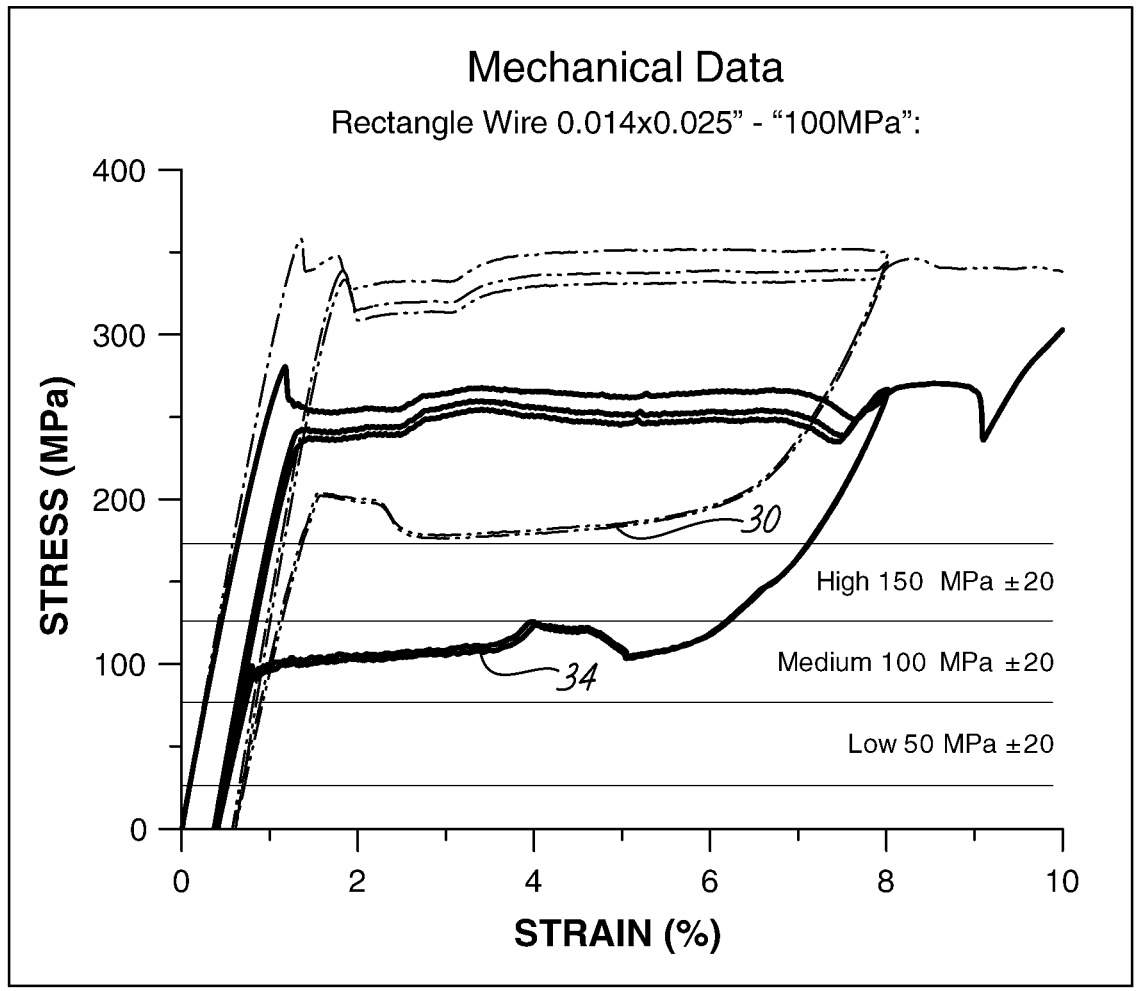
FIG. 10 is a graph of strain versus stress for the untreated region of the archwire as shown in FIG. 8 in comparison to a treated region of the archwire according to one embodiment of the invention.
Figure 11:
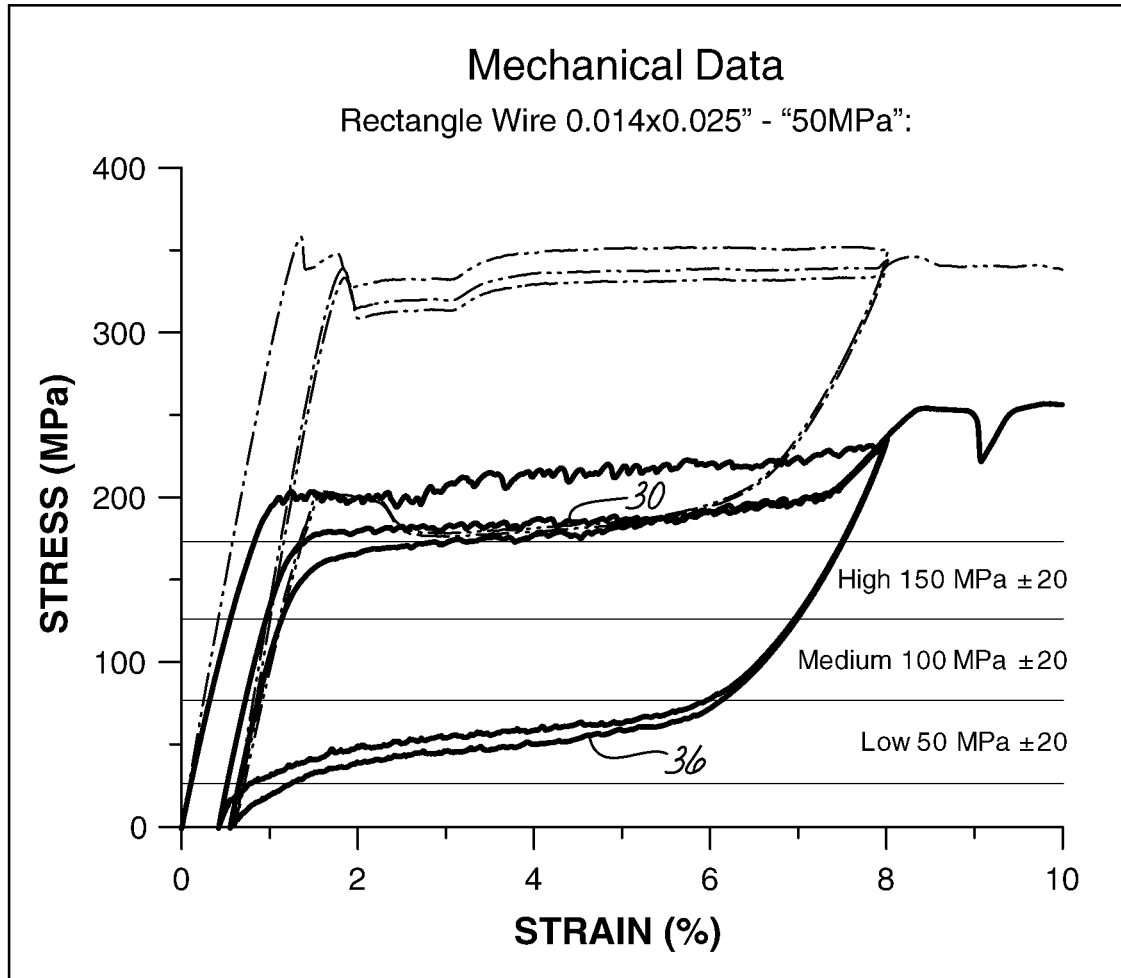
FIG. 11 is a graph of strain versus stress for the untreated region of the archwire as shown in FIG. 8 in comparison to a treated region of the archwire according to one embodiment of the invention.

Zones 14, 16, and 18 were individually treated with the Fiber Laser at different peak powers to produce different mechanical properties for each zone. Zone 14 was treated with the Fiber Laser with a laser beam spot size of 50 µm and a schedule of 0.01 ms dwell time at a peak power of 30%. FIG. 9 depicts the mechanical data following treatment of zone 14. As shown, the transformation plateau stress upon unloading (indicated at 32) measures about 150 MPa±20 MPa. Thus, following treatment, zone 14 exhibited a lower transformation plateau stress as compared to the transformation plateau stress of the untreated region indicated at 30. With reference to FIGS. 3 and 10, zone 16 was treated with the Fiber Laser similar to the treatment of zone 14 but with a peak power of 40%. FIG. 10 depicts the mechanical data for zone 16 following the above-described treatment. As shown, the transformation plateau stress upon unloading (indicated at 34) is about 100 MPa±20 MPa. Thus, following treatment, zone 16 exhibited a lower transformation plateau stress as compared to the transformation plateau stresses of each of untreated zone 12 at 30 and zone 14 at 32 (shown in FIG. 9). With reference now to FIGS. 3 and 11, zone 18 was treated with the Fiber Laser as set out above with regard to the treatment of zones 14 and 16 but with a peak power of 60%. FIG. 11 depicts the mechanical data for zone 18 following laser treatment. As shown, the transformation plateau stress upon unloading (indicated at 36) is about 50 MPa±20 MPa. Thus, following treatment, zone 18 exhibited a lower transformation plateau stress as compared to the transformation plateau stresses of each of untreated zone 12 at 30, zone 14 at 32 (shown in FIG. 9), and zone 16 at 34 (shown in FIG. 10).

Figure 12:
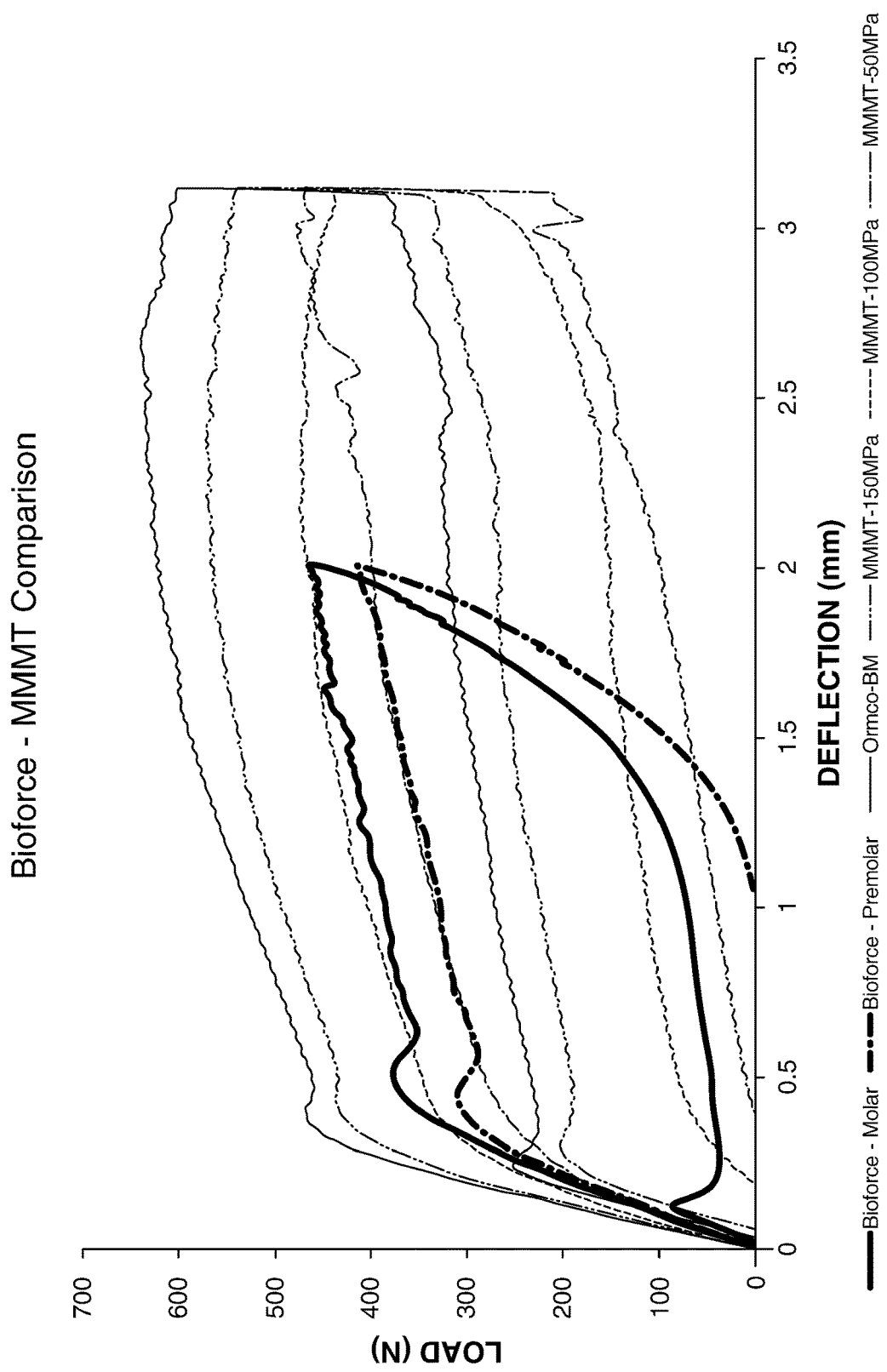
FIG. 12 is a graph of deflection versus load comparing the deflection versus load for each of the treated regions having stress versus strain relation depicted in FIGS. 9, 10, and 11 in comparison with the deflection versus load for two regions of a commercially available archwire.

The multizone archwire from Example 2 (above) was compared to a commercially available archwire sold by GAC International, Inc. under the trademark Bioforce®. The Bioforce® archwire was a NiTi (not CuNiTi) archwire. As shown in FIG. 12, different zones on each archwire were subject to 3-point bend testing on an Instron machine. As shown, while there is a small difference in the Molar and Premolar plateau stresses in the Bioforce® archwires, the treated archwire according to Example 2 provides a larger range in mechanical properties than the Bioforce® archwire.

In another embodiment, individual zones of a CuAlNi alloy archwire may be treated with a laser, such as the Fiber Laser, at different peak powers to produce different mechanical properties for each zone. This laser treatment may be similar to that described above. It is believed that this treatment of CuAlNi will selectively remove one or both of copper and nickel so as to change one or more of the ratio of copper to nickel, the ratio of aluminum to nickel, and the ratio of copper to aluminum. As a result, the relative proportion of aluminum in the treated region may increase. In this case, the mechanical data for different zones on the archwire, which contain different ratios of the constituent elements, may be similar to that shown in FIG. 13.

In this theoretical representation, and without being bound by theory, it is believed that removing copper and/or nickel from each treated zone may produce zones in which the transformation temperature for that zone decreases relative to the original composition. In other words, the transformation temperature for a particular zone may decrease with an increase in the concentration of aluminum in the zone versus the original composition.

Figure 13:
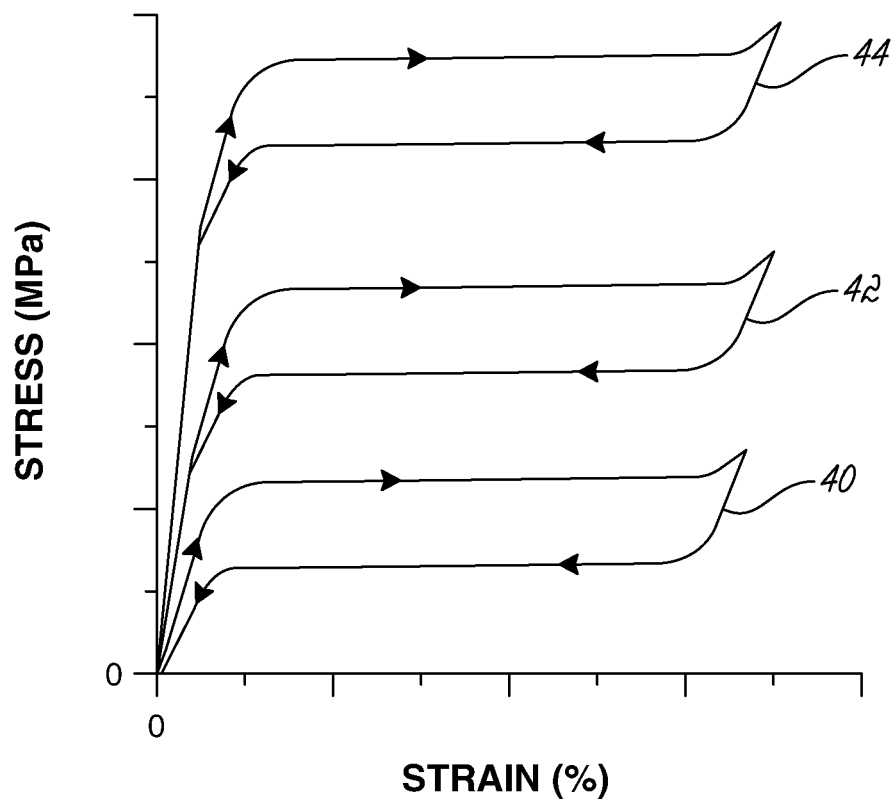
FIG. 13 is a theoretical graph of deflection versus load for a CuAlNi alloy after a plurality of treatments according to one embodiment of the invention.
Figure 14A:
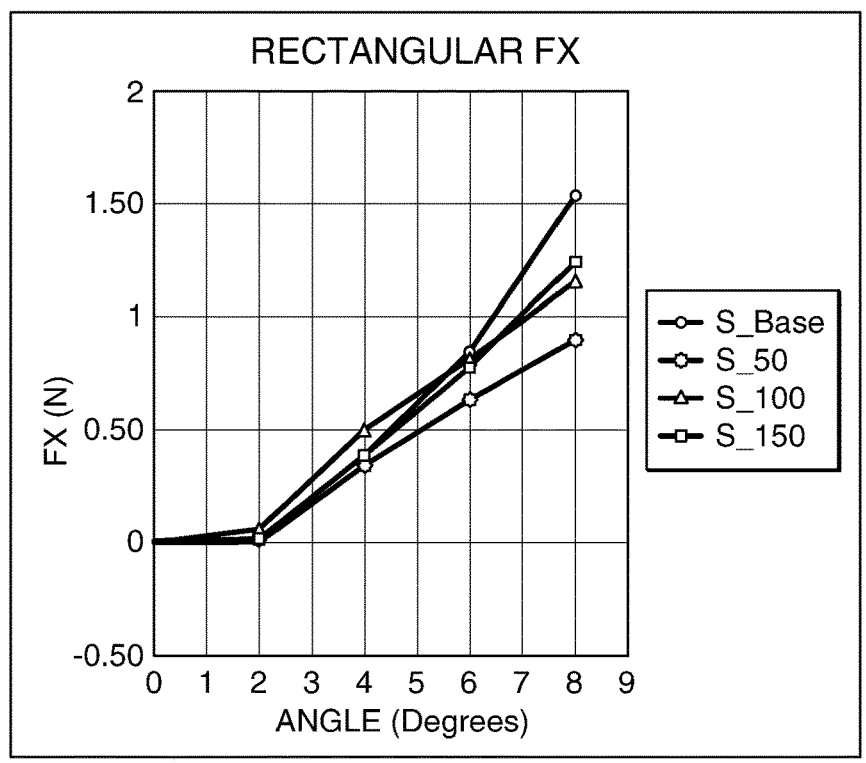
FIGS. 14A and 14B are graphs of friction versus angle and moment versus angle, respectively, for rectangular archwires treated according to one embodiment and intention in comparison with an untreated archwire.
Figure 14B:
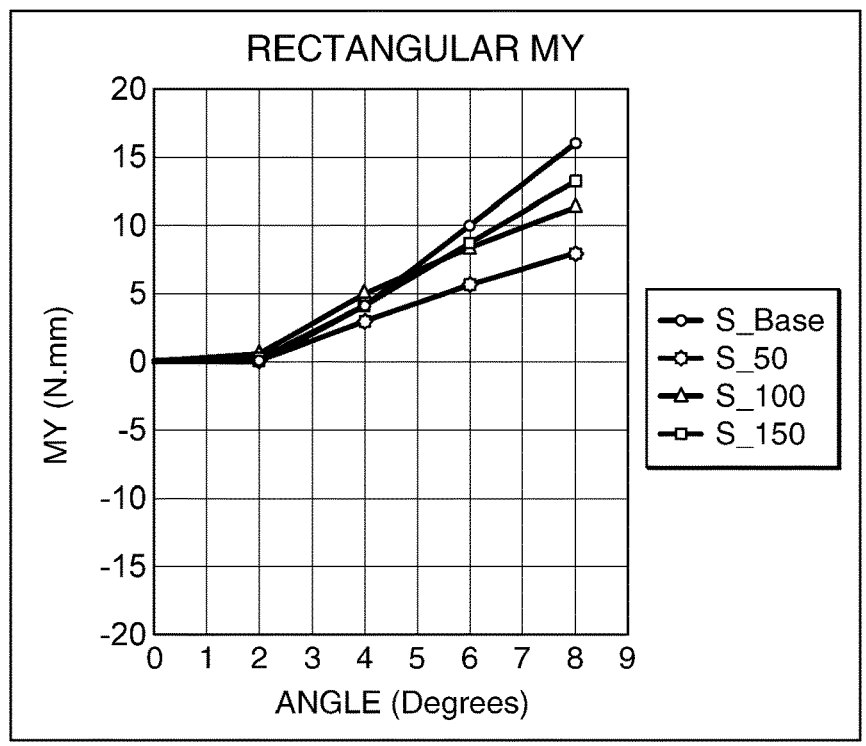
Figure 15A:
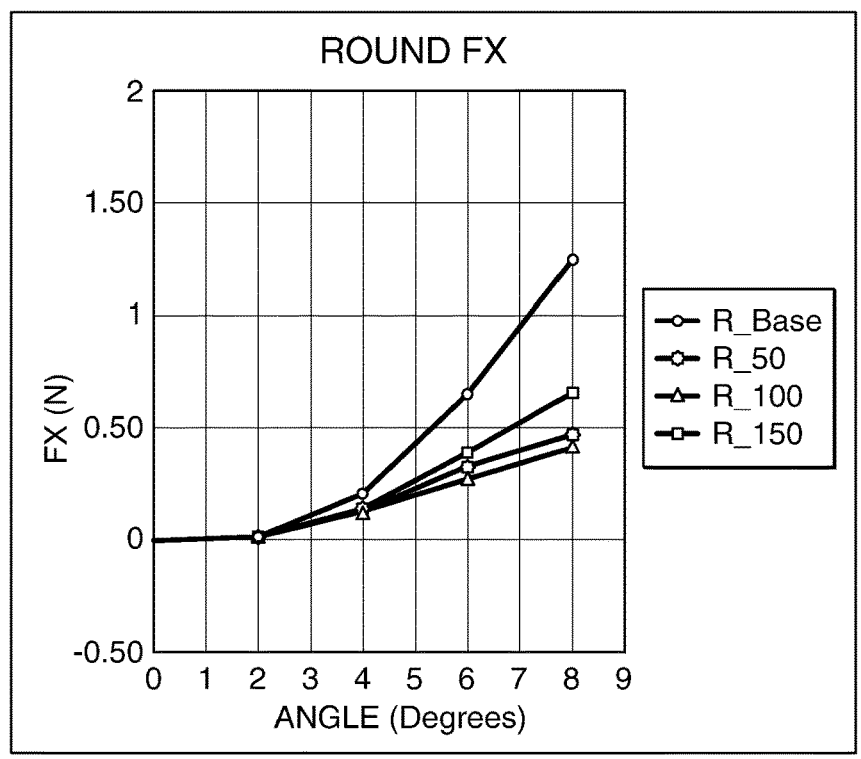
FIGS. 15A and 15B are graphs of friction versus angle and moment versus angle, respectively, for round archwires treated according to one embodiment and intention in comparison with an untreated archwire.
Figure 15B:
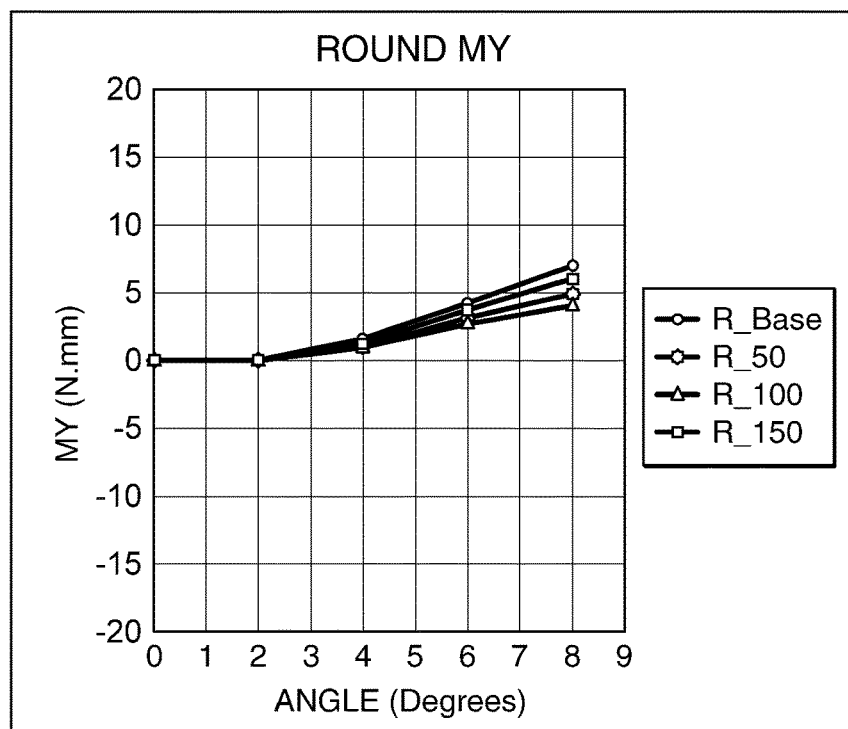

In addition, for example, and with reference to FIG. 13, the original composition of a CuAlNi alloy may have a stress-strain curve illustrated by curve 40. After processing in which copper and/or nickel is removed and by which the relative proportion of aluminum in the treated area increases, the stress-strain curve may be illustrated by curve 42. By way of example and not limitation, the weight percent copper and/or nickel removed may be from about 0.01% to about 1%. After further processing in which more copper or nickel is removed and by which the relative proportion of aluminum in the treated area increases relative to that associated with curve 42, the stress-strain curve may be illustrated by curve 44. This is in contrast to NiTi in which a decrease is observed due to processing. Advantageously, a multiforce archwire of a base CuAlNi alloy having zones with an increase in aluminum relative to the base composition may be produced. The treatment zones may have a predictable increase in stress-strain response relative to the base composition.

In summary, the effect of treatment of a CuAlNi alloy may be to increase the magnitude of the stress associated with increasing strain in the treated zone. The relative increase in aluminum content of the alloy in the treated area may manifest itself in a decrease in the $A_f$. This relationship may be linear over at least small (i.e., less than 1 wt. %) increases in the aluminum content. For example, treatment resulting in an increase in aluminum content may result in a shift in the plateau stress of about −2.2 MPa/° C. and about a 305 MPa increase in the plateau stress per percent increase in aluminum. Another effect of treatment may be a change in the microstructure. For single crystal CuAlNi alloys, treatment may result in formation of a polycrystalline CuAlNi alloy, which is generally more rigid than a single crystal alloy.

Example 3

Referring now to FIGS. 14A, 14B, 15A, and 15B, additional CuNiTi archwires of the same composition as in Example 1 were processed according to the process described in Example 2. One set of archwires were rectangular 0.018 inch by 0.025 inch archwires and another set of archwires were round 0.018 inch diameter archwires. Similar to Example 2, the treatment produced similar average plateau stresses of 50 MPa, 100 MPa and 150 MPa corresponding to the designations "S_50," "S_100," and "S_150," respectively, for the rectangular archwires and "S_Base" for the untreated base archwire material as indicated in the "Rectangular FX" graph of FIGS. 14A and 14B. Similar to Example 2, the treatment produced similar average plateau stresses of 50 MPa, 100 MPa, and 150 MPa corresponding to the designations "R_50," "R_100," and "R_150," respectively, for the round archwires and "R_Base" for the untreated base archwire material as indicated in the "ROUND FX" graph of FIGS. 15A and 15B.

Each treated archwire was subject to friction testing in the friction testing assembly at the University of Alberta. The friction test consists of pulling a short length archwire through an orthodontic bracket. The archwire is held in the clamping assembly, which is mounted on the end of a programmable linear microactuator. The linear actuator was programmed to move in increments at a prescribed constant speed for a predetermined distance.

An orthodontic bracket was bonded to a rotating stage that was connected to a 6-axis load cell. The wire was pulled through the bracket at specific angular orientations between the bracket and the archwire by rotating the stage to a predetermined angle relative to the archwire pull direction. The rotation angle was designed to simulate tipping, or second-order rotation, of the bracket relative to the archwire.

A high-speed data acquisition system captured data from the load cell to record the forces and moments as the archwire was pulled through the bracket body by the linear actuator. Among other forces, the component of the force in the direction of the archwire motion ("FX (N)" in FIGS. 14A and 15A) and the moment of the bracket about a direction perpendicular to the pull direction ("MY (N mm)" in FIGS. 14B and 15B) were measured. The friction apparatus was set up with the following parameters:

data acquisition rate 2000 Hz
    channel sampling 400 samples, non-moving average
    wire speed 0.05 mm/s
    wire increment 0.5 mm
    total wire travel 2.5 mm
    angle increment 2°
    angle range of motion 0°, 2°, 4°, 6°, 8° ("ANGLE (Degrees)" in FIGS. 14A, 14B, 15A, and 15B).

The length of each pull increment was selected so that the increment would span completely across the at least one of the processed zones on the treated archwire as described in Example 2.

As shown in FIGS. 14A, 14B, 15A, and 15B, the forces and moments observed on the treated archwires were generally less than the base alloy composition represented by "S_Base" and "R_Base" and the difference between the treated and base alloy composition (i.e., untreated alloy) became more pronounced at higher angles. The data indicates that, in addition to changing the transformation plateau stress of the archwire, the change in composition reduces friction between a bracket and the archwire at the treated surfaces.

Example 4

Similarly, four other CuNiTi archwires were treated according to the procedure set out in Example 2 for the "50 MPa" transformation plateau stress, namely, with the Fiber Laser at 60% of Peak Power and 50 µm spot size and 0.01 ms dwell time. The archwires were a 0.014 inch round archwire ("14 round" in the Table below), a 0.018 inch round archwire ("18 round" in the Table below), a 0.014 inch by 0.025 inch rectangular archwire ("14 rect" in the Table below), and a 0.018 inch by 0.025 inch rectangular archwire ("18 rect" in the Table below).

Each of the archwires was pulled through 3 offset brackets in artificial saliva with an Instron testing machine. In the test setup, the central orthodontic bracket in the series of three brackets was horizontally offset by 1 mm from the alignment of the remaining two brackets in a bowl of synthetic saliva at 35° C. An archwire was passively ligated in each of the brackets and then was pulled through the brackets. The force to pull the wire was measured and averaged over an 11 mm travel span. The bracket slot dimensions were 0.022 inch× 0.028 inch×0.115 inch.

| | To 11 mm Binding Force Average (N) | | | |
|---|---|---|---|---|
| | 14 round | 18 round | 14 rect | 18 rect |
| Base | 2.337984 | 17.18927 | 8.641715 | 17.18927 |
| 50 MPa | 2.277736 | 4.739781 | 6.116437 | 10.00069 |
| 150 MPa | 1.583601 | 4.811611 | 5.667267 | 16.52066 |
| 50 MPa Difference (compared to base alloy composition) | −3% | −72% | −29% | −42% |
| 150 MPa Difference (compared to base alloy composition) | −32% | −72% | −34% | −4% |

All laser treated archwires showed some improvement in the reduction in binding force relative to the base alloy composition.

Example 5

A 0.018 inch by 0.025 inch CuNiTi archwire was processed with the Fiber Laser with a laser beam spot size of 50 μm and a schedule of 0.01 ms at a peak power of 35%. The treated archwire (designated "35% P-10 μs" in FIG. 17) and an untreated archwire of the same composition (designated "018×025-BM" in FIG. 16) were cycled 10 times in a tensile test for the purpose of determining whether the laser treatment deteriorated the fatigue resistance relative to the base metal composition.

Figure 16:
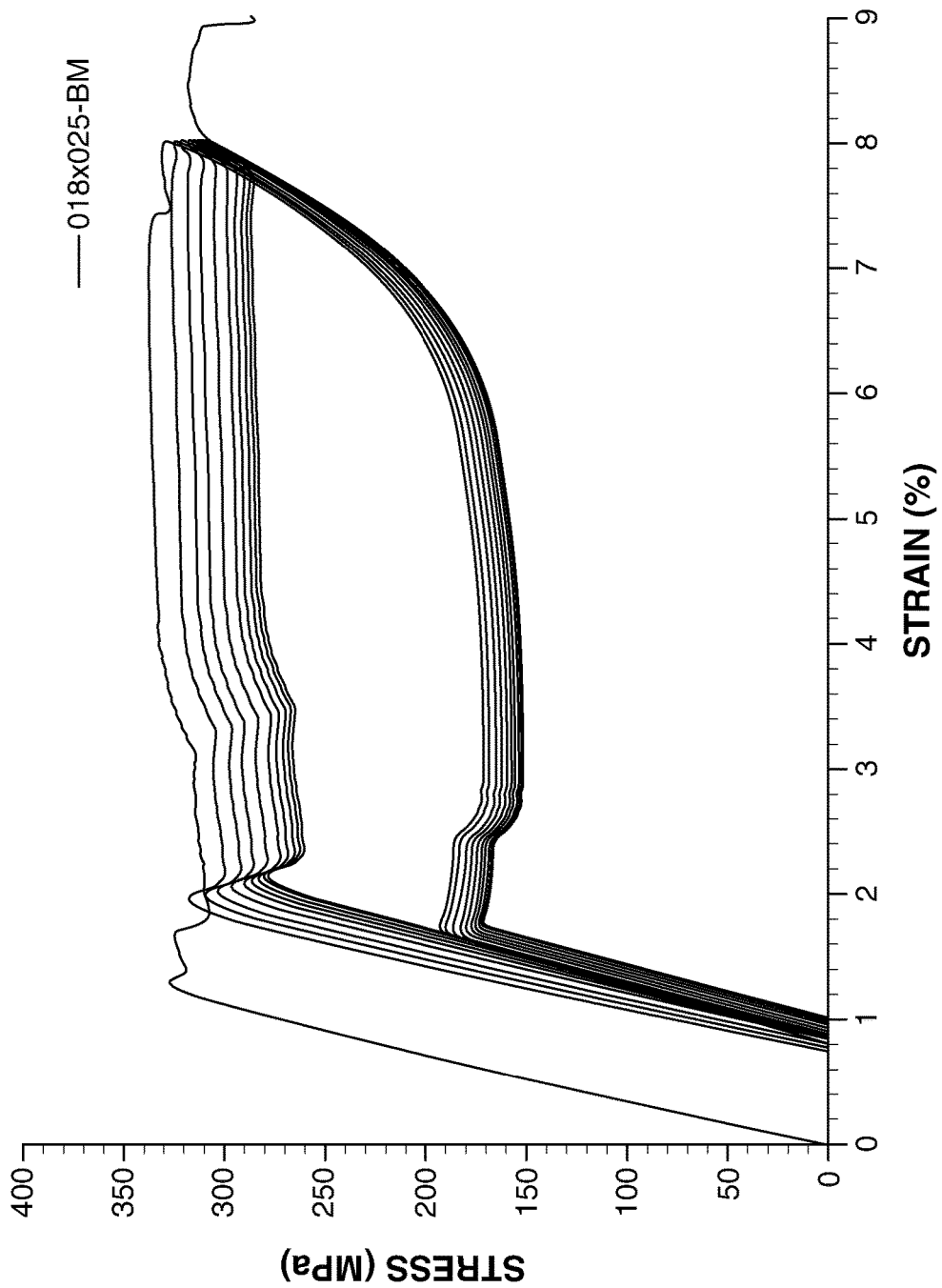
FIG. 16 is a graph of strain versus stress for an untreated archwire in cyclic tension loading.
Figure 17:
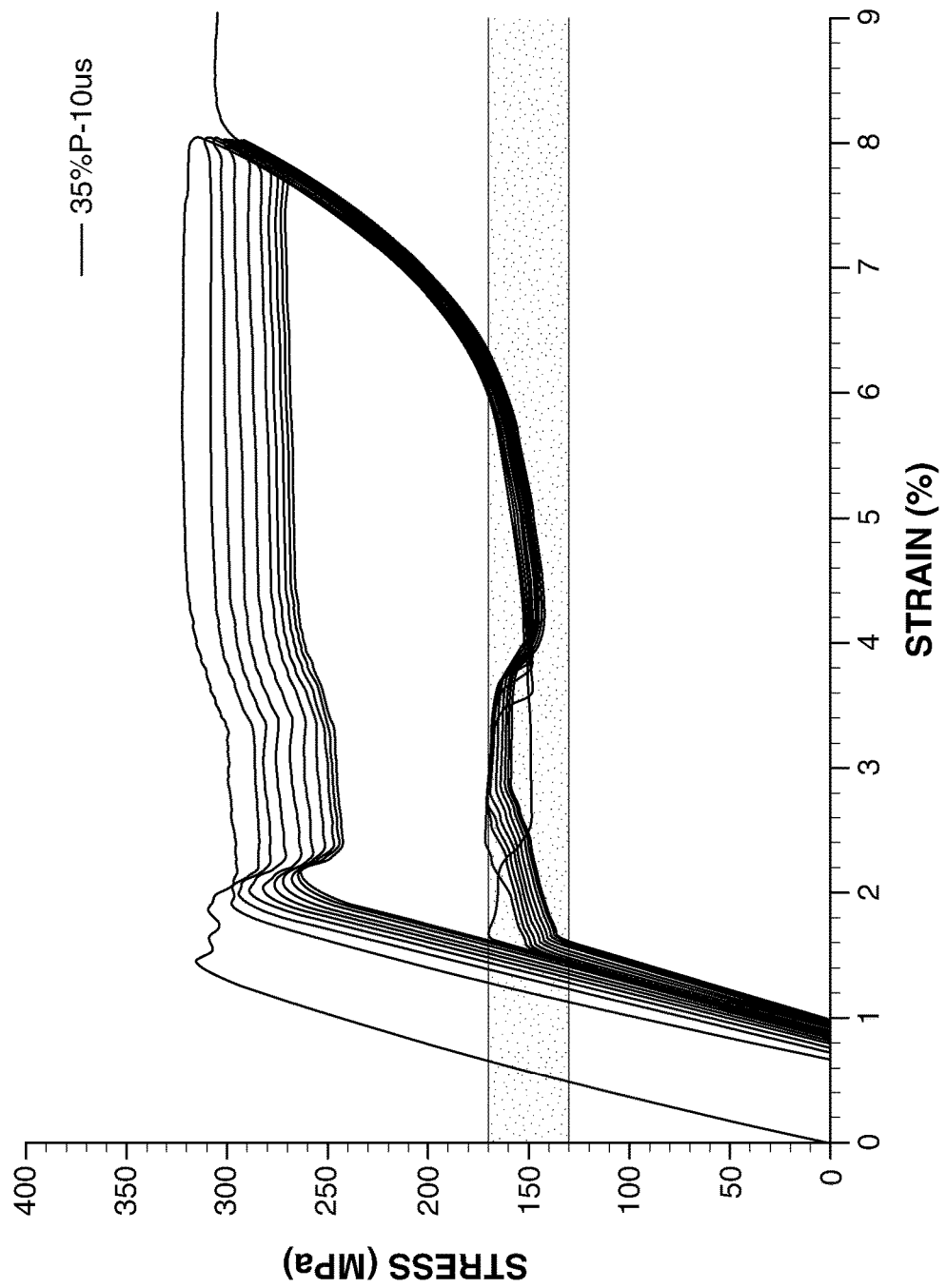
FIG. 17 is a graph of strain versus stress for an archwire treated according to one embodiment of the invention in cyclic tension loading for comparison with FIG. 16.

FIG. 16 depicts the results of cyclic loading on the untreated base alloy composition. FIG. 17 depicts the results of cyclic loading on the laser treated alloy composition. By comparing FIG. 16 with FIG. 17, the results of the testing indicate that laser treatment does not cause fatigue or degradation of the cyclic mechanical properties of the base alloy composition.

Example 6

Figure 18:
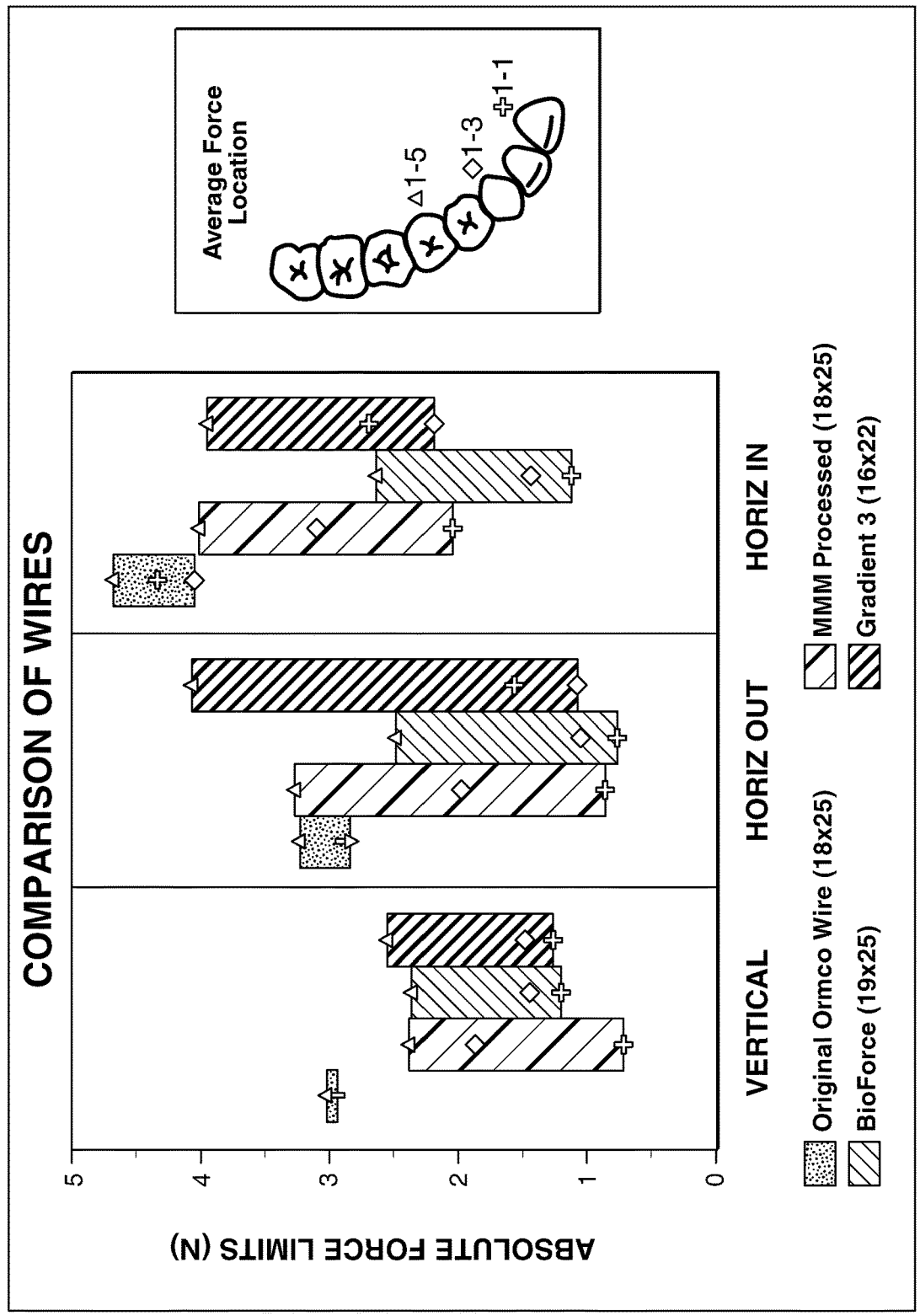
FIG. 18 depicts graphs of OSIM results for treated archwires for comparison with untreated archwires and commercially available archwires.

The 0.018 inch by 0.025 inch archwires of Example 5 were used on an Orthodontic Simulator (OSIM) developed by the University of Alberta. The results of the OSIM are shown in FIG. 18. In the figure, the "Absolute Force Limits (N)" correspond to the applied force on the tooth by the archwire at the different locations indicated in the "Average Force Location" legend. In particular, the central (incisor) location of the dental arch is indicated at 1-1, the bicuspid (canine) location is indicated at 1-3, and the premolar location is indicated at 1-5 for each of the archwires. FIG. 18 also indicates the direction of the measured force, i.e., "VERTICAL" refers to forces measured in the occlusal-gingival direction, "HORIZ OUT" refers to the forces measured in the outwardly or labial direction, and "HORIZ IN" refers to the forces measured in the inwardly or lingual direction.

The MMM Processed 0.018 inch by 0.025 inch archwires were processed according to Example 2. Each included a region or zone having a plateau stress of 50 MPa, 100 MPa, and 150 MPa. During OSIM testing the 50 MPa region was aligned with 1-1, the 100 MPa region was aligned with 1-3, and the 150 MPa region was aligned with 1-5.

The results of OSIM testing of the MMM Processed archwires were compared to similar results from the testing of commercially available archwires in the same orientation. Specifically, in FIG. 18, the MMM Processed archwires are compared to commercially available CuNiTi archwires without processing (i.e., "Original Ormco Wire (18×25)"), a Bioforce® archwire, and a Gradient 3 archwire commercially available from Ultimate Wireforms, Inc. Each of the Bioforce® archwire and the Gradient 3 archwire were NiTi alloys.

The relative height of each bar represents the relative force gradient capability of the archwire in the measured force direction. Generally, the larger the bar for each individual measured force direction and the more overlap between bars for each direction of force measurement, the greater the clinical capability of the archwire. The notable difference with the force gradients plotted in FIG. 18 is that the MMM Processed archwire consistently provided a force equidistant between the central location (1-1) and the pre-molar location (1-5) in each measured direction. In contrast, the Gradient 3 and Bioforce® archwires provided forces at the cuspid location (1-3) and the central location (1-1) that were much closer together, which is indicative of an abrupt increase in force along the archwire before the pre-molars.

Figure 19:
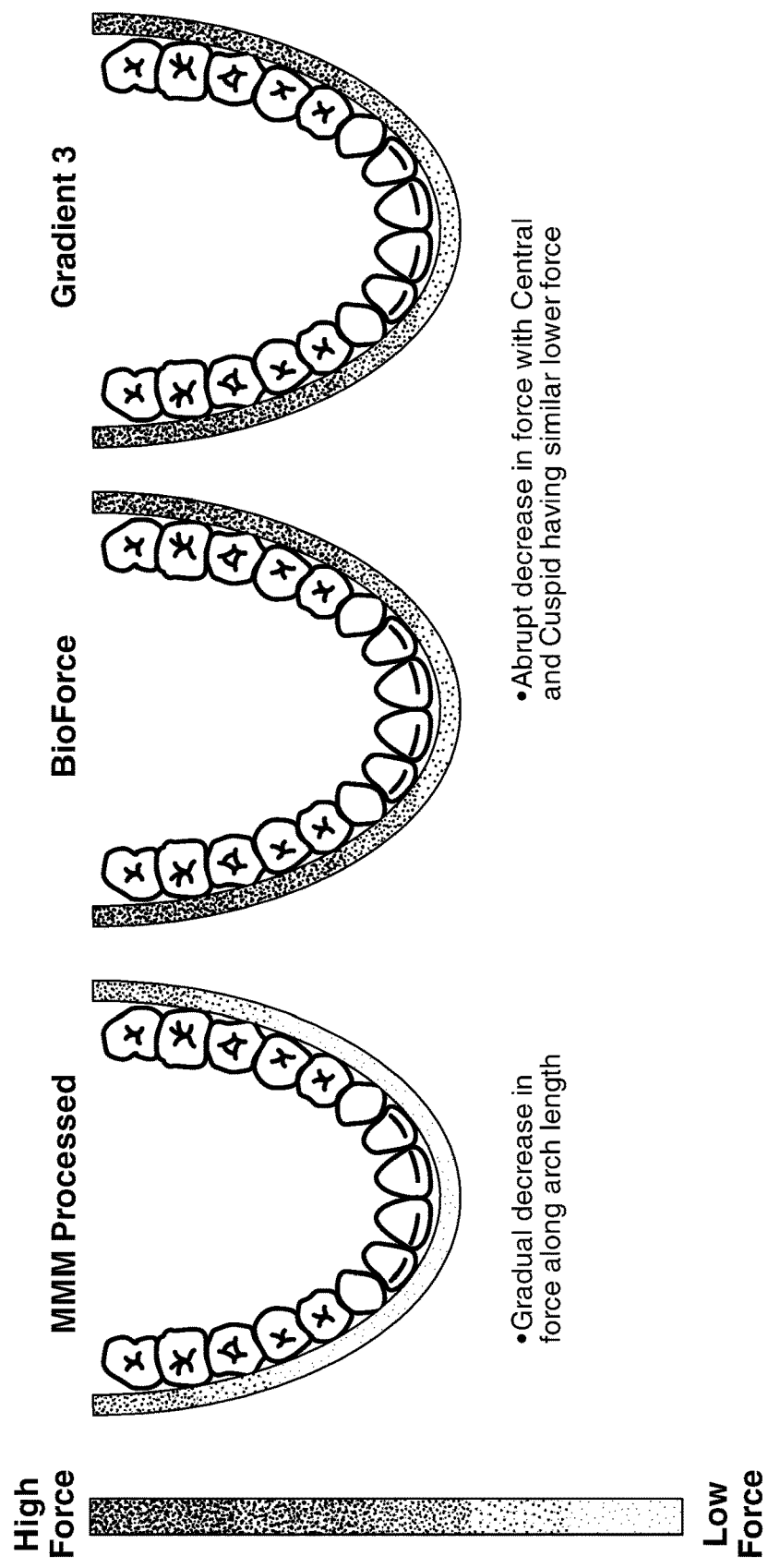
FIGS. 19 and 20 are schematic illustrations of vertical force distribution and horizontal force distribution along a dental arch, respectively, for one embodiment of the present invention in comparison with commercially available archwires.
Figure 20:
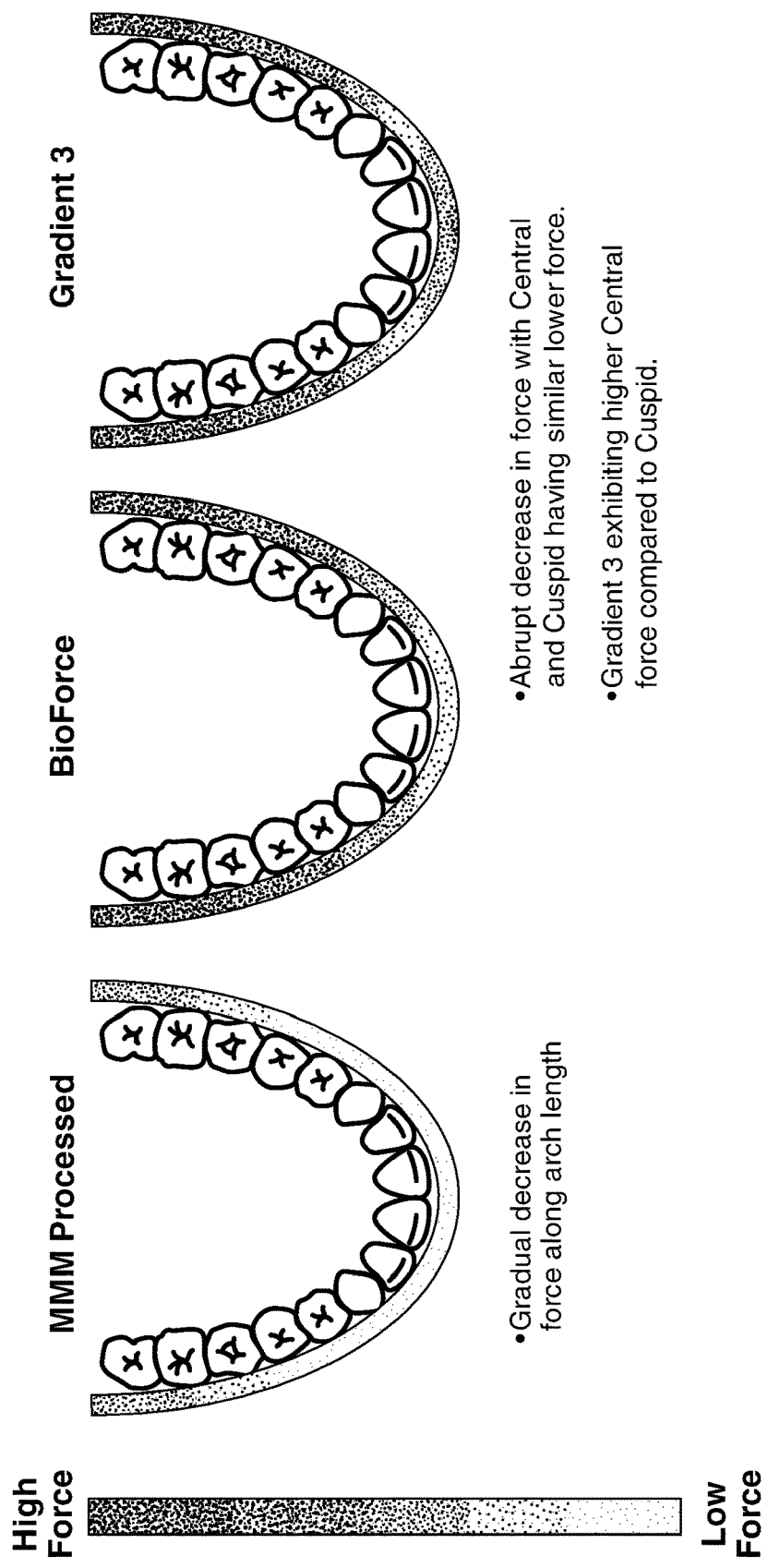

Referring now to FIGS. 19 and 20, the OSIM data plotted in FIG. 18 are schematically illustrated to facilitate a different visual comparison of the capability of the Bioforce® archwire and the Gradient 3 archwire to the MMM Processed archwire according to one embodiment of the invention.

As is indicated schematically in each of FIGS. 19 and 20, the MMM Processed archwire provides a gradual decrease in the force along the arch length when compared to each of the Gradient 3 and Bioforce® archwires. The MMM Processed archwire exhibits the highest force generated on the posterior teeth but then provides a gradual decrease in force applied to the anterior teeth.

Example 7

Figure 22:
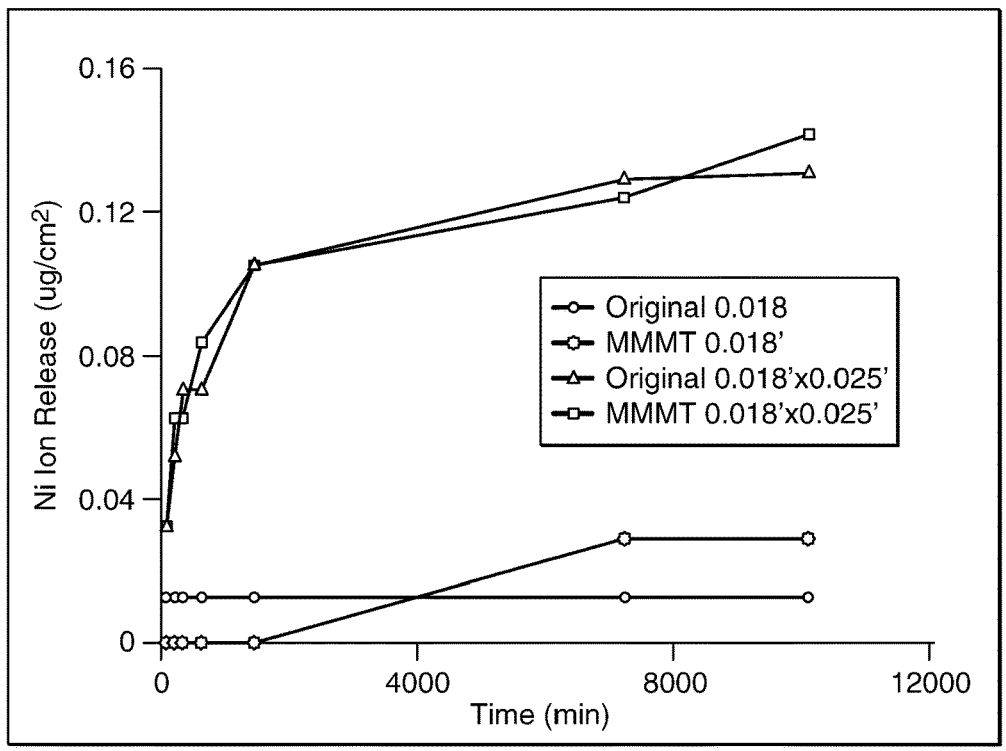
FIG. 22 is a graph of nickel ion release versus time comparing one embodiment of the invention with an untreated archwire.

The 0.018 inch by 0.025 inch CuNiTi archwires of Example 6 were subject to corrosion performance evaluation. In this test, the leaching of nickel ions from the archwire was measured over a period of 7 days in an artificial saliva solution incubated at body temperature. An inductively coupled plasma optical emission spectroscopy (ICP-OES) system was used to detect the amount of nickel ions in the solution at predetermined periods during the one week test. The amount of nickel ions for each archwire is shown in FIG. 22.

The nickel ion concentration was below the detection level of the ICP-OES for the 0.018 inch round wire. Each of the 0.018 inch by 0.025 inch archwires released detectable amounts of nickel ions for both the original, untreated archwire and the MMM processed archwire. As shown, the MMM processed wire does not increase the amount of nickel ion concentration in the artificial saliva solution relative to the amount of nickel released from the original, untreated archwire.

In addition to the nickel ion release testing, each of the original, untreated 0.018 inch by 0.025 inch archwire and the MMM processed 0.018 inch by 0.025 inch archwire was subject to cyclic polarization tests in the artificial saliva. The results of the tests are shown in FIG. 23.

Figure 23:
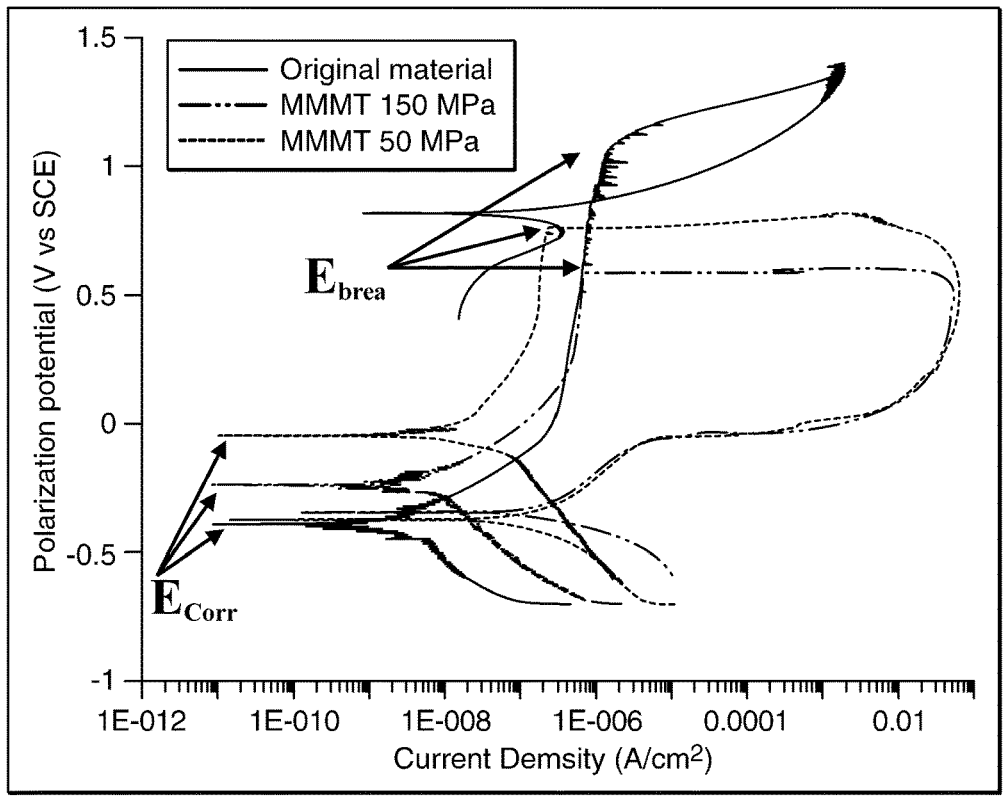
FIG. 23 is a graph of polarization potential versus current density comparing embodiments of the invention with an untreated archwire.

With reference to FIG. 23, there was an observable increase in the corrosion potential for the MMM processed archwires that is indicative of an overall decrease in the surface reactivity or an enhancement in the corrosion resistance of the MMM processed archwires. Without intending to be bound by theory, it is believed that laser processing the surface creates a protective surface oxide (e.g., $TiO_2$) coating while reducing the concentration of nickel at the surface.

Figure 21:
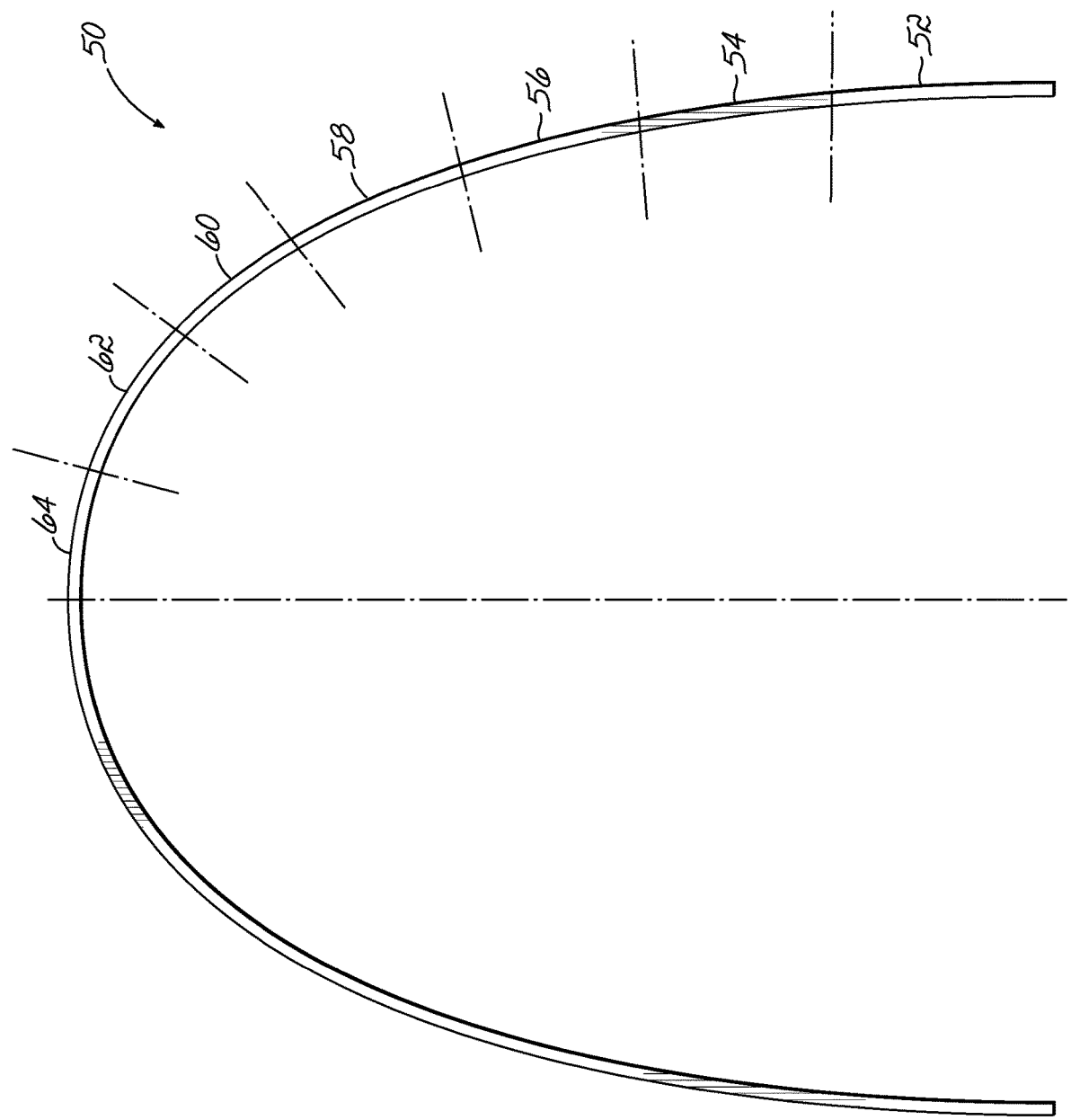
FIG. 21 is a graph of equivalent stress by zone for one embodiment of an archwire having multiple treatment zones.

In another embodiment and with reference to FIG. 21, an orthodontic archwire 50, for example, of a NiTi alloy or a CuNiTi alloy base composition, includes multiple regions or zones 52, 54, 56, 58, 60, 62, and 64. Each of the zones 52, 54, 56, 58, 60, 62, and 64 differ in mechanical properties by virtue of a variation in the alloy composition. For example, the posterior zone 52 may generate a high stress on the molars while the anterior zone 64 generates a lower stress on the incisors with the zones 54-62 producing stresses between the posterior zone 52 and the anterior zone 64. The mechanical properties of each zone are predetermined by selectively changing the composition (i.e., the weight percentages of the elements present) of the SMA within that zone such that, during use, the zone applies a predetermined stress to a corresponding tooth or group of teeth. In this embodiment, each of the zones 52, 54, 56, 58, 60, 62, and 64 differ in composition so as to predictably increase or predictably decrease the $A_f$ for all or a portion of that zone from the $A_f$ of the base alloy or composition.

As a result and according to one embodiment, each tooth to which the archwire 50 is secured during orthodontic treatment may receive a targeted, predetermined stress. This targeted stress may be predetermined by calculations specific to the patient's anatomy and/or based on the clinician's experience. Changing the composition of the SMA along the length of the archwire 50 may allow the clinician to selectively produce different forces on different teeth within a zone along the archwire 50, and thus target a desired stress for each tooth, or groups of teeth, by location on the specified arch.

For example, a Damon 0.014" round CuNiTi archwire may be processed to output forces for individual treatment zones according to the following table.

| Zone | $L_{1-1}$ at 64 | $L_{1-2}$ at 62 | $L_{2-3}$ at 60 | $L_{3-4}$ at 58 | $L_{4-5}$ at 56 | $L_{5-6}$ at 54 | $L_{6-7}$ at 52 |
|---|---|---|---|---|---|---|---|
| Normalized Target Stress[1] | 1 | 1 | 0.76 | 0.81 | 0.68 | 0.41 | 0.46 |
| E ratio[2] | 1 | 1 | 1.32 | 1.23 | 1.47 | 2.44 | 2.17 |
| Force (Newtons)[3] | 0.77 | 0.77 | 0.81 | 1.06 | 0.96 | 1.19 | 1.9 |
| Normalized Target Stress[4] | 0.59 | 0.9 | 0.64 | 0.67 | 0.66 | 0.36 | 0.38 |
| E ratio[5] | 1.69 | 1.11 | 1.56 | 1.49 | 1.52 | 2.78 | 2.63 |

[1]For teeth in the identified zone in FIG. 21 on the Lower Arch
[2]where E is the modulus of the archwire which is calculated under the assumption of equal Interbracket Distance (IBD) on the Lower Arch
[3]Calculated according the E ratio for the Lower Arch
[4]For teeth in the identified zone in FIG. 21 on the Upper Arch
[5]where E is the modulus of the archwire which is calculated under the assumption of equal IBD on the Upper Arch In general, the table lists specific forces for the lower arch that the archwire 50 is to produce. These forces are calculated based on the targeted stress for particular teeth at a particular location on the arch. In turn, the targeted stress may be used to calculate the required elastic modulus (E) of the archwire in that zone. This calculation may be based on equal IBD. Based on the elastic modulus (E), the amount of treatment by zone (i.e., at any single one of 52-64) may be predetermined. It is known that if interbracket distance (IBD) changes, the force required in a particular zone will also change and so the force/stress calculation may also include changes in IBD.

A pair of archwires, one for the upper arch and one for the lower arch may therefore be prepared. Each archwire may be processed to target a desired stress for a particular zone, as provided in the table above, so as to produce a targeted force on a tooth in that particular zone. In one embodiment, each tooth root (i.e., PDL) may receive an approximately equivalent stress Crowns and Bands Clinicians may use a crown or a band to attach a corrective appliance to a patient's dentition. Typically, crowns and/or bands are created from a mold of a portion of the patient's tooth so that the crown or band precisely conforms to the tooth surface. In order to retain the crown or the band on the tooth, bonding agents, such as adhesives, are used between the tooth and the crown or the band. Because the quality of the bond between the crown or the band and the tooth is a function of the skill of the person applying the adhesive and installing the appliance on the tooth, the bond is often the weak point of the installation. When the installation fails, it is often the bond that is the point of failure. Thus, there is a need to reduce the probability of bond failure in installations of crowns and/or bands.

According to embodiments of the present invention, utilizing MMMT may reduce or eliminate the use of a bonding agent and thus improve the patient's experience, may reduce time that the patient spends at the orthodontist's office, and may generally save the clinician's and patient's time.

Figure 24:
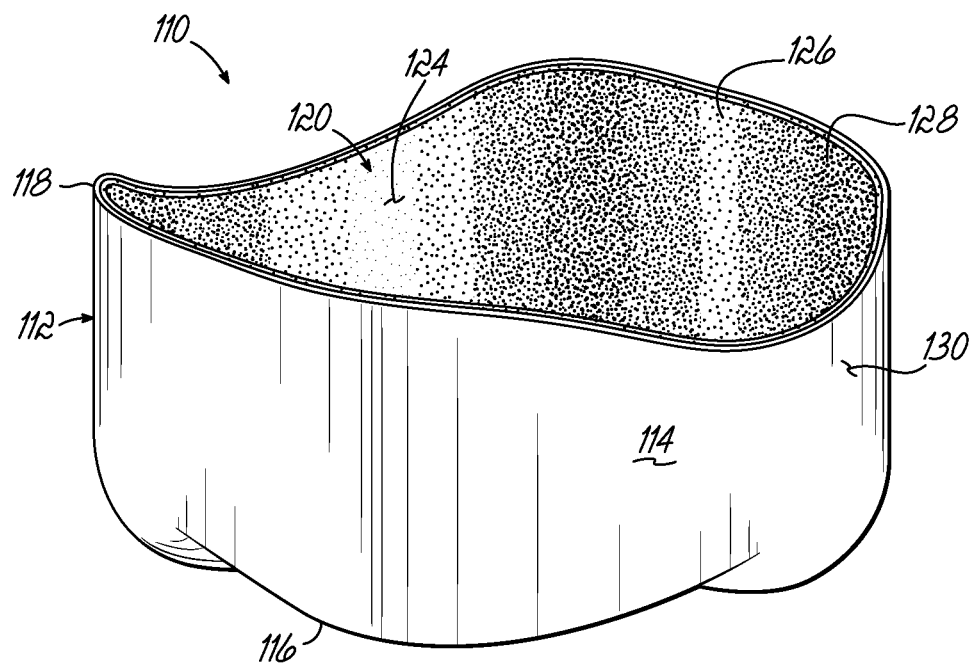
FIG. 24 is a perspective view of an orthodontic appliance in the configuration of a crown, according to one embodiment of the invention.

To that end, and with reference to FIG. 24, an orthodontic appliance according to one embodiment of the invention, includes a crown 110. The crown 110 includes a body 112 made of a SMA, such as those described above. As disclosed herein, "made of" is meant to mean that the entire body 112 consists only of the SMA, such as NiTi and CuNiTi. The body 112 may essentially be a shell of the SMA formed so as to have sidewall 114 and a coronal portion 116. The coronal portion 116 of the shell may be configured to mimic the shape of a coronal portion of the patient's tooth. The sidewall 114 may be continuous about the circumference of the body 112 and may terminate at an apical margin 118 and define an opening 120 for receiving the patient's tooth or other structure attached to the patient's arch. As shown, the opening 120 communicates with a cavity that is defined by the sidewall 114 and the coronal portion 116. The body 112 includes an inner surface 124, which may contact the tooth when the crown 110 is positioned thereon. In one embodiment, the inner surface 124 is treated with a form of energy, such as a laser beam, as described above, to thereby define a treated region 126. The treated region 126 may have treated areas or spots, such as the treated areas 28 with or without overlap areas 30 (shown in FIG. 5), formed by the laser beam impinging upon the surface. The treated region 126 may therefore be different in alloy composition from the base alloy composition of the SMA. Specifically, the alloy composition of the treated region 126 may differ by a relative deficiency in one or more of the constituent metallic elements, as described above. It will be appreciated that while the inner surface 124 includes the treated region 126, the treated region 126 may extend beyond the surface and into the body 112 to a predetermined depth or may extend entirely through the thickness of the shell of the crown 110 so as to form a portion of the inner surface 124 and the outer surface of the crown 110.

Because the treated region 126 includes a different chemical composition than the base alloy composition, it exhibits different material characteristics. In one embodiment, the treated region 126 exhibits an increase in $A_f$ relative to the $A_f$ of the bulk alloy composition. The $A_f$ of the treated region 126 may be less than the normal human core body temperature of 98.6° F., may be less than the typical oral temperature of 98.2° F., and may be less than the minimum core body temperature or oral temperature when normal daily variations in each of those temperatures are taken into account. With continued reference to FIG. 24, in one embodiment, the treated region 126 may define only a portion of the inner surface 124. For example, the inner surface 124 may include one or more treated regions 126 separated by one or more untreated regions 128 of the SMA. An "untreated region" is a portion of the crown 110 that has not been treated with the form of energy. Therefore, the composition of the alloy in the untreated regions 128 may be that of the base alloy composition. Alternatively, in one embodiment, not shown, the treated region 126 forms the entire inner surface 124, while the outer surface 130 remains untreated.

As described above, the crown 110 is suitable for placement on a molar, a premolar, or another tooth, and may either be placed on or used to replace a maxillary or mandibular tooth. However, persons skilled in the art will recognize that the crown 110 may be configured for placement on or replacement of other teeth, such as canines and incisors. Further, the crown 110 as described herein may be configured to receive corrective appliances, such as orthodontic brackets. Alternatively, the crown 110 may be used in cases where reparative or corrective action to a patient's dentition needs to be taken, such as with a broken or cracked tooth.

During installation, the clinician may deform the crown 110, specifically by enlarging the opening 120, if necessary, prior to inserting the crown 110 into the patient's mouth. Once placed over the tooth or other structure within the patient's mouth, the crown 110 will warm to the patient's body temperature from, for example, room temperature. In some instances, the clinician may initially cool the crown 110 below room temperature prior to deformation. For example, if room temperature is greater than $A_s$, cooling may include reducing the temperature of the crown 110 to a temperature below $A_s$ prior to deforming. In any case, the crown 110 is heated by contact with the patient from a temperature less than the normal oral cavity temperature, and possibly less than the $A_s$, to the temperature of the patient's mouth (i.e., the normal oral cavity temperature), which may be about the same temperature as or greater than the $A_f$ of the base alloy composition.

During heating, the crown 110 will recover its original shape by virtue of its shape memory property so as to conform to or be slightly smaller in one or more dimensions than the structure onto which the crown 110 is placed. Thus, as the crown 110 warms to the patient's body temperature, a compression or clamping force may develop on the tooth structure. The clamping force may be sufficient to eliminate the requirement of a bonding adhesive. In one embodiment, therefore, the installation of the crown 110 may be free of adhesive.

In addition, in one embodiment, the treated regions 126 may enhance surface-to-surface contact between the structure and the crown 110 due to a relative increase in the ductility at body temperature that accompanies an increase in the $A_f$ associated with the treated regions 126. In one embodiment, the $A_f$ of the treated region 126 is greater than the $A_f$ of the base alloy composition. It will be appreciated that with a higher relative $A_f$ of the treated region 126 compared to the $A_f$ of the base alloy composition, the treated region 126 will contain relatively larger proportions of martensite than the base alloy composition at the normal oral temperature. The increased ductility of the treated regions 126 generally associated with relatively larger amounts of martensite may allow the inner surface more intimately conform, possibly by deformation, to the tooth structure while under compression.

Figure 25:
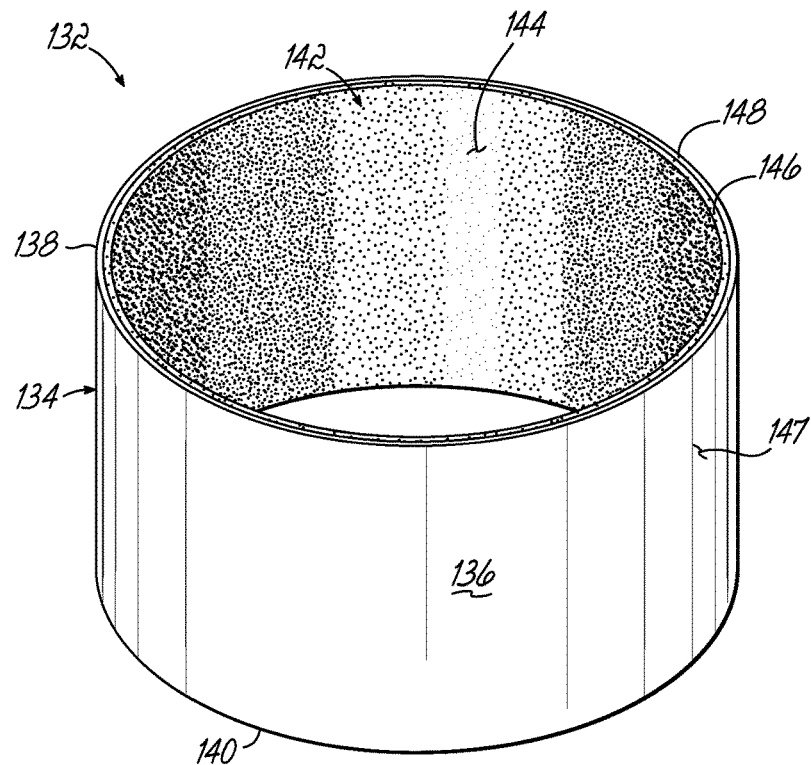
FIG. 25 is a perspective view of another orthodontic appliance in the configuration of a band, according to one embodiment of the invention.

With reference now to FIG. 25, in another embodiment of an orthodontic appliance, a band 132 has a body 134 defined by a sidewall 136 between coronal and apical margins 138, 140, respectively. As shown, the body 134 has a generally annular shape and, in the exemplary embodiment shown, has a cylindrical shape. It will be appreciated, however, that the body 134 may more closely conform to a shape of the tooth, so that it is not necessary that the body 134 have a regular annular configuration. Specifically, the body 134 may have an irregular annular configuration.

With continued reference to FIG. 25, the body 134 includes an opening 142 that is defined between the coronal and apical margins 138, 140 and that is configured to receive the patient's tooth when the band 132 is placed thereon. The sidewall 136 includes an inner surface 144, which contacts the tooth when the band 132 is placed on the tooth and includes an outer surface 147. Similar to the crown 110, described above, the inner surface 144 is treated with a form of energy, such as with a laser beam, to thereby define a treated region 146 that is deficient in one or more of the metallic elements relative to the base alloy composition. In the exemplary embodiment shown, the treated region 146 encompasses the entire inner surface portion 144, while the outer surface 147 remains untreated. It will be appreciated, however, that only part of the inner surface 144 may include the treated region 146. Persons skilled in the art will understand that the treated region 146 may extend into the body 134 a certain depth, toward the outer surface 147.

Similar to the treated region 126 of the crown 110, described above, the treated region 146 has a different alloy composition than the base alloy composition and therefore possesses different material characteristics, as described above. Namely, treatment of the SMA with a form of energy, such as a laser beam, may selectively remove one or more constituent elements from the base alloy composition such that the treated region 146 is deficient in at least one metallic element relative to the base alloy composition. As a result, the treated region 146 may exhibit a shift in one or more of the transition temperatures (i.e., $M_s$, $M_f$, $A_f$, and $A_s$) relative to the base alloy composition. In one embodiment, at least the $A_f$ of the treated region 146 is greater than the $A_f$ of the base alloy composition.

As described above with regard to installation of the crown 110, during installation of the band 132 on a tooth, the band 132 is heated by the patient's body. Heating the band 132 to the patient's body temperature may include heating the band 132 from a temperature of approximately room temperature to the patient's body temperature. This may be the situation where a clinician removes the band 132 from a package stored at room temperature and installs the band 132 into the patient's mouth. More specifically, heating the band 132 may include heating from a temperature cooler than room temperature to the patient's body temperature. This may be the situation where a clinician stores the band 132 in a refrigerator or other appliance that cools the band 132 to a temperature less than room temperature prior to installation of the band 132 into the patient's mouth.

In any case, the band 132, particularly the treated region 146, may exhibit characteristics of higher ductility at temperatures less than the temperatures in the patient's mouth. At temperatures less than body temperature, for example at room temperature, the clinician may deform the band 132 to enlarge the opening 142 to fit the band 132 on the tooth. In other words, due to the ductility of the band 132, the clinician will be able to essentially stretch the sidewall 136, particularly the treated region 146, and otherwise manipulate the shape thereof in order to place the band 132 on the tooth. Once the band 132 is placed on the tooth and is heated to the oral temperature, the shape-memory characteristic of the SMA will cause the band 132 return to its original shape to thereby more closely conform to the shape of the tooth. In particular, the band 132 may recover its original configuration when heated to the oral temperature.

The compressive force due to the shape memory property of the band 132 may provide sufficient clamping force to secure the band 132 to the patient's tooth. Specifically, as the deformed band 132 recovers its original shape as temperature of the band increases, recovery may include a reduction in the size of the opening 142 or one or more dimensions of the band 132 so as to provide compression on the tooth.

In addition or alternatively, the increased relative ductility of the treated region 146, by virtue of the relative increase of $A_f$ compared to the $A_f$ of the base alloy composition, may secure the band 132 to the tooth. It will be appreciated that the treated region 146 may include a larger proportion of martensite than the proportion of martensite in the base alloy composition at the oral temperature. The larger proportion of martensite in the inner surface 144 may facilitate plastic deformation of at least entreated region 146 under the compressive load from the shape memory action. The deformation of the inner surface 144 creates a more intimate contact between the inner surface 144 and the tooth surface. Because of these advantageous features of the band 132, use of bonding agents, such as adhesive, to provide adhesively secure the band 132 to the tooth may be unnecessary. In one embodiment, therefore, the clinician may install the band 132 without adhesive such that the installation is free of adhesive.

Stops and Hooks

Orthodontic stops and hooks are often made of metal. During installation, they may be crimped onto the archwire. Over time, however, the metal relaxes due to its ductility. As a consequence, the force holding the stop or the hook on the archwire degrades, causing partial or full disengagement of the stop or hook from the archwire. Under this condition, the stop or the hook ceases to function and requires the intervention of the clinician. Thus, there is a need for stops and hooks that remain more fully secured in position for the duration of orthodontic treatment.

Figures 26, 27:
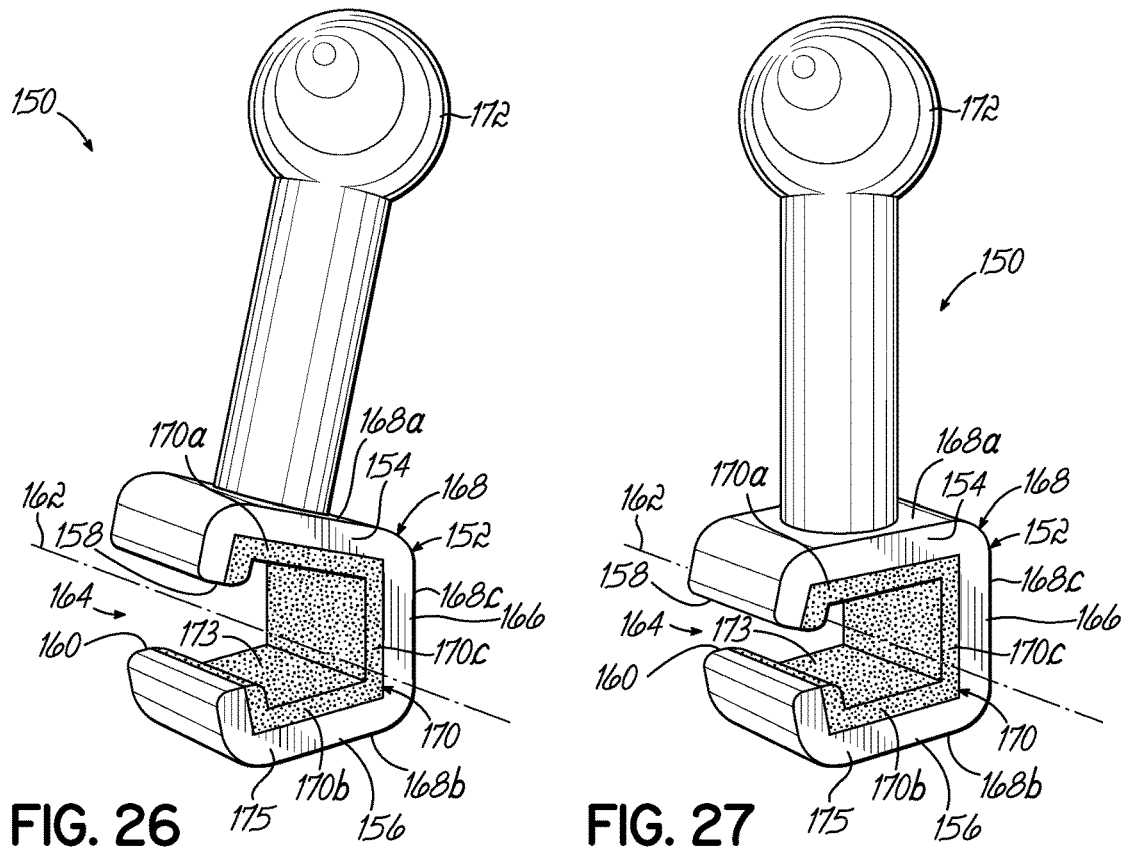
FIG. 26 is a perspective view of another orthodontic appliance in the configuration of a hook according to one embodiment of the invention, shown in an opened position.
FIG. 27 is a perspective view of the hook of FIG. 26 shown in a closed position.

Referring now to FIGS. 26 and 27, another embodiment of an orthodontic appliance is shown. Specifically, an orthodontic stop 150 for placement on an archwire (not shown) includes a C-shaped body 152 made of a SMA. The body 152 defines a longitudinal axis 162. The body 152 includes first and second opposing sides or portions 154, 156 each having opposing ledges or lips 158, 160. An opening 164 is defined between the first and second opposing portions 154, 156. As is known in the art, the opening 164 allows an archwire to be inserted therethrough to generally coincide with the axis 162 during installation. Thus, during installation, the size of the opening 164 may be enlarged by further separating the lip 158 from the lip 160 so as to allow an archwire to pass between them. The body 152 further includes a third side or portion 166 extending between the first and second portions 154, 156 and opposite the opening 164. The C-shaped body 152 has an outer surface 168 and an inner surface 170 configured to frictionally engage the archwire. It will be appreciated that the body 152 may have other cross-sectional configurations such that embodiments of the invention are not limited to the C-shape body 152 shown. For example, the shape of the cross-section of the C-shaped body 152 may also depend on the shape of the corresponding archwire (not shown) and in that regard the body 152 may have a generally circular cross-sectional configuration. As shown, in one embodiment, the stop 150 may include a hook 172, which may be used to provide an anchoring point for orthodontic elastics, ancillary devices, or other orthodontic or dental appliances, as is known in the art. The hook 172 may be made of a SMA though the hook 172 may be made of other materials and then soldered, bonded, or otherwise secured to the body 152.

In the embodiment shown, the first, second, and third portions 154, 156, 166, respectively, define the outer surface 168 including corresponding outer surface portions 168a, 168b, and 168c. Similarly, the first, second, and third portions 154, 156, 166, respectively, define the inner surface 170 including corresponding inner surface portions 170a, 170b, 170c. In one embodiment, a portion of the inner surface 170 is treated with a form of energy, such as with a laser beam as described above, to define a treated region 173. As shown in FIGS. 26 and 27, the treated region 173 may encompass or be coextensive with the entire inner surface 170. Alternatively, the treated region 173 may be coextensive with one or more of the inner surface portions 170a, 170b, 170c. Thus, the treated region 173 may be disposed along only any portion of or a combination of the first, second, and third inner surface portions 170a, 170b, 170c and need not necessarily be coextensive with the inner surface 170. By way of example, each of the inner surface portions 170a and 170b, and not including the inner surface portion 170c, may form the treated region 173. Other configurations and locations of the treated regions 173 are possible and are not limited to the locations along the inner surface of the body 152 as disclosed herein. Moreover, it will be appreciated that the treated region 173 may extend into the body 152 a certain depth towards the outer surface 168, as is described below.

Similar to the treated regions described above with regard to the archwire, band, and crown, the treated region 173 differs in composition from an untreated region 175 of the base alloy composition. The treated region 173 therefore has different material characteristics similar to that set forth above. Namely, the composition of the treated region 173 may include a shift in the transition temperatures, such as, but not limited to a shift in $A_f$ relative to the untreated region 175. Therefore, like the crown and the band, described above, the body 152 is a monolithic piece of SMA that, after being initially formed of a base alloy composition, such as NiTi, is subject to a secondary process by which the alloy composition of a selected portion of the body 152 is modified so as to produce treated region 173.

During installation, in one embodiment, the stop 150 is placed onto an archwire by passing the archwire through the opening 164 to coincide with the axis 162. Once in position, the body 152 is secured around the archwire so that the opposing lips 158, 160 approach one another and the inner surface 170 comes into frictional contact with the archwire. In this regard, the treated region 173 may assist in preventing displacement of the stop 150 from the archwire once placed thereon and may improve the long-term frictional engagement between the stop 150 and the archwire. Specifically, the treated region 173 is configured to plastically deform once the stop 150 transitions from the opened position (FIG. 26) to the closed position (FIG. 27). Similar to the treated regions 126 and 146 of the crown 110 (FIG. 24) and band 132 (FIG. 25), respectively, described above, the treated region 173 may exhibit a greater ductility than the untreated region 175, or a greater ductility than the rest of the C-shaped body 152, at temperatures at or near the temperature of the human body. The increased ductility allows the first treated region 173 to more readily plastically deform and maintain the installed position when the treated region 173 is compressed against the archwire and heated to the temperature of the oral cavity. The plastic deformation, due to a larger fractional percentage of martensite in the treated region 173, is advantageous in that it may allow at least part of the inner surface 170 to conform to the shape of the archwire, thereby creating a more intimate surface-to-surface contact between the stop 150 and the archwire that is maintained at the temperature of the oral cavity. Once deformed, at least portions of the treated region 173 maintain the deformed configuration throughout orthodontic treatment. In contrast, the untreated region 175 may contain more austenite at the operating temperature. In one embodiment, the untreated region 175 may have superelastic characteristics so that the untreated region 175 is configured to absorb impact during treatment. In one embodiment, as is described below, the stop 150 does not need to be fastened or crimped on the archwire with a tool.

Figure 28:
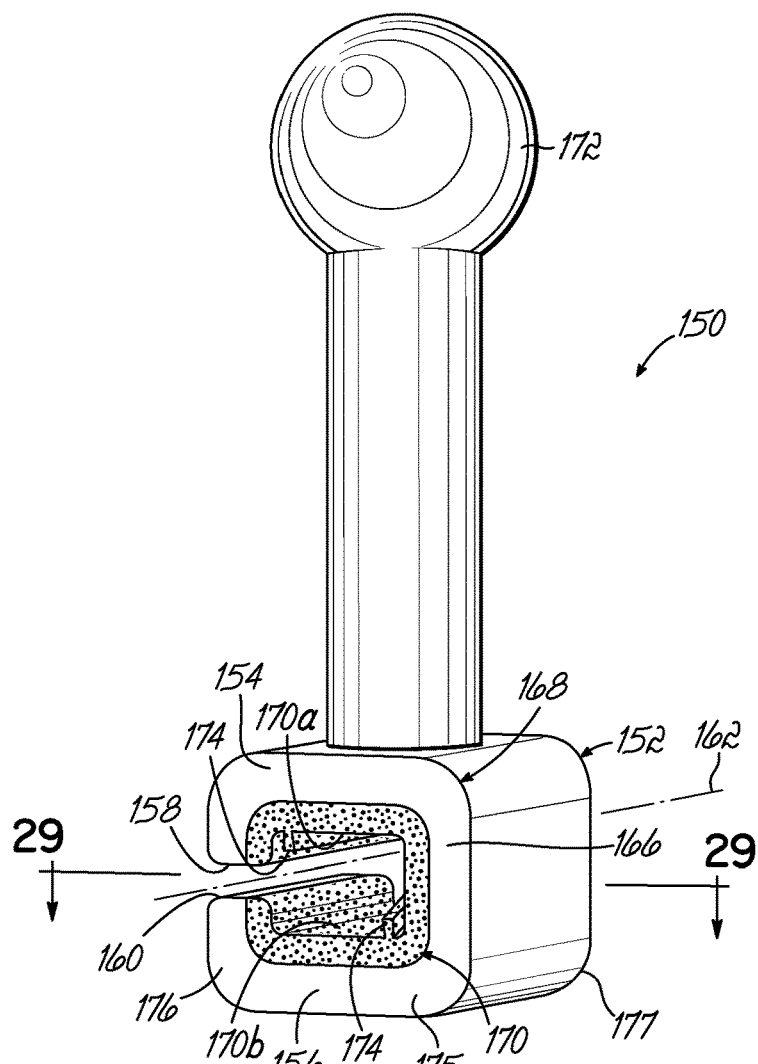
FIG. 28 is a perspective view of one embodiment of a hook according to the present invention.
Figure 29:
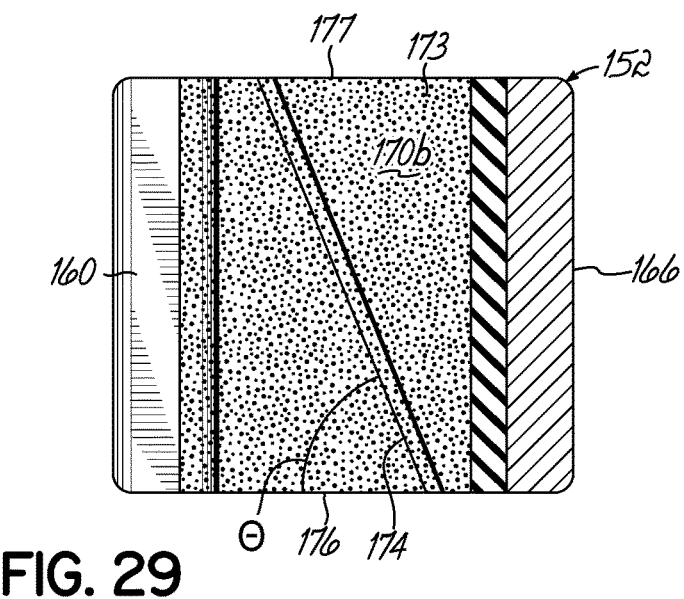
FIG. 29 is a cross-sectional view of the hook of FIG. 28 taken along section line 29-29.

The inner surface 170 may include features to further enhance the friction fit between the stop 150 and the archwire. To that end, in one embodiment shown in FIGS. 28 and 29, the inner surface 170 includes opposing inner surface portions 170a, 170b having ribs 174 extending in the direction of the axis 162, and situated transverse to each of the lips 158, 160. In one embodiment, the opposing ribs 174 are transverse to one another. The ribs 174 extend between a first peripheral edge 176 and a second peripheral edge 177 at an angle $\Theta$ relative to the peripheral edge 176. As shown, $\Theta$ may be approximately 60°. However, in other embodiments, $\Theta$ may be between about 30 and about 90°. Moreover, there may be multiple ribs 174 on the inner surface portions 170a, 170b. For example, there may be 2 or more ribs extending from the one or both of the inner surface portions 170a, 170b that are situated parallel to one another. Alternatively, the ribs could be situated transverse to one another such that they essentially form an X-shaped or lattice-shaped pattern.

During installation, the configuration of the ribs 174 places high unit pressures on the ribs 174 by contact with the archwire and thus the ribs 174 are more likely to deform. Deformation of the ribs 174 may further enhance the fit, and thus the friction, between the stop 150 and the archwire that extends generally coincident with the axis 162.

Figure 30:
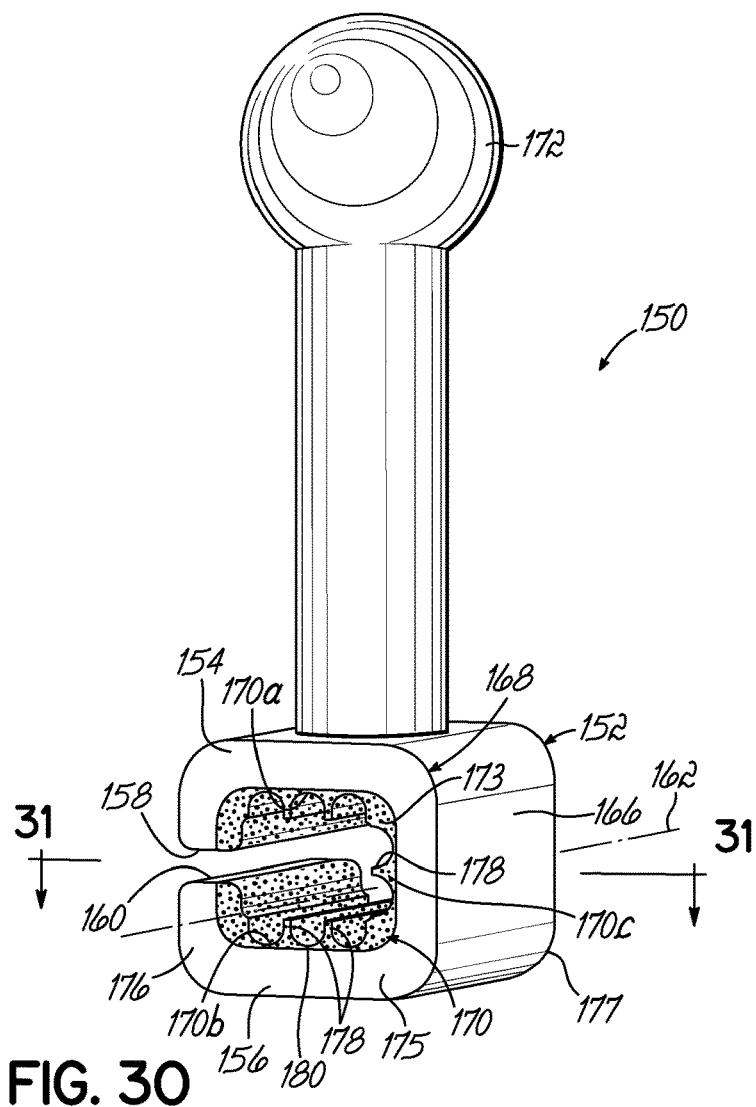
FIG. 30 is a perspective view of one embodiment of a hook according to the present invention.
Figure 31:
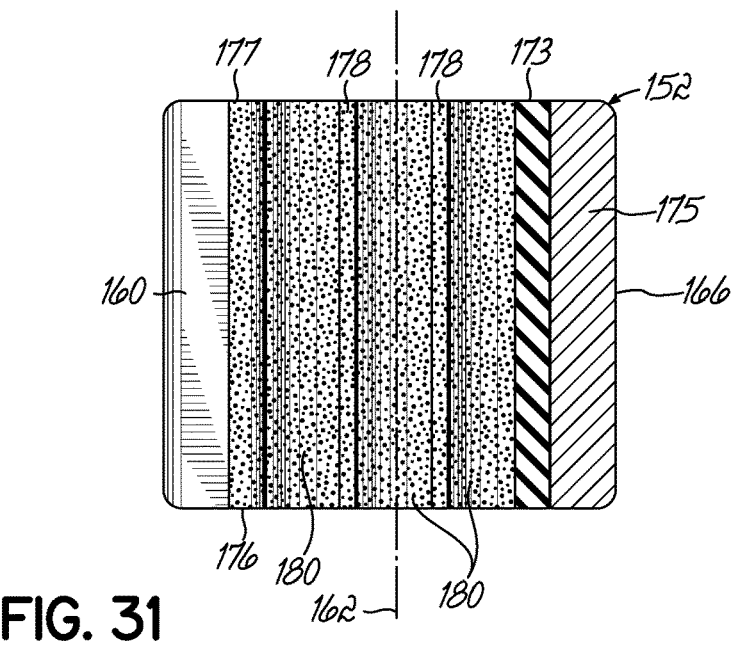
FIG. 31 is a cross-sectional view of the hook of FIG. 30 taken along section line 31-31.

In one embodiment, as shown in FIGS. 30 and 31, each of the inner surface portions 170a, 170b, 170c includes at least one rib 178. The ribs 178 differ in configuration from the ribs 174 shown in FIGS. 28 and 29, but may form a portion of the treated region 173 and so the ribs 178 may function in a similar manner as the ribs 174. As shown in FIGS. 30 and 31, the ribs 178 are in part defined by equally spaced, semicircularly shaped voids 180 or cutouts along the width of the body 152. As shown, the ribs 178 of the first and second inner surface portions 170a, 170b extend toward the axis 162 and are situated transverse to the peripheral edge 176. For example, the ribs 178 of the first and second inner surfaces 170a, 170b are perpendicular to the peripheral edge 176 and oppose one another across the axis 162. The rib 178 of the third portion 166 extends toward the axis 162 and is parallel to the axis 162. As shown, the first and second portions 154, 156 each include two ribs 178, while the third portion 166 includes one rib 178. However, in other embodiments, there may be the same or a different number of ribs 178 on each of the first, second, and third portions 154, 156, 166, respectively.

Figure 32:
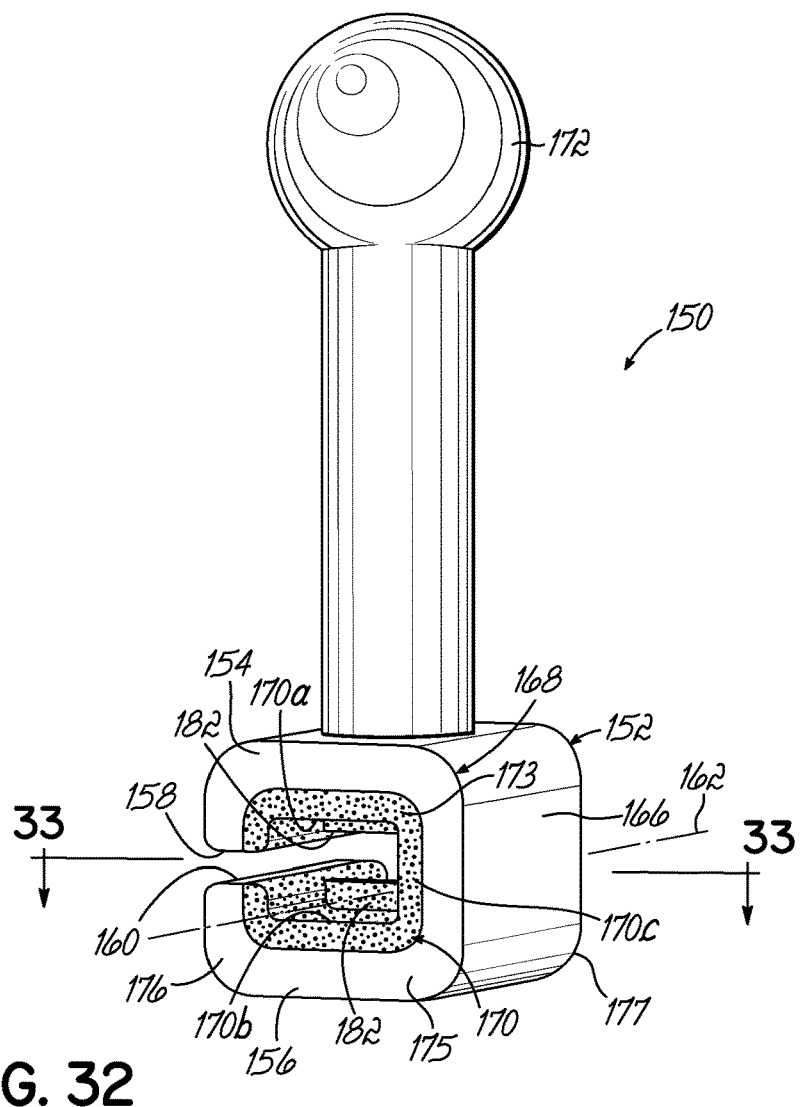
FIG. 32 is a perspective view of one embodiment of a hook according to the present invention.
Figure 33:
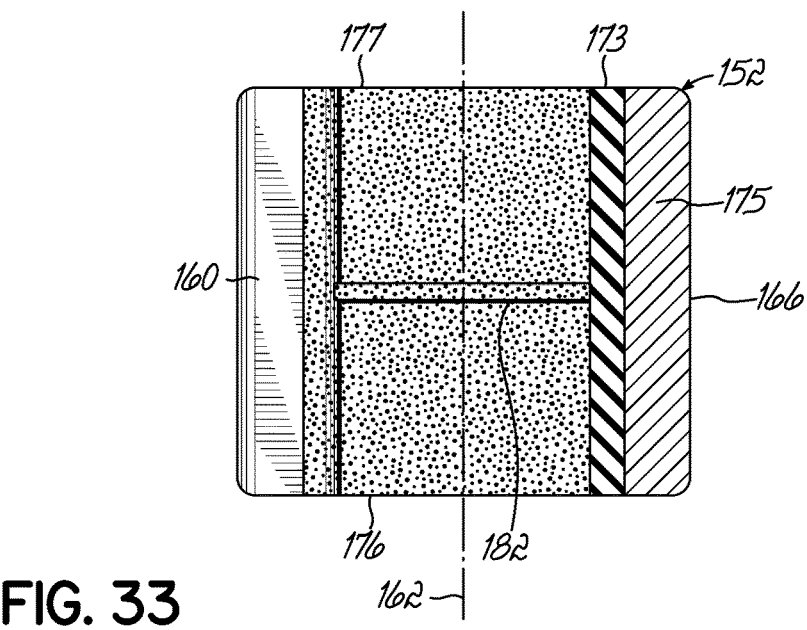
FIG. 33 is a cross-sectional view of the hook of FIG. 32 taken along section line 33-33.

In one embodiment, as shown in FIGS. 32 and 33, the stop 150 includes a pair of ribs 182. Unlike the ribs 174, 178 each rib 182 shown in FIGS. 32 and 33 is transverse to (e.g., is perpendicular to) the axis 162 between the third inner surface portion 170c and the lips 158, 160 or are oriented cross-wise to the axis 162. Ribs 182 are generally parallel with the peripheral edge 176 of stop 150 and have a generally rectangular cross-section, as viewed from above (shown best in FIG. 33). In other embodiments, there may be more than one rib 182 in each of the first and second inner surface portions 170a, 170b. Moreover, the ribs 182 may include different shapes and are not limited to having generally rectangular cross-sections.

As described above, the stop 150 is configured to be placed on an archwire. Consequently, the stop 150 has an opened position (FIG. 26) and a closed position (FIG. 27). In one embodiment, the stop 150 is in a relaxed, normal state in the closed position and is able to be transitioned from the closed position to the opened position. Installation of the stop 150 may include forcibly separating the first and second portions 154, 156 using a tool (not shown), such as dental pliers. Due to its shape memory properties, prying apart the first and second portions 154, 156 results in the stop 150 being in a deformed configuration. Once the clinician positions the stop 150 in the appropriate position on the archwire, the stop 150 returns to the closed position as the temperature of the stop 150 approaches the operation temperature, which may be at or near normal oral temperature of the human mouth. In this embodiment, the stop 150 is configured to move from the opened position to the closed position without mechanical input, such as without crimping.

Figure 34A:
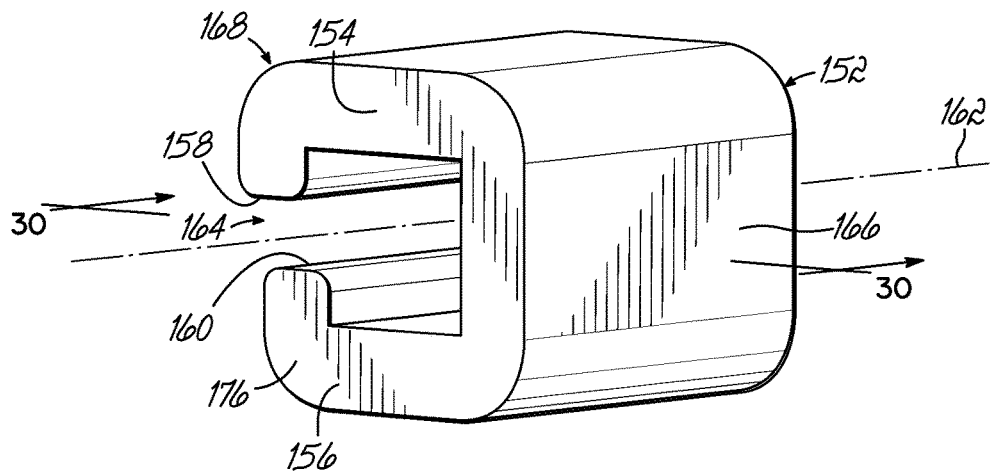
FIGS. 34A-34C are perspective views of a stop according to one embodiment of the invention in various stages of opening/closing.
Figure 34B:
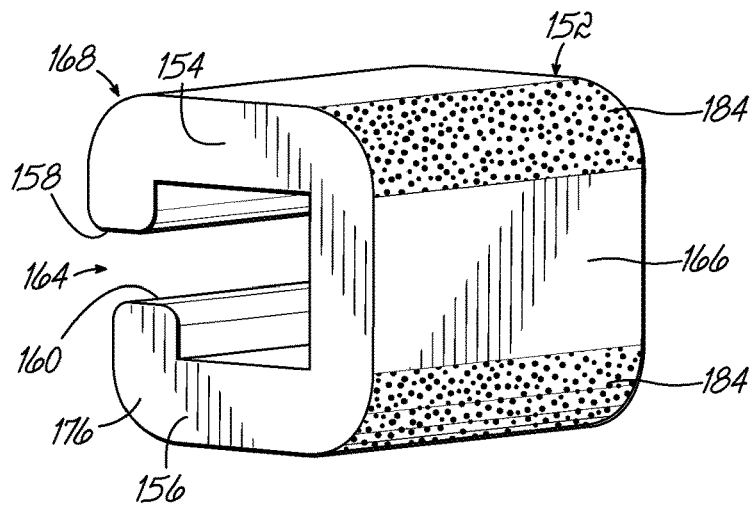
Figure 34C:
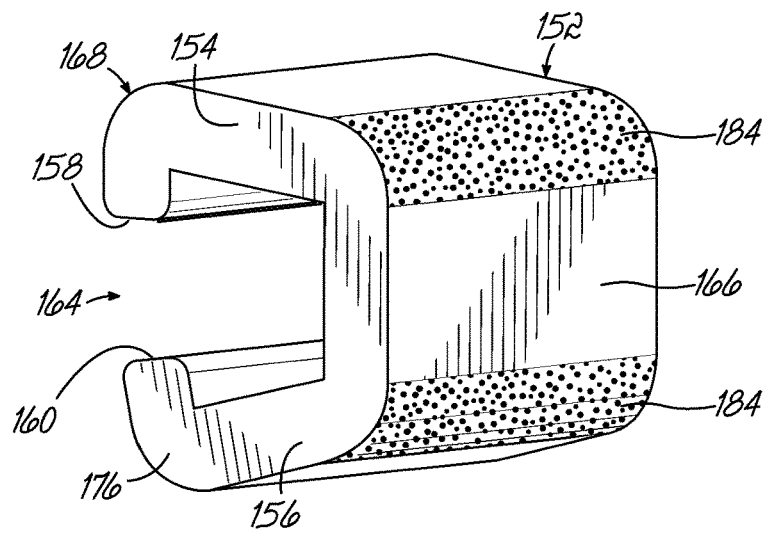

To that end and with reference to FIGS. 34A-34C, the stop 150 may be manufactured by machining, for example, by electric discharge machining (EDM), a base alloy composition made of an SMA alloy into the C-shaped configuration of the body 152, as shown in FIG. 34A without the hook 172. After machining, an outer surface portion 168 of at least one of the first, second, or third portion 154, 156, 166 is treated with a form of energy, such as a laser beam, to form one or more treated regions 184, as shown in FIGS. 34B and 34C. As shown, the treated regions 184 are located on the outer surface portion 168 at the transition or corners between the first and third portions 154, 166, and the second and third portions 156, 166, respectively. In one embodiment, treating with a form of energy removes selected constituents of the base alloy composition so as to form regions 184 that are depleted in at least one metallic element from the base alloy composition. The treated regions 184 may exhibit shape memory properties. In one embodiment, the $A_f$ is approximately 30° C. After selectively treating the body 152 to thereby define the treated regions 184 (FIG. 34B), the body 152 may be deformed mechanically into an opened position (FIG. 34C), whereby the first and second portions 154, 156 are moved away from one another to accept an archwire through the opening 164. Though not shown, deformation of the body 152 may occur primarily or solely in the treated regions 184. The stops 150 may then be packaged for shipment to the orthodontists' office for use.

Once the body 152 is deformed into an opened position (FIG. 34C) prior to installation, the body 152 remains in the opened position until being subjected to an increase in temperature to at least an operating temperature, for example, the oral temperature. At temperatures near or above the operating temperature, the body 152 recovers its normal or undeformed configuration (FIG. 34B) or closed position. Upon closing, the inner surface portion of the body 152 engages the archwire. Essentially, once placed in the patient's mouth, the stop 150 will close such that the first and second portions 154, 156 move towards one another without a mechanical input, such as crimping. It will be appreciated that the orthodontist may remove the stop 150 by forcing apart the ledges 158, 160 with a scalar or pliers as is known in the art. The orthodontist may also cool the stop 150 prior to removal to increase the proportion of martensite in the regions 184, which may facilitate removal of the stop 150.

Figure 35:
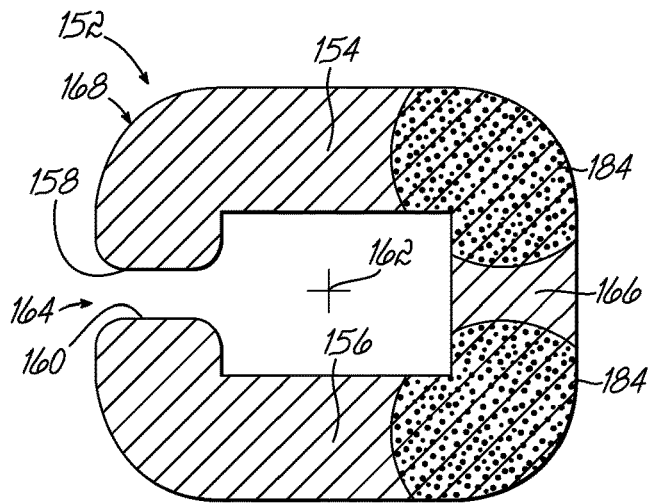
FIGS. 35-37 are cross-sectional views taken along section line 35-35 of the stop shown in FIG. 34A depicting exemplary treated regions according to embodiments of the present invention.

With reference now to FIG. 35, in one embodiment, the treated regions 184 may encompasses the through-thickness of the body 152. In other words, the treated region 184 may form portions of both the inner and outer surfaces 168, 170. In the exemplary embodiment shown, the secondary treated regions 184 may be located at the junction between the first and third portions 154, 166 and the second and third portions 156, 166, respectively, such that the third portion 166 includes parts of two separate treated regions 184.

Figure 36:
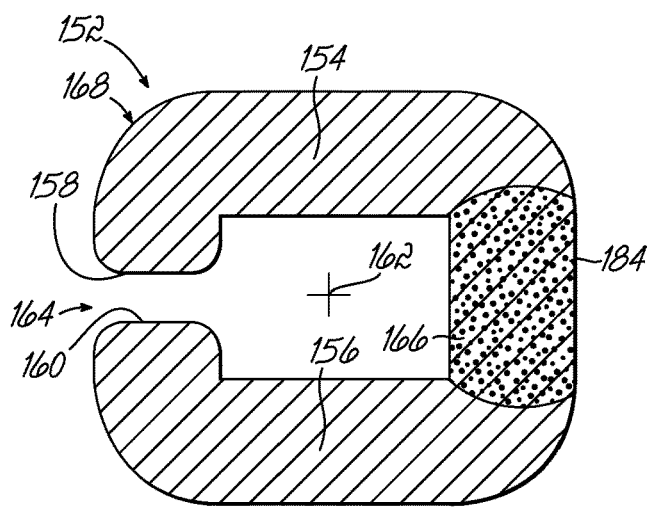

In an alternative embodiment, as shown in FIG. 36, the treated region 184 is located solely within the third portion 166. It will be appreciated however that a small portion of the treated region 184 may also be located on or at the first or second portions 154, 156. Similar to that shown in FIG. 35, in the embodiment shown in FIG. 37, the treated regions 184 may extend the entire through thickness of the body 152. However, the secondary treated regions 184 may be alternatively configured such that they only traverse a portion of the through-thickness of the body 152. For example, as shown in FIG. 38, the treated region 184 may penetrate only a portion of the thickness of the body. In the embodiment shown, "d" is the depth of the secondary treated region 184 and "D" is the overall depth or thickness of the stop 150 measured perpendicular to a tangent along the outer surface of the stop 150. The ratio d/D is approximately 0.63. The treated region 184 may therefore extend through about 63% of the thickness of the body 152.

Figure 37:
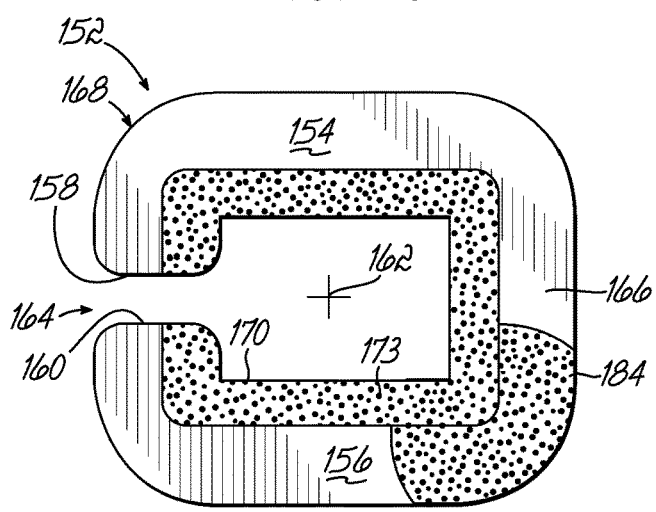
Figure 38:
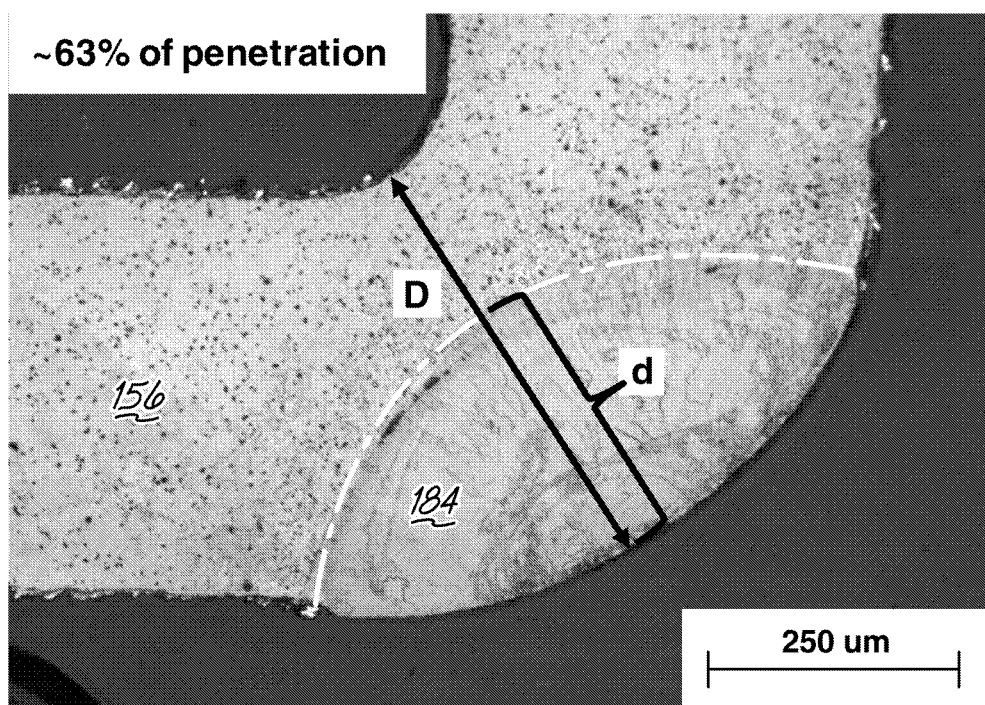
FIG. 38 is a SEM micrograph of a cross section of an exemplary stop according to one embodiment of the invention.

With reference now to FIG. 37, in one embodiment, the body 152 may include the treated region 173 defining the inner surface 170, as is described above with reference to FIGS. 26-33, and the treated region 184, as described above with reference to FIGS. 35 and 36, forming a portion of the outer surface 168. According to at least this embodiment, when the body 152 is engaged with an archwire and then subject to temperatures at or near the operating temperature, the body 152 may close around the archwire due to the to the shape memory characteristics attributed to the treated region 184. During closing, the treated region 173 may plastically deform to enhance the surface-to-surface friction between the archwire in the treated region 173. It will be appreciated that the compositions of the alloy in each of the treated regions 173 and 184 may not be the same. In one embodiment, the $A_f$ of the retreated region 173 is higher than the $A_f$ of the treated region 184, which may, in turn, be higher than the $A_f$ of the base alloy composition.

Example

Figure 39:
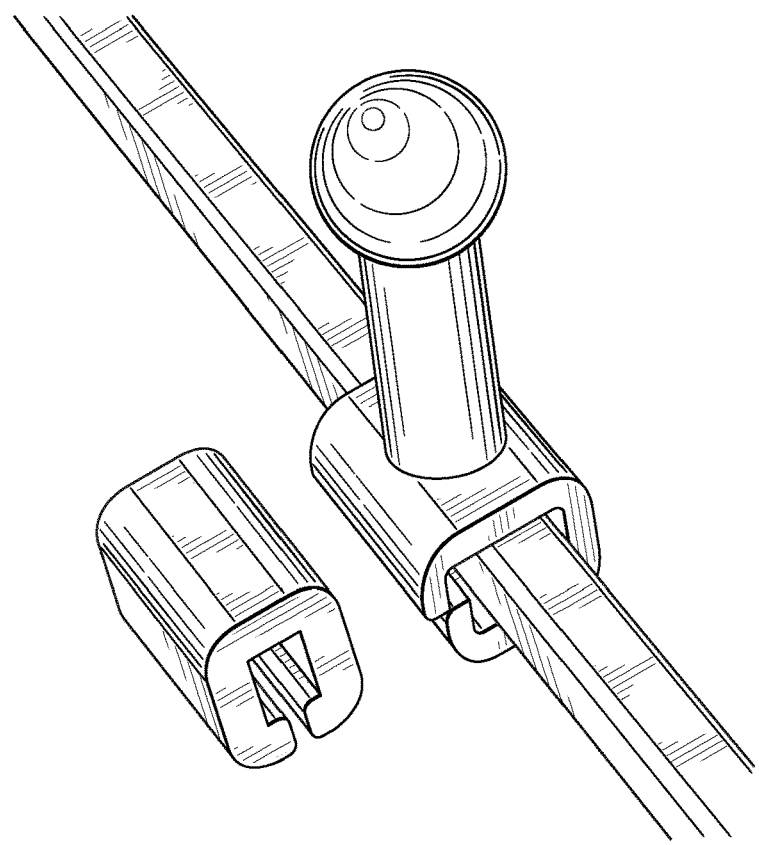
FIG. 39 is a drawing representation of a photograph of a stop and a hook according to embodiments of the present invention.
Figure 40:
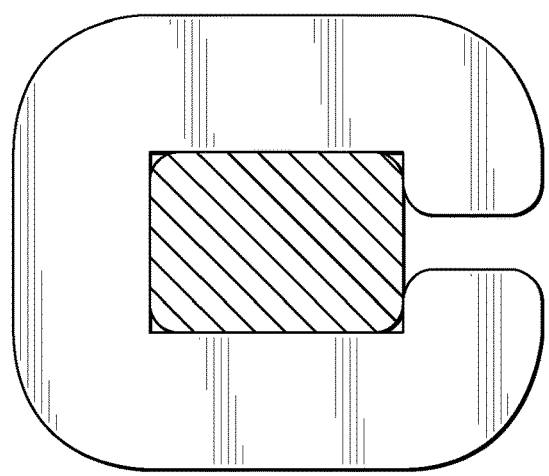
FIG. 40 is a drawing representation of a photograph of a stop according to one embodiment of the invention.
Figure 41:
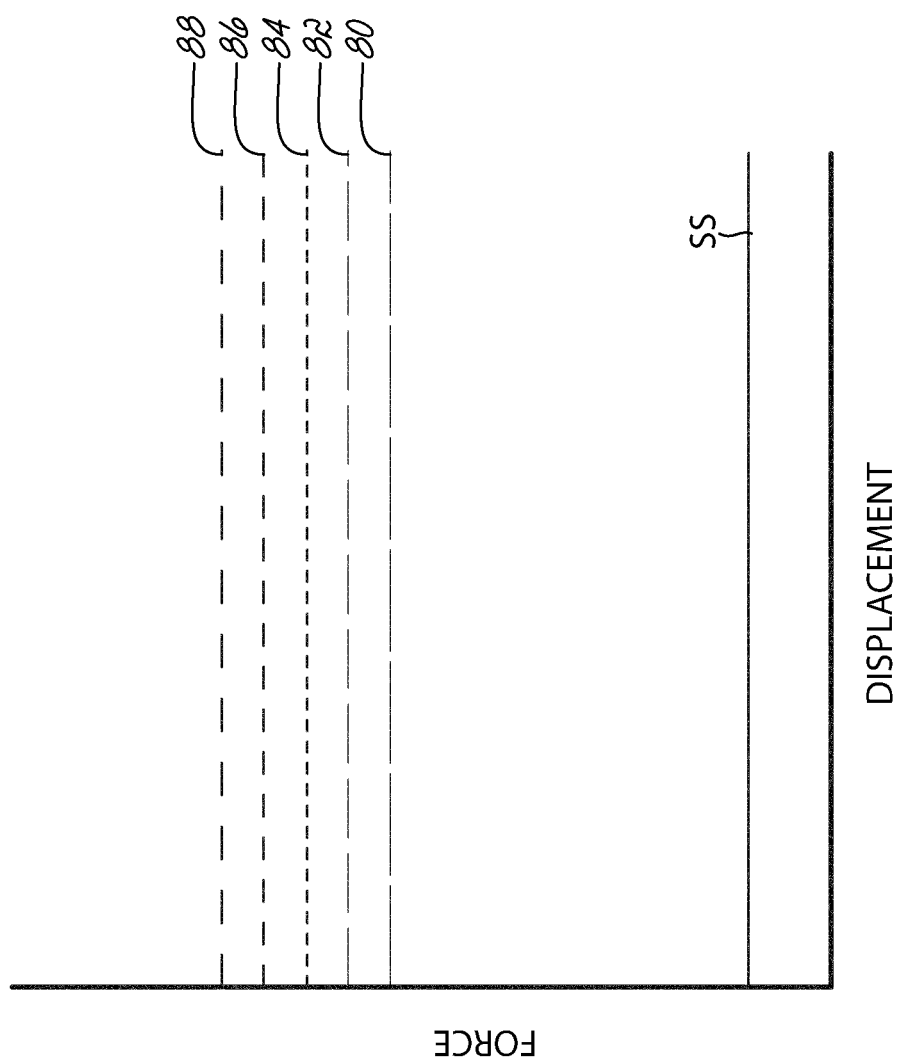
FIG. 41 is a theoretical graph of displacement versus force for hooks according to embodiments of the invention.

A stop and hook shown in FIGS. 39 and 40, for example, are treated with a laser for a predetermined number of pulses. For example, the base alloy composition of a NiTi hook may be processed with the Fiber laser, described above. By way of example, the power may be varied between 30% and 80% with a pulse duration of about 10 µs. Dwell time and overlap may also be varied. In this way, customized stops/hooks with controlled variation in gripping or clamping capability may be produced. With reference to FIG. 41, a stop/hook according to one embodiment of the invention may be produced such that the load at which sliding commences is predetermined. In other words, the magnitude of the friction between the archwire and the stop may be controlled. This may be achieved by controlling the clamping force. An increase in the clamping force results in an increase in the friction.

As is depicted in FIG. 41, and without being bound by theory, the force at which the stop begins to slide may be adjusted by laser treating the appliance, such as the stop or hook (shown in FIGS. 26 and 34A, respectively, for example). The treated stop/hook may then be assembled onto an archwire as described above. Once affixed, a load may be applied to the stop/hook and the force at which the stop/hook begins to slide along the archwire is measured. An Instron machine and clamping system may be utilized, as can be appreciated by those of ordinary skill in the art, to measure the force at which sliding commences.

The results of the testing may be consistent with that illustrated in FIG. 41. As shown, variations in treatment of individual stops/hooks may provide variations in the force to initiate sliding as indicated at 80, 82, 84, 86, and 88. The force required to initiate sliding may increase or decrease relative to the base composition and may be greater than the force required to initiate sliding of a stainless steel stop/hook, as is indicated at "SS" in FIG. 41. For example, a stop with the base alloy composition may be indicated at 80. With laser treatment, the stop may require a force to initiate sliding as indicated by line 82. Further processing may provide a stop that may begin sliding at 84. Still further processing may provide a stop that begins sliding at 86, and still further processing relative to the stop indicated by line 86 may produce a stop that begins sliding at line 88. The reverse relationship between processing and sliding force may also be possible for a given alloy composition.

In this regard, and by way of example, a stop of a base alloy composition may begin sliding according to line 88. Processing with a laser as described herein may reduce the gripping capability of the stop so that it begins sliding at a lower force such as that indicated by line 86. Additional processing may produce stops with consecutively lower force at which sliding is initiated, such as indicated at lines 84, 82, and 80. It will be appreciated that the composition of the base alloy may determine whether the gripping force may be increased or decreased from the base alloy composition with laser processing. In any case, however, the stop/hook may be processed to target a desirable threshold force at which sliding is initiated. Advantageously, clinicians may specify a force at which the stop/hook begins to slide on the archwire. This may be to maximize patient comfort or for another reason.

Self-Ligating Orthodontic Brackets

Self-ligating brackets are known in the art. However, current self-ligating brackets are often multi-piece assemblies. For example, current metallic and ceramic self-ligating brackets are often assembled from at least two pieces, namely at least a bracket body that defines an archwire slot and a ligating member, such as a movable clip or slide that has an opened position allowing insertion of the archwire and a closed position that captures the archwire in the archwire slot. The clip or slide moves relative to the bracket body. Such brackets may be costly, due in part to the complexity of manufacturing the tight tolerances between pieces that is required to consistently fit multiple small pieces together. Further, two-piece assemblies may present a risk of harm to the patient due to swallowing or aspiration of the separate pieces. It is therefore desirable to solve these and other known problems of self-ligating orthodontic brackets.

Figure 42:
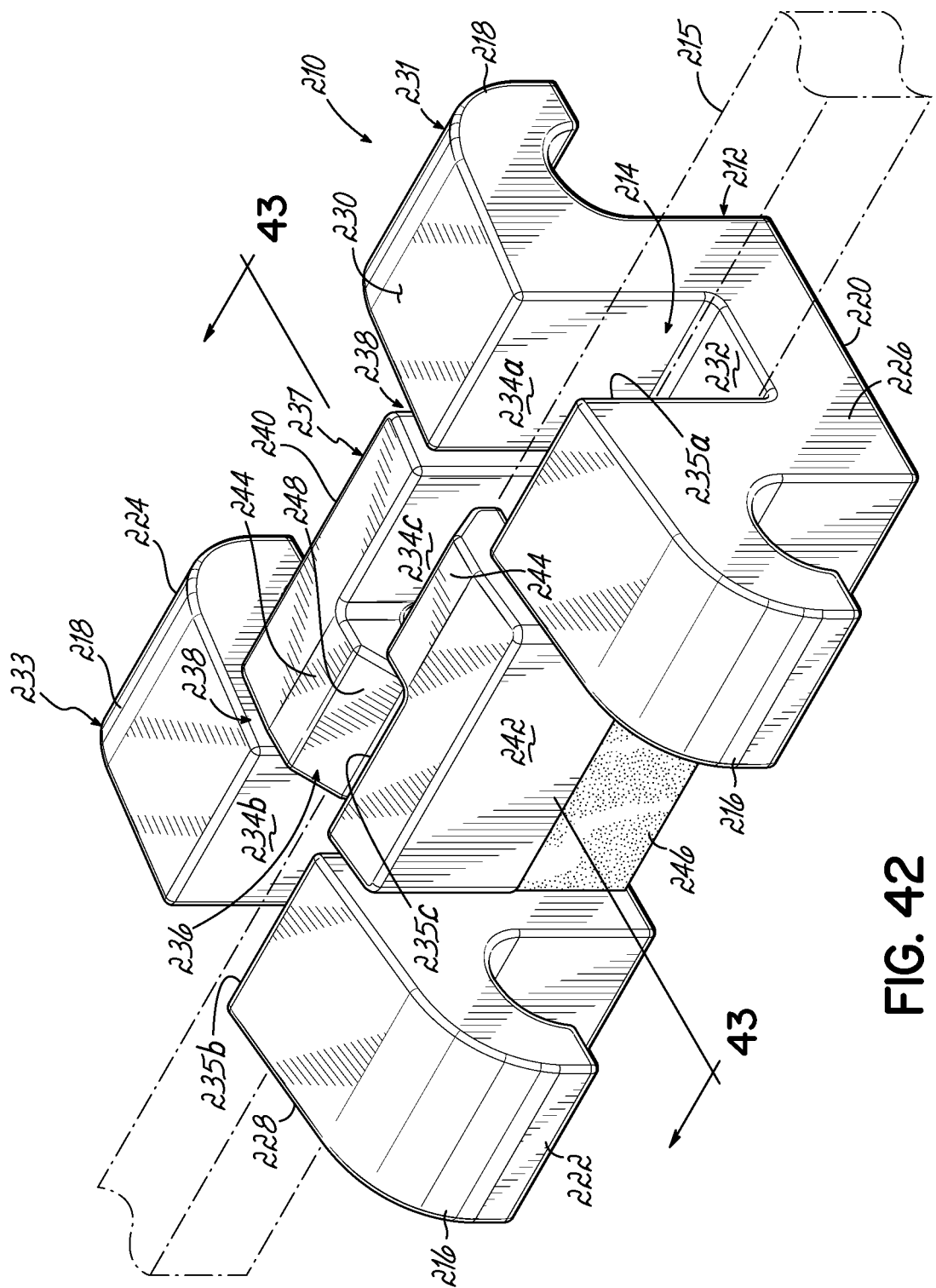
FIG. 42 is a perspective view of a self-ligating orthodontic bracket according to another embodiment of the invention.

To these and other ends, one embodiment of a self-ligating orthodontic appliance, as shown in FIG. 42, includes a bracket 210, which is a single, unitary member that has an integral ligating member. In particular, the bracket 201 comprises a bracket body 212 that defines an archwire slot 214. The bracket body 212 is configured to receive archwire 215 for applying corrective forces to the tooth. As is described in detail below, the bracket 210 is made of a SMA having a base alloy composition with one or more regions treated with a form of energy to change the composition of those regions relative to the base alloy composition of the SMA. The transition temperatures of the treated regions may differ from the transition temperatures of the base alloy composition. As a result, a change in temperature may produce a different phase change in the treated regions relative to the base alloy composition or allow portions of the bracket 210 exhibit superelastic and/or shape memory characteristics while other portions do not exhibit these properties or exhibit a different property.

In the embodiment shown, the body 212 has opposing occlusal and gingival tie wings 216, 218, respectively, for receiving one or more ligatures (not shown), as is known in the art. While tie wings 216, 218 and ligatures are described herein, it is anticipated that in some instances the tie wings 216, 218 and ligatures may be unnecessary.

The embodiments described herein, unless otherwise indicated, are described herein using a reference frame with the bracket 210 attached to a labial surface of a tooth on the upper jaw. Consequently, as used herein, terms such as labial, lingual, mesial, distal, occlusal, and gingival used to describe bracket 210 are relative to the chosen reference frame. The embodiments of the invention, however, are not limited to the chosen reference frame and descriptive terms, as the orthodontic bracket 210 may be used on other teeth and in other orientations within the oral cavity. For example, the bracket 210 may also be located on the lower jaw or mandible and be within the scope of the invention. Those of ordinary skill in the art will recognize that the descriptive terms used herein may not directly apply when there is a change in reference frame. Nevertheless, the invention is intended to be independent of location and orientation within the oral cavity and the relative terms used to describe embodiments of the orthodontic bracket are to merely provide a clear description of the examples in the drawings. As such, the relative terms labial, lingual, mesial, distal, occlusal, and gingival are in no way limiting the invention to a particular location or orientation.

When the bracket 210 is mounted to the labial surface of a tooth carried on the patient's upper jaw, the body 212 has a lingual side 220, an occlusal side 222, a gingival side 224, a mesial side 226, a distal side 228, and a labial side 230. The lingual side 220 of the body 212 is configured to be secured to the tooth in any conventional manner, for example, by an appropriate orthodontic cement or adhesive or by a band around an adjacent tooth (not shown).

With reference to FIG. 42, in one embodiment, the body 212 includes a mesial portion 231, a distal portion 233, and a central portion 237. A base surface 232 and a plurality of opposed mesial, distal, and central surfaces 234a-c, 235a-c that correspond to the mesial portion 231, the distal portion 233, and the central portion 237, respectively, project labially from the base surface 232 and collectively define the archwire slot 214 in the body 212. The archwire slot 214 extends in a mesial-distal direction from mesial side 226 to distal side 228 of the bracket body. The central portion 237 is spaced from each of the mesial portion 231 and the distal portion 233 by spaces 238 (i.e., gaps) between the mesial surfaces 234a, 235a and corresponding central surfaces 234c, 235c and between the distal surfaces 234b, 235b and the corresponding central surfaces 234c, 235c. The mesial portion 231 and the distal portion 233 are connected by bridges 245 corresponding to the spaces 238, as is shown best in FIG. 44. The bridges 245 essentially form a portion of the base surface 232 so as to form a continuous base surface 232 from the mesial portion 231 through the distal portion 233.

Figure 43A:
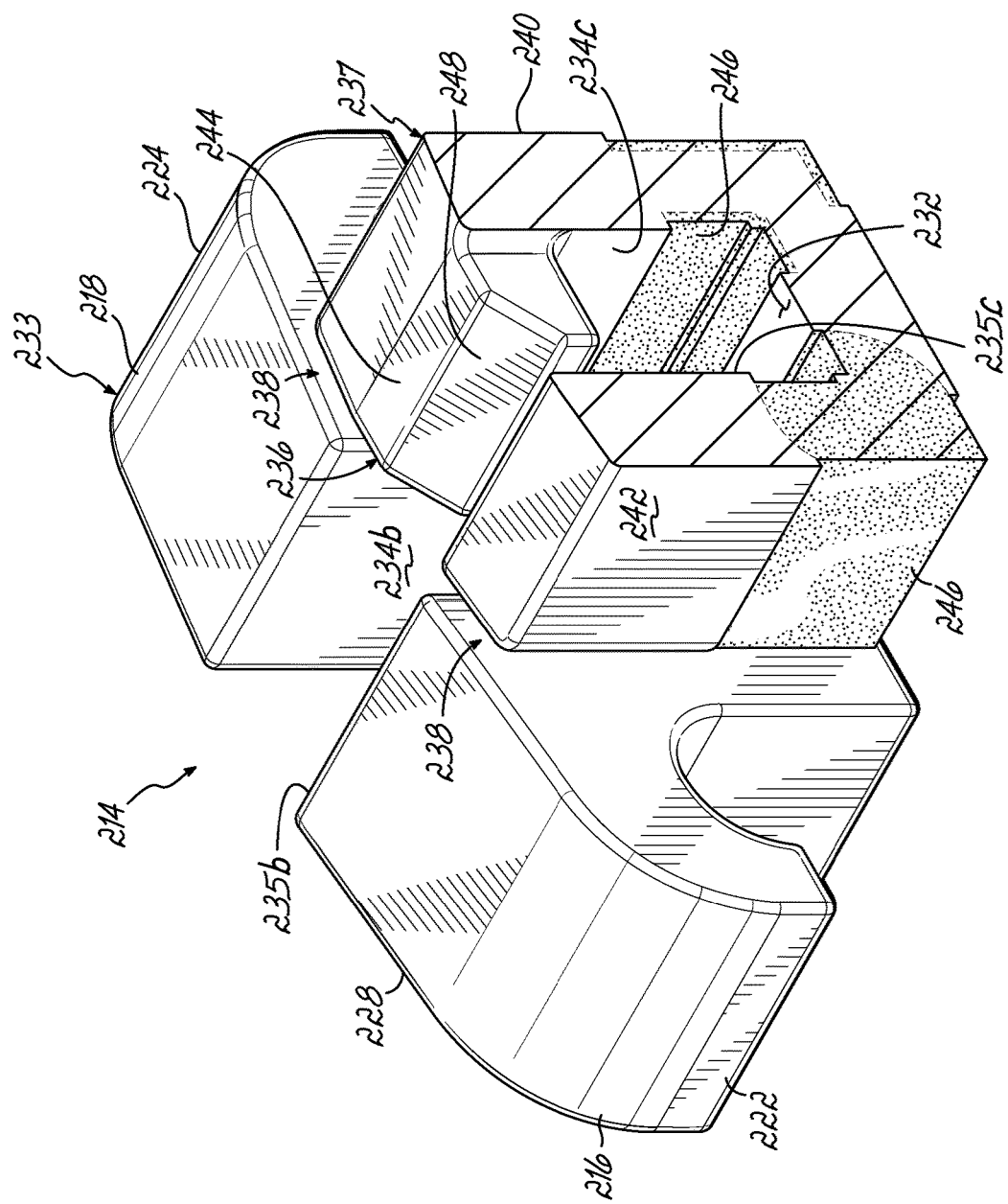
FIG. 43A is a cross-sectional view of the orthodontic bracket of FIG. 42 taken along section line 43A-43A depicting an integral ligating member in the closed position.

With reference now to FIGS. 42 and 43A, in one embodiment, the central portion 237 includes the integral ligating member in the configuration of a ligating portion 236. In this regard, in the exemplary embodiment shown, the central portion 237 includes a gingival wall 240 and an occlusal wall 242 that respectively define the central surfaces 243c and 235c of the archwire slot 214. At least one shoulder or projection 244 extends from one of the gingival wall 240 or from the occlusal wall 242. However, it will be appreciated that the projection 244 may extend from each of the gingival wall 240 and the occlusal wall 242, as shown in FIG. 42. The projection 244 extends outwardly from the gingival wall 240 or the occlusal wall 242 so as to define a labial-most boundary of the archwire slot 214 when the projection 244 is in a closed position (FIG. 43A). In the embodiment shown in FIGS. 42 and 43A, the projections 244 may be adjacent one another in an opposing relationship in the mesial-distal direction with each extending across a substantial portion of the archwire slot 214 a distance sufficient to prevent or at least resist removal of an archwire from the slot 214.

Figure 43B:
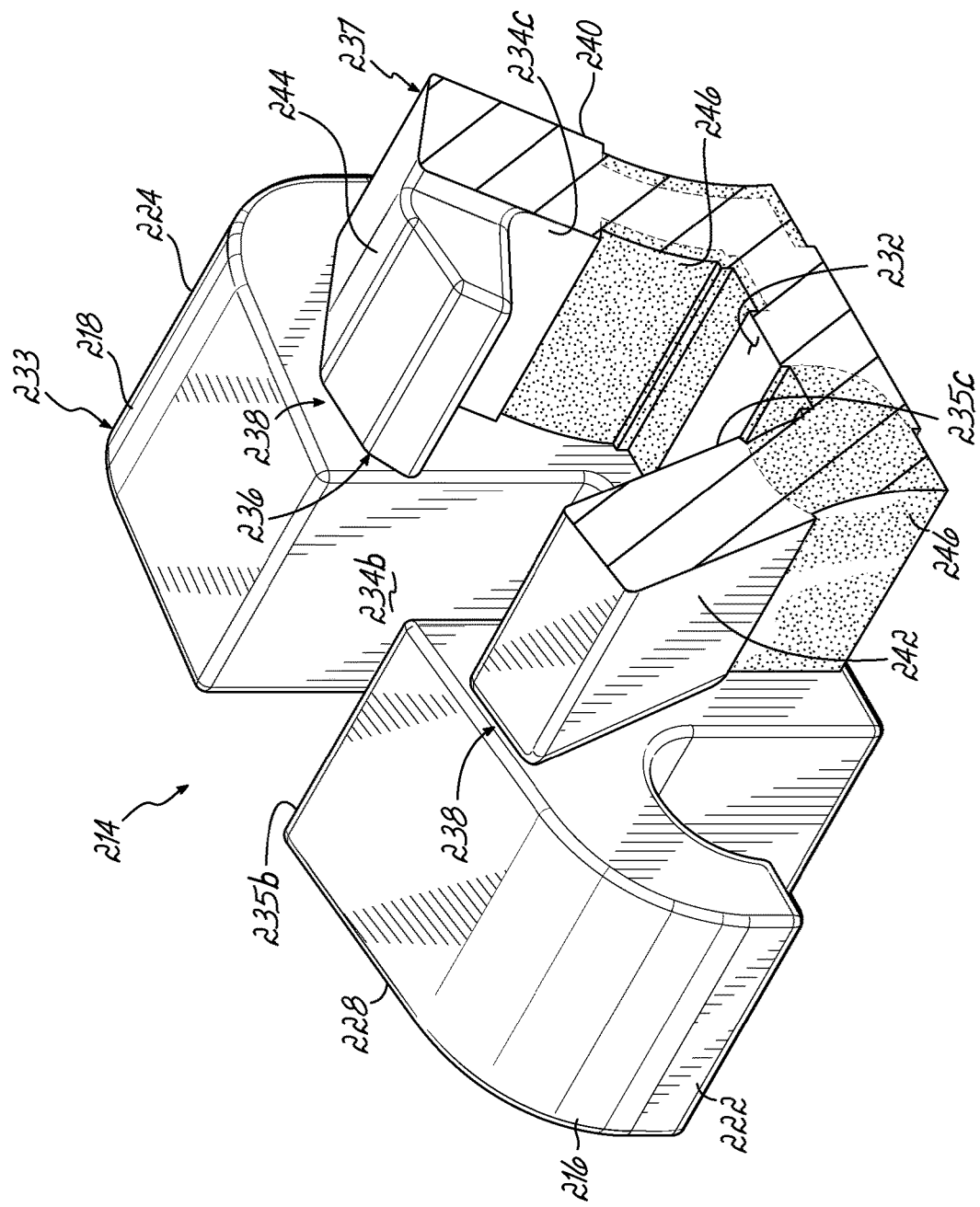
FIG. 43B is a cross-section view of the orthodontic bracket of FIG. 42 similar to FIG. 43A but depicting the integral ligating member in the opened position.
Figure 44:
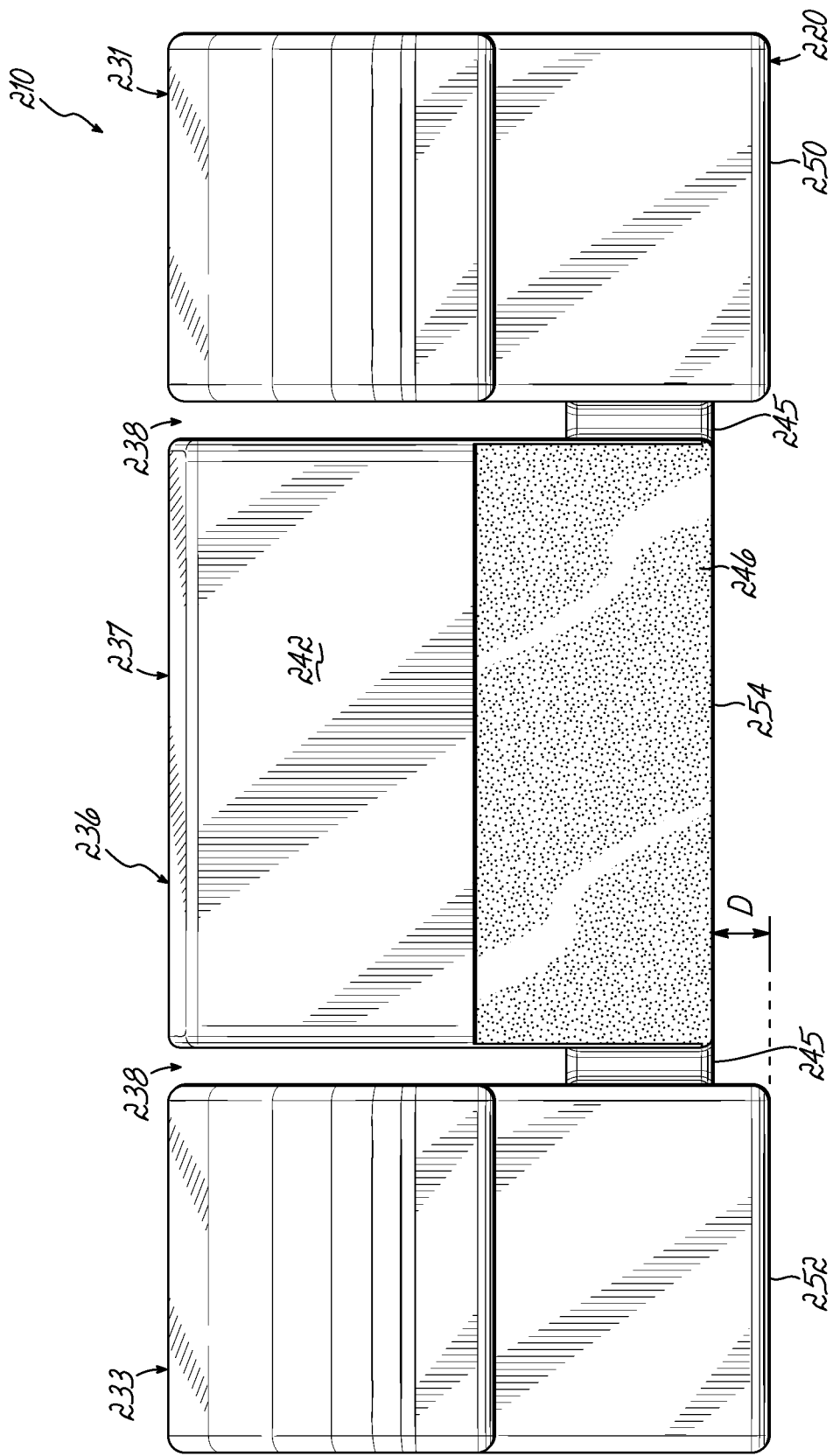
FIG. 44 is an elevational view of the orthodontic bracket of FIG. 42.

With continued reference to FIG. 43B, the central portion 237, specifically the walls 240 and 242, have an opened position, in which the archwire 215 (FIG. 42) may be inserted past the projections 244 and into the archwire slot 214, and a closed position (FIG. 43A), in which the projections 244 prevent inadvertent removal of the archwire from the archwire slot 214. The spaces 238 allow the walls 240, 242 to move towards and away from one another between opened and closed positions, as described below. In addition, and with reference to FIG. 44, the lingual side 220 of the bracket body 212 may include a mesial surface portion 250 along the mesial portion 231 of the bracket body 212 and a distal surface portion 252 along the distal portion 233 of the bracket body 212. Each of the mesial surface portion 250 and the distal surface portion 252 may be configured to be secured to a pad (not shown) or other surface prior to being bonded to a tooth. As shown in FIG. 44, the central portion 237 includes a central surface portion 254 that is offset by a dimension, D, labially away from a plane defined by the mesial and distal surface portions 250, 252. As is described below, the offset of the central surface portion 254 may provide clearance between the walls 240, 242 when either or both of the walls are moved to an opened position.

As described above, in one embodiment, a surface portion of the bracket body 212 may be selectively treated with a form of energy, such as a laser beam, so that the surface portion includes a treated region 246 that differs in chemical composition from the base alloy composition of the SMA. The treated region 246 may be formed similar to the treated areas 28 or treated regions 126, 146, 173, and 184, described above, to remove selected metallic elements from that region of the bracket body 212. As indicated at 246 in FIGS. 43A and 43B, part of the base surface 232 and central surfaces 234c, 235c as well as outer surfaces of walls 240, 242 are treated with a form of energy such that they include a different chemical composition than the base alloy composition of the untreated portions of the bracket body 212. As before, it will be appreciated that while the treated regions 246 may be described as included on surface portions, the treated regions 246 may extend beyond the surface and into the body 212 a certain depth or entirely through-thickness (as shown in FIGS. 43A and 43B). Due to the change in the composition of the alloy, the treated region 246 may exhibit a shift in the transition temperatures relative to the transition temperatures of the base alloy composition of the untreated regions of the bracket body 212. The location of the treated regions 246 may provide or at least facilitate the self-ligating feature of the orthodontic bracket 210. While the treated regions 246 are shown as slight depressions so as to be areas of reduced through thickness, it will be appreciated that there may be no discontinuity in the plane of the surface from an untreated region to the treated regions 246.

In one embodiment, the treated regions 246 shown in FIGS. 43A and 43B may impart superelastic properties or shape memory properties into these areas relative to the remaining portions of the bracket body 212. By treating one or more of these regions 246 or by treating the through-thickness of one or both of the walls 240, 242, the regions 246 may behave as a hinge or otherwise provide a region about which one or both of the shoulders or projections 244 may be moved generally away from the archwire slot 214. In particular, as is shown in FIG. 43B, when the projection 244 is moved away from the archwire slot 214, an archwire may be inserted or removed from the archwire slot 214. Once the archwire is inserted into the archwire slot 214, the wall 240 may move back into the closed position so that the projection 244 prevents inadvertent removal of the archwire from the archwire slot 214.

As described above, when the walls 240, 242 are moved outwardly, the offset between the surface 254 and the plane defined by mesial and distal surface portions 250, 252 may provide clearance for the hinge-like action of the regions 246, which may include movement of a portion of the region 246 or a portion of one of the walls 240, 242 into the clearance area, as is generally indicated by D in FIG. 44.

In one embodiment, as is shown in FIGS. 42, 43A, and 43B, the projection 244 may be tapered as indicated at 248. This tapered region 248 of the projection 244 may facilitate insertion of an archwire into the slot simply by pressing the archwire against the tapered region 248 of the projection 244. It will be appreciated that forcing the archwire against the tapered region 248 of the projection 244 may cause the wall 242 to spontaneously flex away from the archwire slot 214 thus allowing the clinician to insert an archwire into the archwire slot 214 without the aid of the tool.

In embodiments in which the regions 246 have superelastic properties, one or more of the regions 246 may include an alloy composition in which the transition temperature $A_f$ is shifted to a different temperature relative to the transition temperature $A_f$ of the base alloy composition of the remainder of the bracket body 212. In one embodiment, $A_f$ of the treated region 246 is shifted to a higher temperature relative to the $A_f$ of the base alloy. Accordingly, with reference to FIG. 43B, one or both of the walls 240, 242 may include a region 246 of superelastic alloy such that flexing the walls 240, 242 in opposing directions outwardly in corresponding occlusal and gingival directions exposes the base surface 232 and does not plastically deform any portion of the wall 240, 242. In one embodiment, by holding the wall 242 such that the projection 244 is in the opened position, the clinician may then insert or remove an archwire from the archwire slot 214. After insertion or removal of the archwire into the archwire slot 214, each of the walls 240, 242 elastically recovers to its initial, closed position. In other words, upon removal of the force needed to hold the projections 244 in the opened position, the treated regions 246 return to the original configuration such that the walls 240, 242 move to their closed positions. Further, the tapered region 248 may facilitate insertion of an archwire into the archwire slot 214 without use of a tool to hold the projection 244 away from the archwire slot in an opened position.

In embodiments in which the regions 246 have shape memory properties, one or more of the regions 246 may include an alloy composition in which the transition temperature $A_f$ is less than the temperature of the oral cavity. Accordingly, with reference to FIG. 43A, one or both of the walls 240, 242 may have a normal, undeformed position as the closed position, that is, with the projections 244 positioned over the archwire slot 214. The clinician may initially cool the bracket 210, specifically the regions 246, prior to installing and/or removing an archwire from the archwire slot 214. Following cooling, the walls 240, 242, specifically the regions 246, may be deformed as the projections 244 are pushed outwardly away from the archwire slot 214 to the opened position shown in FIG. 43B. Once the projections 244 are in the opened position, the clinician may insert and/or remove an archwire from the archwire slot 214. In this embodiment, it may not be necessary for the clinician to hold the projections 244 in the opened position, as the initial movement of the walls 240, 242 may result in plastic deformation of the regions 246. That is, the walls 240, 242 may remain in the opened position once they are pushed outwardly away from the archwire slot 214.

Once the archwire is installed in the archwire slot 214, the bracket 210 may naturally warm to the temperature of the oral cavity, and in doing so, the regions 246 may recover their initial undeformed positions with the projections 244 over the archwire slot 214 in the closed position shown in FIG. 43A. It will be appreciated that the closing movement of the walls 240, 242 and corresponding projections 244 during movement to the closed position is spontaneous due to shape memory properties of the regions 246. Alternatively, the walls 240, 242 may be moved by the clinician back to the closed position.

In addition, in one embodiment, the untreated regions of the bracket body 212 may be relatively rigid as compared to, for example, the regions 246, in order to provide the desired torque control. For example, the surfaces of the archwire slot including the mesial and distal surfaces of the mesial and distal portions 231 and 233 may be of a base alloy composition that is more rigid than any of the regions 246. Further, it will also be appreciated that each of the regions 246 may differ from one another in alloy composition as well as being different from the base alloy composition. For example, one region 246 may exhibit shape memory properties while another region 246 may exhibit superelastic properties at the same temperature. The walls 240, 242 may therefore differ in their response to an applied force. For example, one wall 240 may move elastically between opened and closed positions due to a superelastic region 246 and the other wall 242 may be moved plastically to the opened position and then spontaneously move to the closed position due to shape memory upon heating. Accordingly, embodiments of the present invention are not limited to each region 246 having the same alloy composition.

Figure 45:
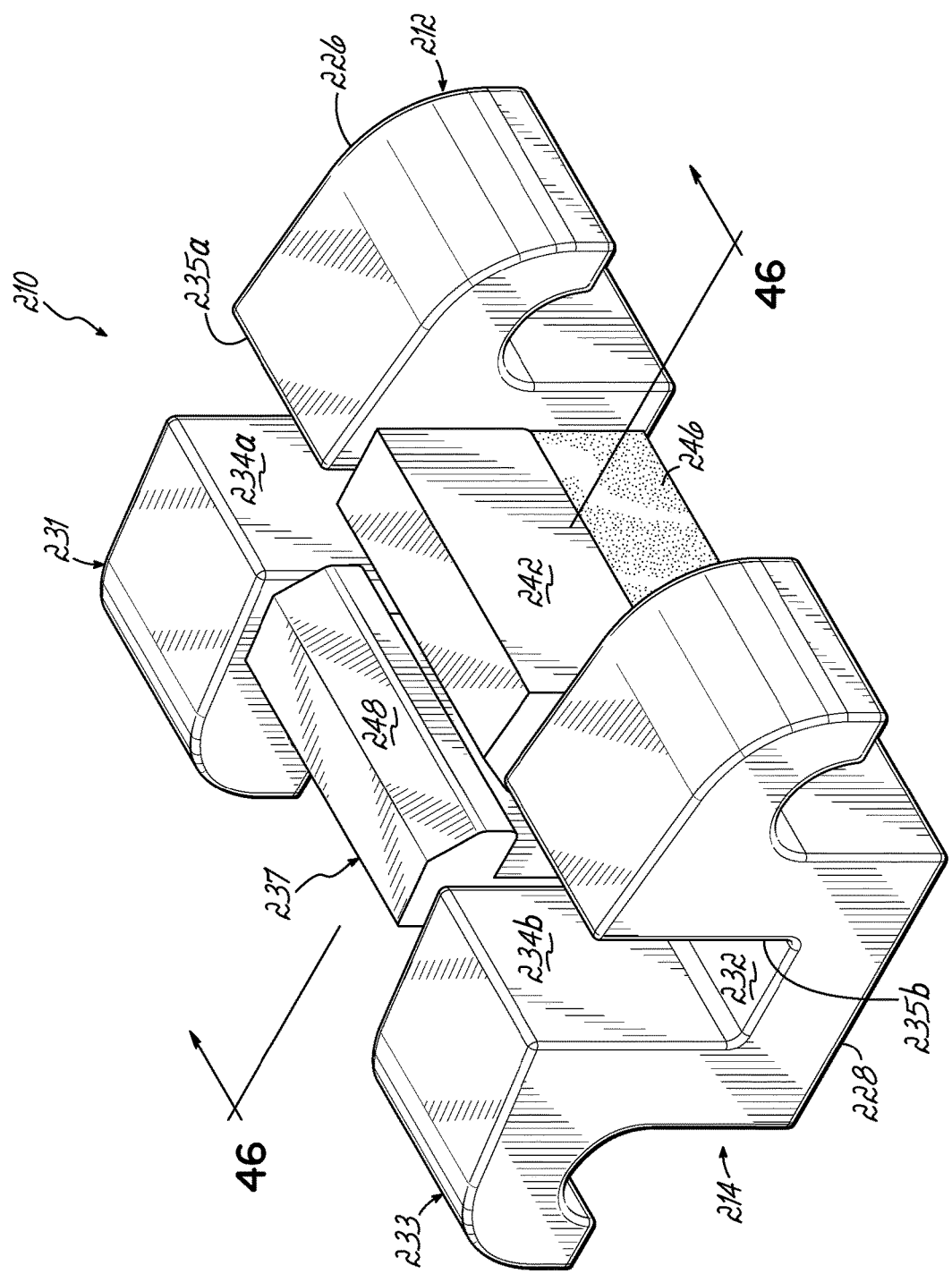
FIG. 45 is a perspective view of one embodiment of the orthodontic bracket according to the present invention.
Figure 46A:
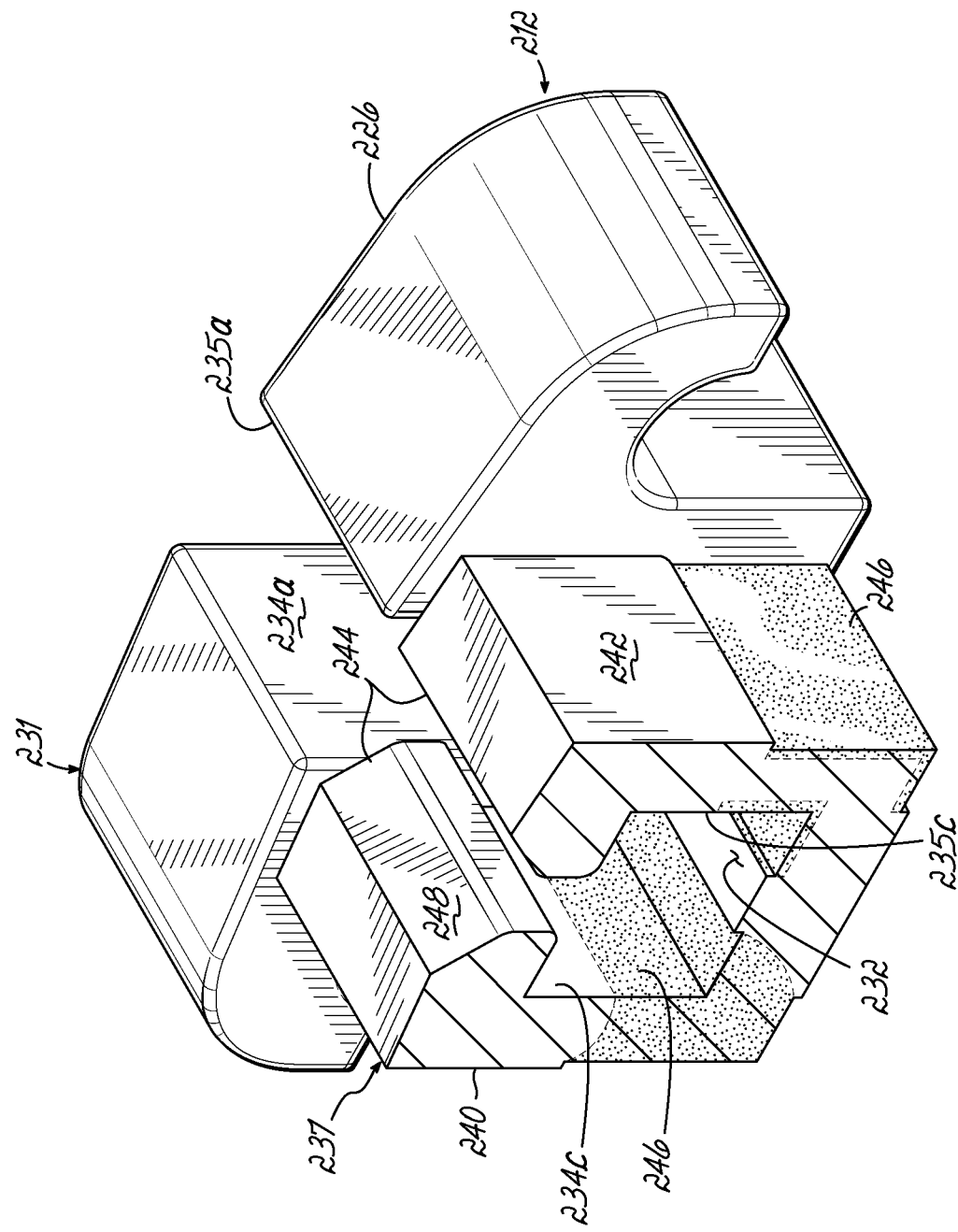
FIG. 46A is a cross-sectional view of the orthodontic bracket of FIG. 45 taken along section line 46A-46A depicting an integral ligating member in the closed position.
Figure 46B:
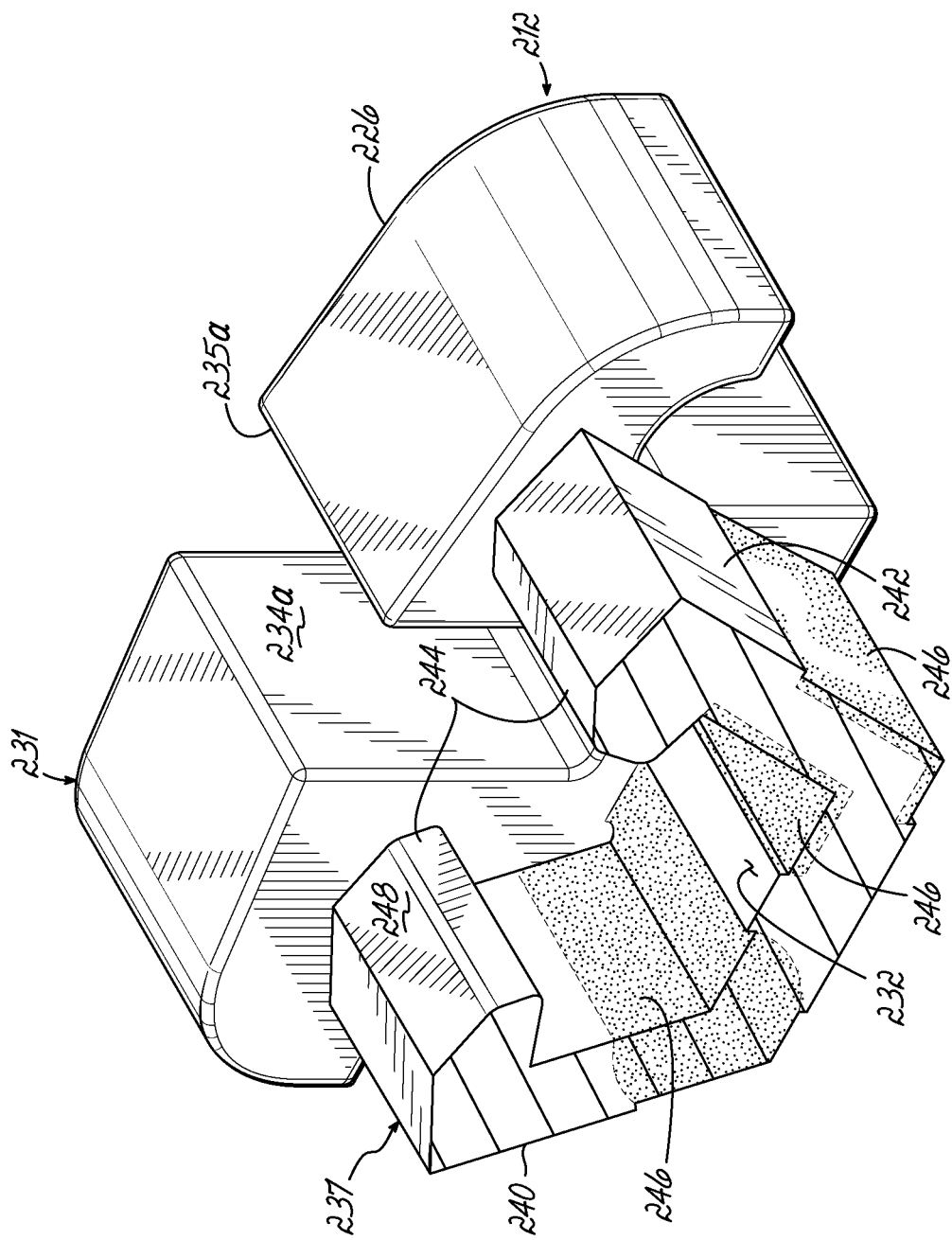
FIG. 46B is a cross-sectional view of the orthodontic bracket of FIG. 45 similar to FIG. 46A but depicting the integral ligating member in the opened position.

In one embodiment, and with reference now to FIGS. 45, 46A, and 46B, an alternative arrangement for integral ligating member or ligating portion 236 is shown with the central portion 237 having opposing shoulders or projections 244. Each of the projections 244 extends to less than one-half the distance of the width of the archwire slot 214 in an opposing, mirror-like relationship. The embodiment of the single-piece, self-ligating orthodontic bracket 210 shown in FIGS. 45, 46A, and 46B has regions 246 similar to that described above with regard to the embodiment shown in FIGS. 34-36. In this regard, the walls 240, 242 and opposing projections 244 have opened (FIG. 46B) and closed (FIG. 46A) positions such that the orthodontic bracket 210 is self-ligating and operates in a similar manner to that set out above with the regions 246 being of an alloy composition that is different from the base alloy composition so as to have superelastic or shape memory properties similar to the regions 246 set out above with regard to FIGS. 42-44.

Figure 47:
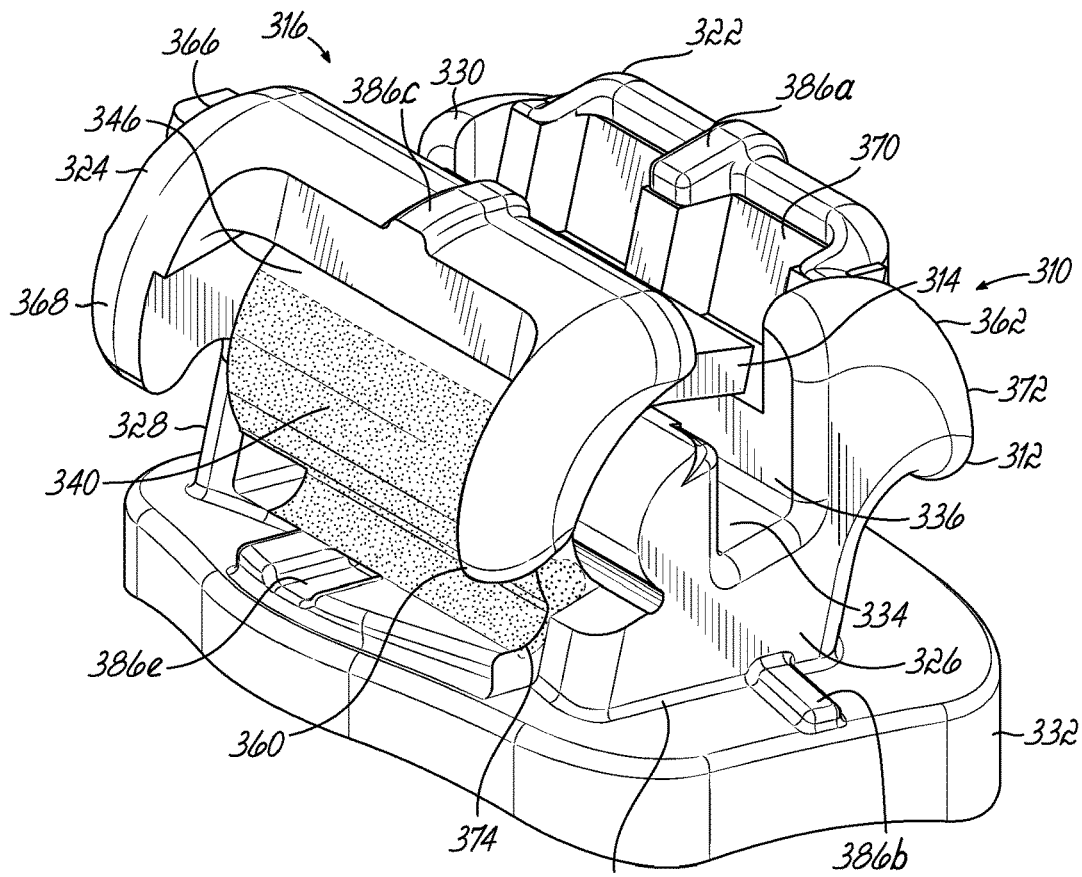
FIG. 47 is a perspective view of one embodiment of a self-ligating orthodontic bracket according to the present invention.
Figure 48:
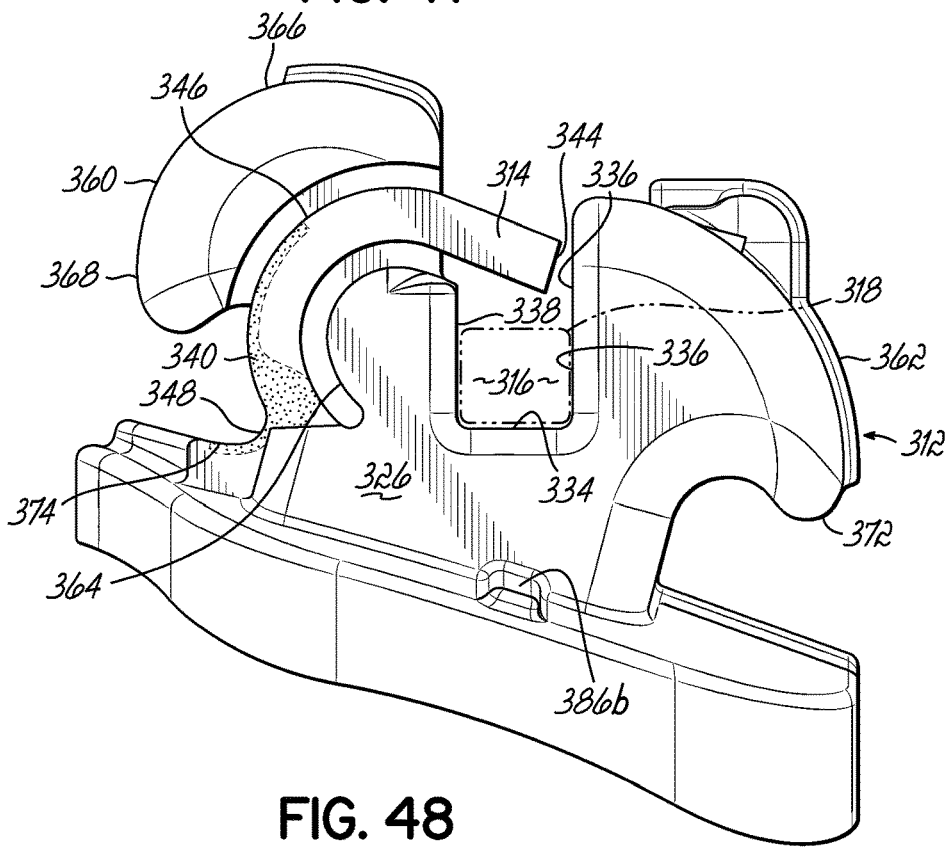
FIG. 48 is an elevation view of the self-ligating orthodontic bracket of FIG. 47.

Referring now to FIGS. 47 and 48 in another embodiment of the orthodontic appliance, a self-ligating orthodontic bracket 310 includes a bracket body 312 and an integral ligating member. In the exemplary embodiment shown, the integral ligating member is an integral ligating clip 314. Similar to embodiments of the orthodontic appliances above, the orthodontic bracket 310 is a single-piece, unitary body made of a SMA. The integral ligating member is not separately manufactured and then assembled with the bracket body 312. While portions of the ligating member are movable relative to the bracket body 312, the entire ligating member does not move relative to the bracket body 312 during insertion or removal of an archwire from the archwire slot. Rather, the bracket body 312 and the integral ligating member are, for example, cast together in a single casting process or are machined from a monolithic piece of SMA, for example, the bracket 310 may be made of a NiTi, CuNiTi, or other SMA alloy described above. Only a portion of the ligating member is movable relative to the bracket body. Similar to the embodiments of the orthodontic appliance described above, one or more selected regions of the bracket body 312 are treated with a form of energy, such as with a laser beam, to change the composition of the alloy in those selected regions. As is described below, the change in the alloy composition in the treated regions facilitates the self-ligating features of the bracket 310 and thus facilitates insertion and removal of an archwire from the bracket body 312 while preventing inadvertent removal of the archwire from the archwire slot 316 during orthodontic treatment.

To that end, with reference to FIGS. 47 and 48, the bracket body 312 includes an archwire slot 316 formed therein that is configured to receive an archwire 318 (FIG. 48) for applying corrective forces to the teeth. When mounted to the labial surface of a tooth carried on the patient's lower jaw, the bracket body 312 has a lingual side 320, an occlusal side 322, a gingival side 324, a mesial side 326, a distal side 328, and a labial side 330. The lingual side 320 of the bracket body 312 is configured to be secured to the tooth in any conventional manner, such as, by an appropriate orthodontic cement or adhesive or by a band around an adjacent tooth. The lingual side 320 may be provided with a pad 332 defining a bonding base that is secured to the surface of the tooth. The pad 332 may be coupled to the bracket body 312 as a separate piece or element, or alternatively, the pad 332 may be integrally formed with the bracket body 312.

In particular, the bracket body 312 includes a base surface 334 and a pair of opposed slot surfaces 336, 338 projecting labially from the base surface 334 that collectively define the archwire slot 316 extending in a mesial-distal direction from mesial side 326 to distal side 328. In one embodiment, the slot surfaces 336, 338 and base surface 334 are substantially integral within the material of the bracket body 312. However, it will be appreciated that one or more of the slot surfaces 334, 336, and 338 may be defined by an insert (not shown) or liner (not shown) to enhance the wear characteristics of the archwire slot 316 or for other reasons. The archwire slot 316 of the bracket body 312 may be designed to receive the orthodontic archwire 318 in any suitable manner.

With continued reference to FIG. 47, in one embodiment the bracket body 312 includes a gingival body portion 360 and an occlusal body portion 362 that are generally separated by the archwire slot 316. The gingival body portion 360 generally defines the slot surface 338. In particular, a shelf member 364 of the gingival body portion 360 may define the slot surface 338. The gingival body portion 360 may include a bridge member 366 that generally defines a labial surface of the bracket body 312. As shown best in FIG. 48, the integral clip 314 is formed in a space between the shelf member 364 and the bridge 366. In one embodiment, the gingival body portion 360 further defines a gingival tie wing 368 by which an archwire may be secured to the bracket body 312 with an elastomeric member (not shown) as is known in the art.

The occlusal body portion 362 generally defines the slot surface 336 and includes a tool recess 370 in which a clinician may place a tool to leverage against the integral clip 314. Similar to the gingival body portion 360, the occlusal body portion 362 may define the occlusal tie wing 372, as shown. Ligatures may be used in addition to or as an alternative to the clip 314 to secure the archwire to the bracket 310 via the occlusal tie wing 372. For example, where the clinician is unable to seat the archwire 318 within the slot 316 sufficiently to capture the archwire 318 with the clip 314 in the closed position, it may be necessary to use a ligature to secure the bracket body 312, via the tie wings 368, 372, to the archwire to move the tooth into a position where the archwire 318 may then be seated within the archwire slot 316. It will be appreciated that while tie wings 368, 372 and ligatures are described herein, embodiments of the present invention are not limited only to those brackets having tie wings.

In one embodiment shown in FIGS. 47 and 48, the bracket 310 includes one or more alignment markers 386a, 386b, 386c, 386d, 386e that may comprise raised or recessed areas on the surface to create a visibly discernable feature on the bracket 310. The alignment markers 386a-386e are more fully described in U.S. Pub. No. 2012/0058442, which is incorporated by reference herein in its entirety.

As described above, the ligating clip 314 is formed integrally with the bracket body 312. The integral ligating clip 314 is generally c-shaped and includes a labial portion 344 that extends over and opposes the base surface 334 of the archwire slot 316 and includes a gingival portion 346 and a lingual portion 348 at or near the area at which the clip 314 is integrally connected with the bracket body 312. As shown in FIG. 48, the labial portion 344 defines a labial boundary of the archwire slot 316 when the labial portion 344 of the integral clip 314 is in the closed position. The integral clip 314 may contact the bridge member 366 during flexing of the labial portion 344 of the clip 314, for example, when an archwire pulls labially on the labial portion 344 of the clip 314, which may cause the gingival portion 346 of the integral clip 314 to contact the bridge member 366. Contact between the integral clip 314 and the bridge member 366 may prevent the inadvertent release of the archwire 318 from the archwire slot 316. While the clip 314 is positioned to close the archwire slot 316 opposite the base surface 334 to prevent inadvertent removal of the archwire 18 therefrom during treatment, a portion of the integral clip 314 may be intentionally moved to an opened position to allow one archwire within the slot 316 to be removed and another archwire to be inserted as treatment progresses.

In one embodiment, a portion of the orthodontic bracket 310 is selectively treated with a form of energy, such as a laser beam, so that the surface portion includes a treated region 340 that differs in chemical composition from the base alloy composition of the SMA. As shown in FIGS. 47 and 48, portions of each of the integral clip 314 and bracket body 312 may include a treated region 340. In one embodiment, the lingual portion 348 at or near the intersection of the integral clip 314 with the body 312 and the gingival portion 346 of the integral clip 314 may be treated with a form of energy such that they include the treated region 340 having a different chemical composition than adjacent portions of the integral clip 314 and the bracket body 312. The treated region 340 may include the selected portions of the surface of the integral clip 314 and may extend into or through the thickness of the integral clip 314, as is shown in FIG. 48. The treated region 340 may extend into the body 312 at the intersection of the integral clip 314 and the body 312, as is indicated at location 374. Moreover, it will be understood that the difference in chemical composition between the treated region 340 and untreated regions will not occur at an exact point of delineation therebetween. Rather, the difference in chemical composition may occur gradually from the treated region 340 in any direction. This may be the case for any of the treated regions described herein. In addition, it will be appreciated that the entire integral clip 314 may be treated as set forth above such that the properties associated with the treated region 340 may apply to the integral clip 314 as a whole. The treated region 340 may impart either superelastic or shape memory characteristics to a portion of the clip 314.

Where superelastic qualities are imparted, the integral clip 314 may be physically moved (by a tool, for example) into the opened position so that the archwire may be directed into or removed from the archwire slot 316. Then, once the archwire is inserted or removed as desired, the clinician may release the clip 314 so that it may return to the closed position. Due to the superelastic properties of the treated regions 340, the ligating clip 314 may also be configured to actively ligate the archwire 18. As is known, active ligating of the archwire 318 by the integral clip 314 may depend on the size and shape of the archwire 318. Such active ligation may be provided, without the degradation in the force applied to the archwire as it would with stainless steel or other metallic members, due to the superelastic properties of the treated region 340 of the integral clip 314. Alternatively, the ligating clip 314 may be configured for passive ligation of the archwire 318.

The treated region 340 may also exhibit shape memory characteristics, similar to those discussed above with respect to the other embodiments of orthodontic appliances. In one embodiment, the integral clip 314 may transition between the opened and closed positions without a mechanical input. A change in temperature of the integral clip 314, specifically the treated region 340, may be sufficient for the integral clip 314 to spontaneously move from the opened position to the closed position. For example, the clinician may cool the integral clip 314 to a temperature whereby the composition of the treated region 340 includes a substantial proportion of martensite relative to austenite. This may occur by cooling the treated region 340 from the normal temperature of the oral cavity to a cooler temperature, such as below $A_f$, below $M_s$, or below $M_f$. In this embodiment, the clinician may use a cold-compress, compressed gas, or other method of reducing the temperature of the treated region 340 to a point at or below the normal temperature of the patient's oral cavity prior to deforming the integral clip 314. The clinician may then forcibly move the integral clip 314 to an opened position. This may include plastically deforming the integral clip 314 particularly in the treated region 340. Once deformed, the integral clip 314 may remain in the opened position while the temperature of the treated region 340 remains relatively cool as compared to the normal temperature of the oral cavity. The clinician may then remove and/or insert an archwire from the archwire slot 316. As the integral clip 314 is heated by the patient's body or by application of an external source of heat, the integral clip 314 may transition to the closed position. Alternatively, the clinician may plastically deform the integral clip 314 back to the closed position. In either case, once the treated region 340 reaches the normal oral cavity temperature, it may exhibit superelastic properties may provide active or passive ligation as set out above.

Figure 49:
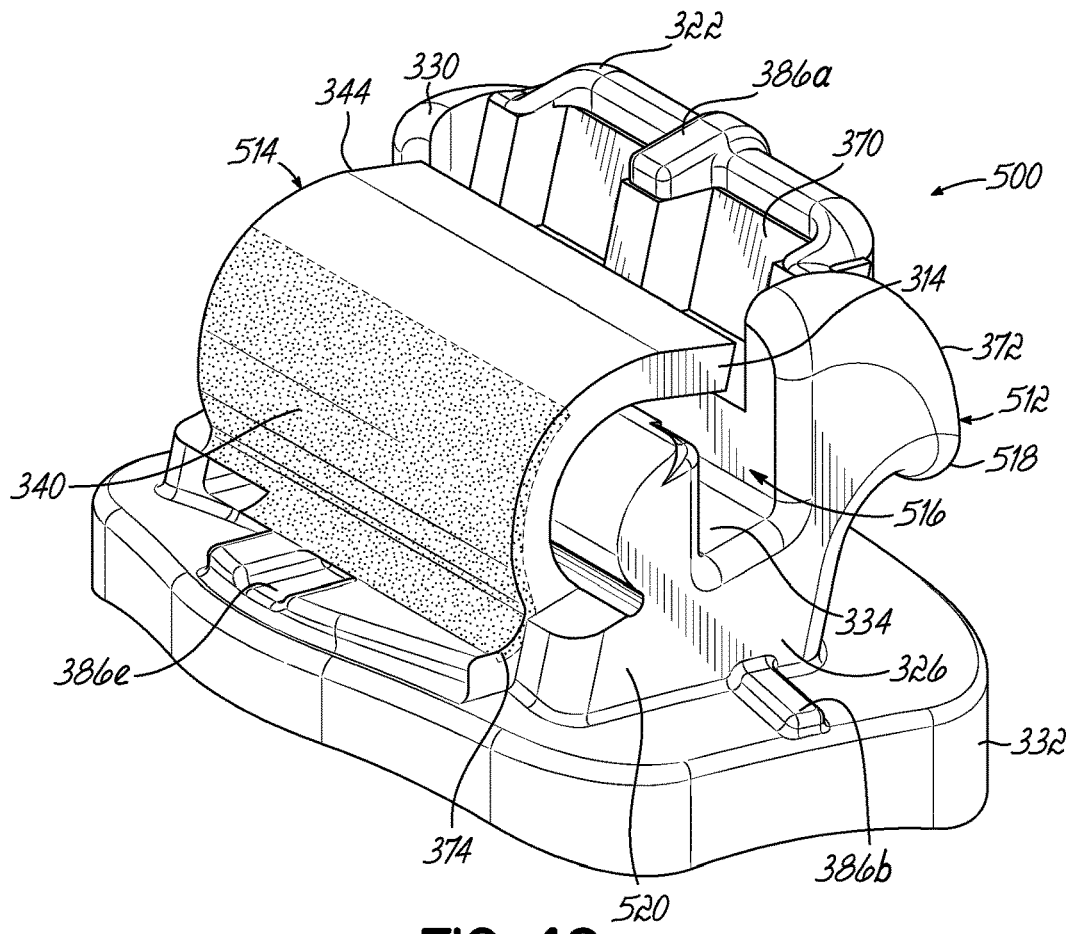
FIG. 49 is a perspective view of one embodiment of a self-ligating orthodontic bracket according to the present invention.
Figure 50:
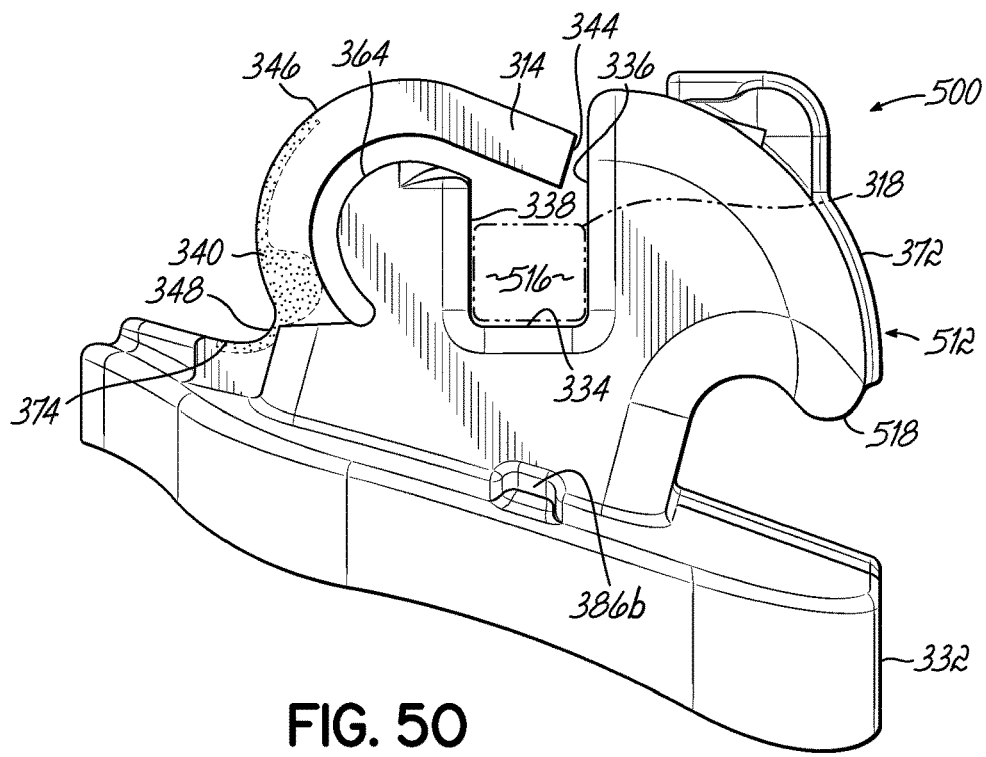
FIG. 50 is an elevation view of the self-ligating orthodontic bracket of FIG. 49.

Another embodiment of a self-ligating orthodontic bracket is shown in FIGS. 49 and 50, in which like reference numerals refer to like elements of FIGS. 47 and 48. A self-ligating orthodontic bracket 500 is similar to the orthodontic bracket 310 described with reference to FIGS. 47 and 48 and described above. The orthodontic bracket 500 includes a bracket body 512 and an integral ligating clip 514 in which the bracket 500 is a unitary piece of metal made of a SMA. That is, the bracket body 512 and the clip 514 are formed during the same formation process. For example, the bracket body 512 and the clip 514 may be machined from a solid piece of SMA, may be cast during a single casting process, or may be formed during a single formation process.

The bracket body 512 defines an archwire slot 516 that generally separates an occlusal body portion 518 from a gingival body portion 520. The bracket body 512 differs from the bracket body 312 of the orthodontic bracket 310 shown in FIGS. 47 and 48 by the absence of the bridge member 366. That is, the gingival body portion 520 lacks any structure that labially covers the integral clip 514 in the labial direction. The integral clip 514 is thus fully exposed along the labial-most surface of the bracket 500.

During ligation, the labial deflection of the integral clip 514, specifically the labial portion 344 of the clip 514, is not restricted in deflection in the labial direction by any portion of the bracket body 512. However, advantageously, the absence of the bridge member 366 or other structure over the integral clip 514 permits the clinician unrestricted access to moving the integral clip 514 when treatment requires the archwire be changed. Thus, the clinician may more easily operate the integral clip 514 whether by elastically holding the labial portion 344 of the clip 514 in an opened position or by plastically deforming the integral clip 514 to an opened position to insert and remove archwires from the archwire slot 516 as described above. As is set forth above, treated regions 340 of the integral clip 514 may facilitate treatment by providing superelastic and/or shape memory properties to at least portions of the integral clip 514.

Multi-Modulus Orthodontic Brackets

Orthodontic brackets are typically bonded to the teeth using adhesives. Commercial adhesives are limited in bond strength. During orthodontic treatment, impact and shearing forces on the orthodontic brackets can break the adhesive bond and thus disengage or dislodge the brackets from the teeth. When the adhesive bond fails, the patient must schedule an extra visit to the clinician's office to get the bracket rebonded or replaced. This is inconvenient for both the patient and the clinician. Furthermore, in the time it takes between the bond failure and the repair, the loose bracket does nothing to facilitate orthodontic treatment. Accordingly, this period of inefficacy can add to overall treatment time.

Figure 51:
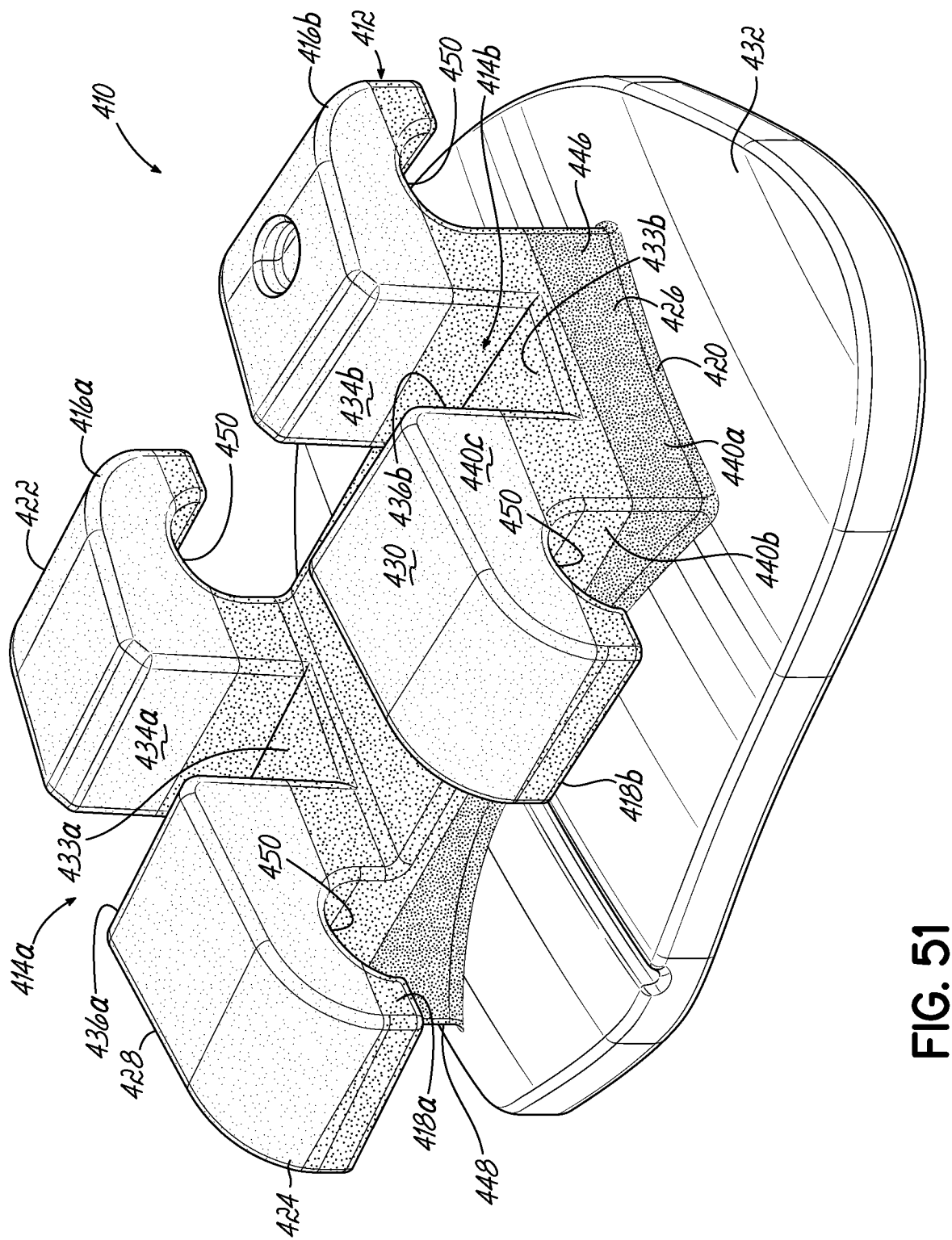
FIG. 51 is a perspective view of one embodiment of an orthodontic bracket according to the present invention depicting a layered-type arrangement of a plurality of treated regions.

To solve this and other problems related to adhesive bond failure, an embodiment of the invention includes features that absorb the energy of impact forces on the orthodontic appliance, reduces the transmittance of the magnitude of those forces to the bond, and thus decreases the likelihood of adhesive bond failure between an orthodontic appliance and the tooth. As shown in FIGS. 51-54, in one embodiment of the invention, an orthodontic bracket 410 includes a bracket body 412, which is shown as a unitary body made of a SMA having a base alloy composition. In the exemplary embodiment shown, the bracket body 412 is a twin tie-wing type orthodontic bracket. It will be appreciated, however, that embodiments of the present invention are not limited to twin tie-wing type orthodontic brackets. With reference to FIG. 51, the bracket body 412 defines an archwire slot 414a, 414b that is configured to receive an archwire (not shown) for applying corrective forces to a tooth. The bracket body 412 has pairs of opposing occlusal and gingival tie wings 416a, 416b, 418a, 418b, respectively, for receiving one or more ligatures (not shown), as is known in the art.

When mounted to the labial surface of a tooth carried on the patient's lower jaw, the bracket body 412 has a lingual side 420, an occlusal side 422, a gingival side 424, a mesial side 426, a distal side 428, and a labial side 430. The lingual side 420 of the bracket body 412 is configured to be secured to the tooth in any conventional manner, such as, by an appropriate orthodontic cement or adhesive or by a band around an adjacent tooth. The lingual side 420 may be provided with a pad 432 defining a bonding base that is secured to the surface of the tooth. The pad 432 may be coupled to the bracket body 412 as a separate piece or element or, alternatively, the pad 432 may be integrally formed with the bracket body 412. The pad 432 may be similar to or include similar features as the pad described in U.S. Patent Publication No. 2011/0189624, which is incorporated herein by reference, in its entirety.

The body 412 includes a base surface 433 and a plurality of opposed mesial and distal surfaces 434a, 434b, 436a, 436b projecting labially from the base surface 433 that collectively define the archwire slot 414a, 414b in the body 412. The archwire slot 414a, 414b extends in a mesial-distal direction from mesial side 426 to distal side 428 of the bracket body 412.

In exemplary embodiments shown in FIGS. 51-54, one or more portions of the bracket body 412 are selectively treated with a form of energy, such as a laser, in order to define a treated region or a plurality of treated regions which include properties that differ from the properties associated with the base alloy composition. In one embodiment, the treated regions exhibit differences in composition relative to one another and relative to the base alloy composition so that each has a different proportion of martensite and austenite at the temperature of the oral cavity. In this regard, in the treated regions the ratio of martensite to austenite may be varied so that an impact load causes less elastic recovery or complete plastic deformation in one or more of the treated regions. By selectively varying the ratio of martensite to austenite, the amount of energy absorbed by the corresponding phase transformation of that treated region may be varied. Accordingly, an impact load on the bracket body 412 may cause phase transformation of one treated region but not another treated region. The phase transformation is used to absorb the shock or sudden stress of the impact. In this manner, the treated regions are configured to undergo variable phase transformation when subject to an impact so that the bracket body 412 absorbs some or all of the impact energy. Advantageously, due to the superelastic qualities of the treated regions, the bracket body 412 absorbs the impact energy and then returns to its original position such that the impact energy is not entirely transferred to the adhesive bond between the bracket 410 and the tooth.

With reference specifically to the embodiment shown in FIG. 51, the bracket body 412 may have a plurality of treated regions, each with a varying amount of treatment. Generally, the variation is graded throughout the bracket body 412 by treating the bracket body 412 in layers. Specifically, the varied amount of treatment in any of the embodiments may be accomplished by treating each individual region with a varied amount (i.e., intensity) of energy, or for a longer or shorter time than other treated regions. As described above, a laser beam may be used to selectively treat various portions of the bracket body 412 to change the chemical composition of the SMA in those regions.

Specifically, in one embodiment, the bracket body 412 shown in FIG. 43 includes three different treated regions 440a, 440b, 440c. Generally, each of the treated regions 440a, 440b, 440c is provided in a layered configuration with the layers being stacked in the generally lingual-labial direction. By way of example only, the treated region 440c may undergo phase transformation before either of regions 440b or 440a. Thus, an impact on the bracket body 412 in the labial-most portions of the bracket body 412 will be at least partially absorbed by the phase transformation in the region 440c. Any impact energy not absorbed in the region 440c may cause phase transformation in region 440b. Similarly, any impact energy not absorbed in region 440b may be absorbed by the phase transformation in region 440a. Ultimately, absorbing the energy by phase transformation from the outer-most regions to the inner-most regions reduces the impact energy transferred to the adhesive bond and thus reduces the likelihood that the bracket 412 is inadvertently debonded from the tooth during orthodontic treatment.

In particular, in one embodiment, the first treated region 440a is positioned beginning at the lingual point of the body 412 adjacent the pad 432. The first treated region 440a extends therefrom to a plane spaced in the lingual direction from the archwire slot 414a, 414b. The second treated region 440b is adjacent the first treated region 440a and extends labially from the first treated region 440a. Part of the second treated region 440b is located along the base surface 433a, 433b and the occlusal and gingival surfaces 434a, 434b, 436a, 436b of the archwire slot 414a, 414b. Part of the second treated region 440b is also located on or at an arch-shaped region 450 of tie wings 416a, 416b, 418a, 418b. The third treated region 440c is adjacent the second treated region 440b and extends labially from the second treated region 440b to the labial side 430 of the bracket body 412.

More specifically, the third treated region 440c essentially begins at or near the arch-shaped region 450 of tie wings 416, 418, and extends labially therefrom to the labial surfaces 452 of the bracket body 412 and tie wings 416a, 416b, 418a, 418b. Part of the third treated region 440c is also located at the mesial and distal end faces 446, 448, as well as the mesial and distal surfaces 434, 436 of the archwire slot 414.

Each of the treated regions 440a, 440b, 440c may correspond to a change in the base alloy composition. As set forth above, specifically with respect to the archwires, each of the treated regions 440a, 440b, 440c may exhibit a difference in phase composition between austenite and martensite at the temperature of the oral cavity. The stress-strain relationship in each region therefore behaves differently under impact loading. The layered-type bracket body 412 shown in FIG. 51 may absorb impact energy and thus may reduce the likelihood that the adhesive bond between the bracket body 412 and the tooth experiences a stress sufficient to break the adhesive bond.

Figure 52:
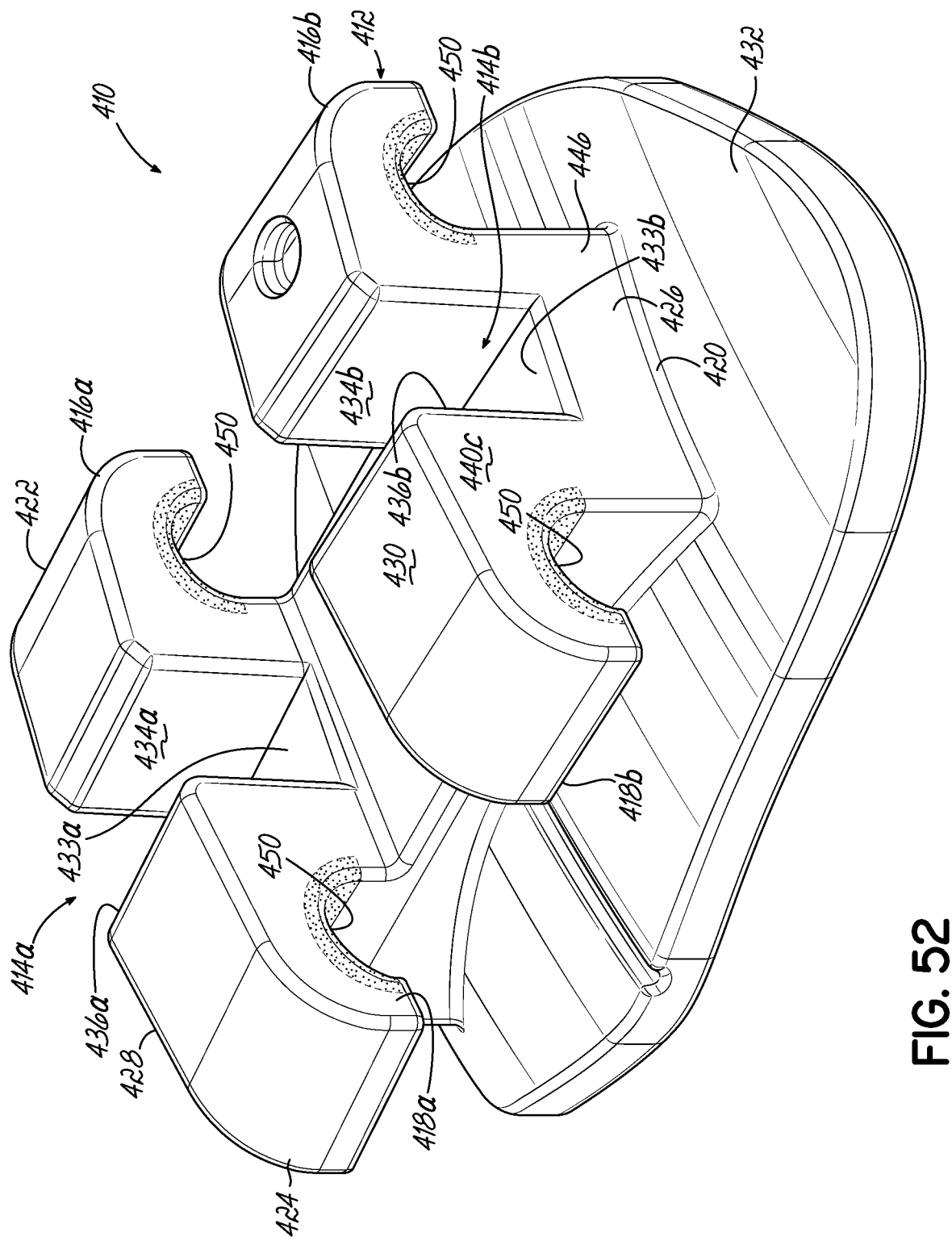
FIG. 52 is a perspective view of one embodiment of an orthodontic bracket according to the present invention depicting a different arrangement of a plurality of treated regions compared to the orthodontic bracket of FIG. 51.
Figure 53:
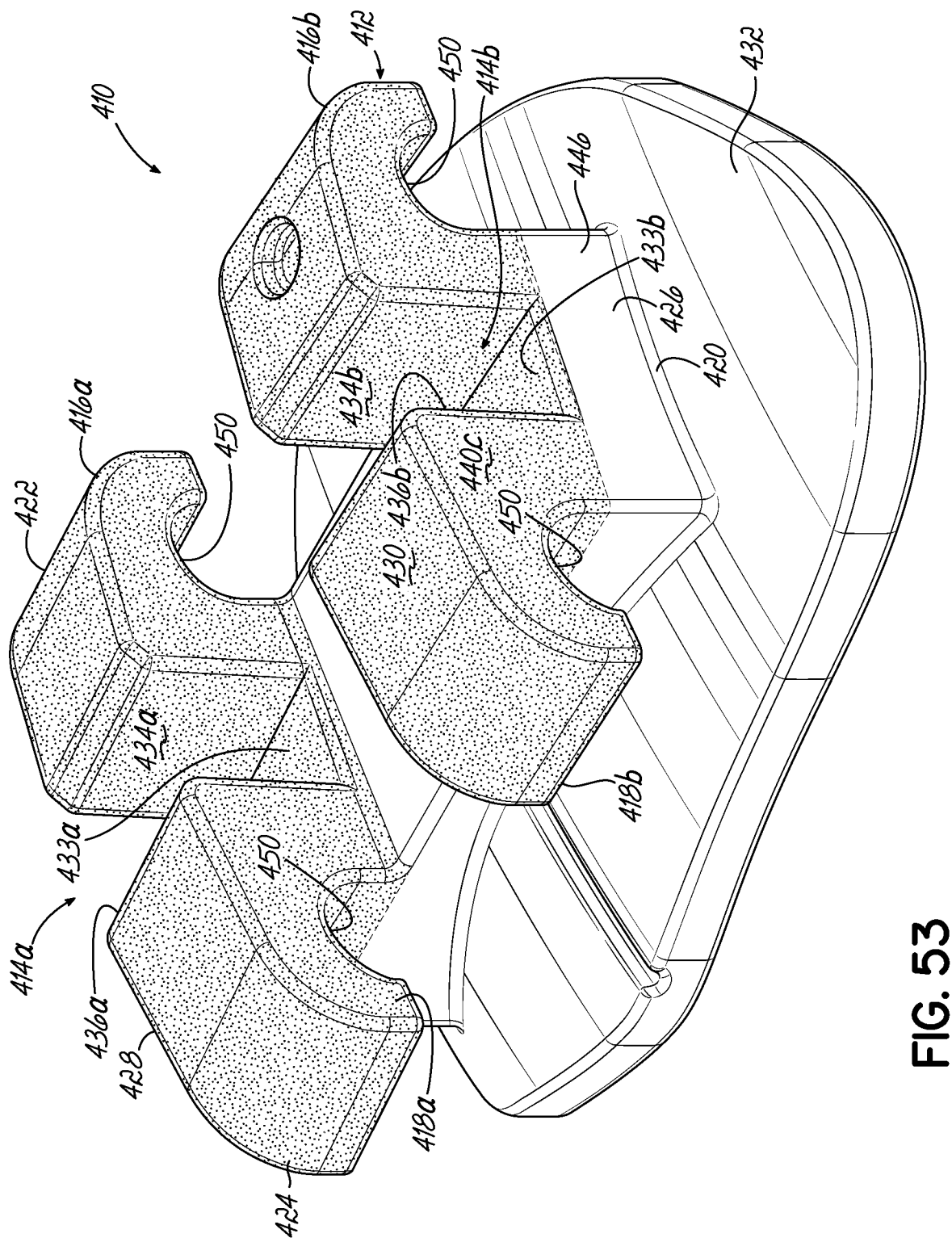
FIG. 53 is a perspective view of one embodiment of an orthodontic bracket according to the present invention depicting a different arrangement of a plurality of treated regions compared to the orthodontic brackets of FIGS. 51 and 52.
Figure 54:
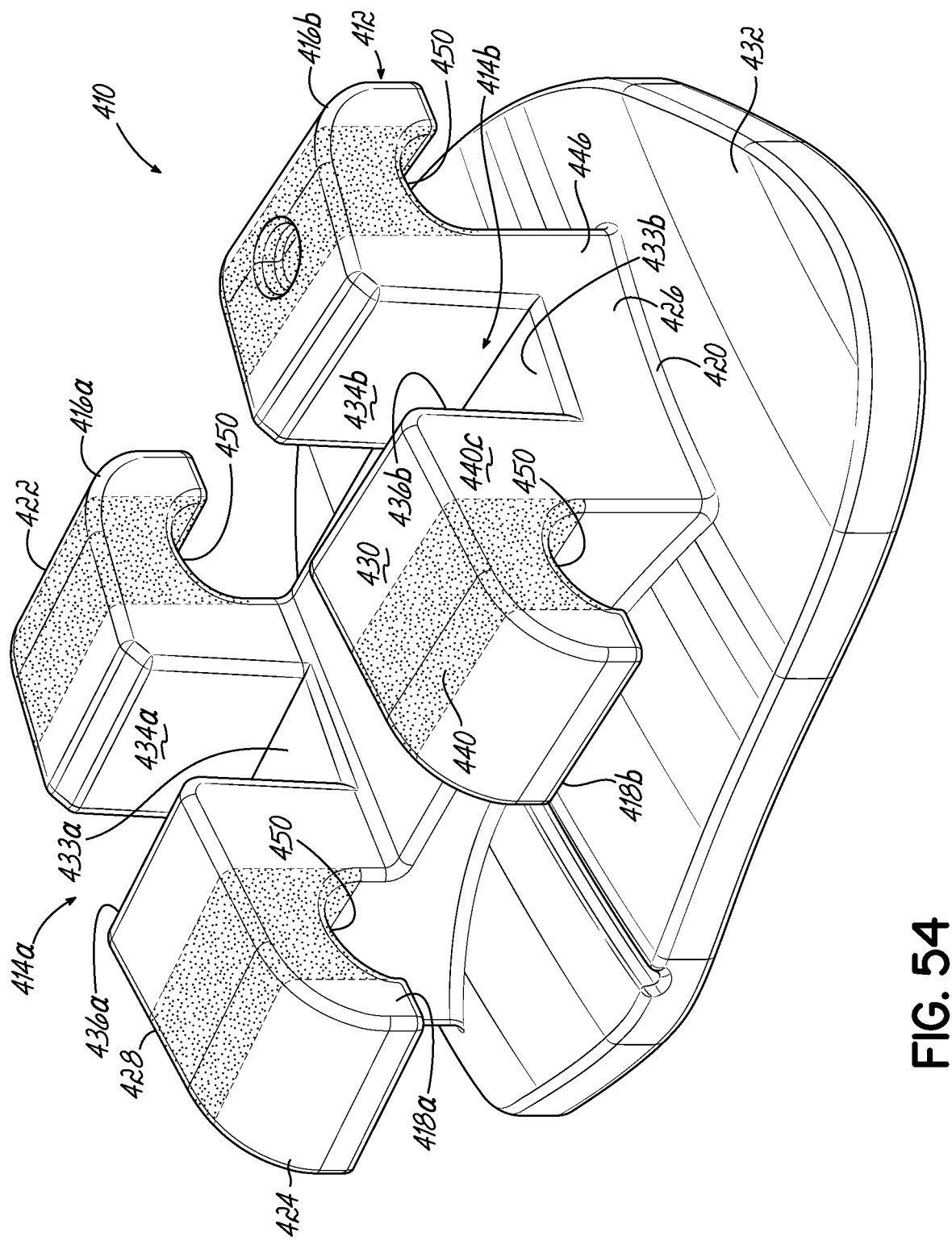
FIG. 54 is a perspective view of one embodiment of an orthodontic bracket according the present invention depicting a different arrangement of a plurality of treated regions compared to the orthodontic brackets of FIGS. 51-53.

It will be appreciated that embodiments of the invention are not limited to the layered bracket depicted in FIG. 51. Treatment of a bracket body with a beam of energy, such as a laser beam, allows any number of configurations of treated and untreated regions to be produced. By way of example, and not limitation, with reference now to FIGS. 52-54, in which like reference numerals refer to like features of FIG. 51, the orthodontic bracket 410 may include a treated region 440 at each of the arch-shaped regions 450 of the tie wings 416a, 416b, 418a, 418b, as is shown in FIGS. 52 and 54. By way of additional example and with reference to FIG. 53, in another embodiment, the treated region 440 may include the base surface 433 of the archwire slot 414a, 414b. The treated region 440 extends to and includes each of the tie wings 416a, 416b, 418a, 418b. As with other embodiments, it will be appreciated that, while the treated regions 440 may be described as included in, on, or at a surface portion, the treated region 440 may extend beyond the surface and into the body a certain depth. Moreover, it will be understood that the difference in chemical composition between different treated regions 440 or between treated and untreated regions will not occur at an exact point of delineation therebetween. Rather, the difference in chemical composition may gradually occur and will be visible with known methods, such as microscopy.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. By way of example, while the embodiments described herein show treated regions having a difference in alloy composition relative to an initial base alloy composition so that a single metallic orthodontic appliance may have multiple regions of differing mechanical and/or chemical properties. Further, each of these regions may cooperate to facilitate orthodontic treatment. The various features of the invention may be used alone or in any combination depending on the needs and preferences of the user.

What is claimed is:

1. An orthodontic archwire having a length as measured from a first end to a second end and defining a central axis comprising:
a unitary piece of a shape memory alloy extending from the first end to the second end including a first lengthwise zone having a base alloy composition of at least two different metallic elements in a first ratio through the cross section of the archwire and a second lengthwise zone positioned adjacent along the central axis of the archwire from the first lengthwise zone and including a region having an alloy composition in which only the metallic elements of the base alloy composition are present and the different metallic elements are in a second ratio that is different from the first ratio, wherein the second ratio extends through the cross section of the archwire and wherein the base alloy composition has a first austenitic finish temperature and the region has an austenitic finish temperature that is greater than the first austenitic finish temperature.

2. The orthodontic archwire of claim 1 wherein the shape memory alloy is a nickel titanium alloy (NiTi) and the alloy composition of the region has less nickel than the base alloy composition.

3. The orthodontic archwire of claim 1 wherein the shape memory alloy is a copper chromium nickel titanium alloy (CuCrNiTi) and the alloy composition of the region has less nickel and/or less titanium than the base alloy composition.

4. The orthodontic archwire of claim 1 wherein the shape memory alloy is a copper aluminum nickel alloy (CuAlNi) and the alloy composition of the region has less copper than the base alloy composition.

5. The orthodontic archwire of claim 1 wherein the shape memory alloy is a copper aluminum nickel alloy (CuAlNi) and the alloy composition of the region has less aluminum than the base alloy composition.

6. The orthodontic archwire of claim 1 wherein the shape memory alloy is a nickel titanium (NiTi) alloy in which the second ratio of nickel to titanium is less than the first ratio of nickel to titanium.

7. The orthodontic archwire of claim 1 wherein the shape memory alloy is a copper aluminum nickel (CuAlNi) alloy in which the second ratio of nickel to aluminum and/or copper to aluminum is less than the first ratio of nickel to aluminum and/or copper to aluminum, respectively.

8. The orthodontic archwire of claim 1 wherein the archwire has a uniform cross-section from the first end to the second end.

9. The orthodontic archwire of claim 1 wherein the region of the second lengthwise zone has a coefficient of friction when in contact with the orthodontic bracket that is less than the coefficient of friction between the first lengthwise zone and the orthodontic bracket.

10. The orthodontic archwire of claim 1 wherein one of the first lengthwise zone and the second lengthwise zone is a single crystal alloy and the other of the first lengthwise zone and the second lengthwise zone is a polycrystalline alloy.

11. The orthodontic archwire of claim 1 wherein the archwire produces a force distribution on the patient's corresponding teeth in which a force at a 1-3 location is greater than a force at a 1-1 location and is less than a force at a 1-5 location, and the force at the 1-3 location is at least 1.5 N.

12. The orthodontic archwire of claim 11 wherein, during orthodontic treatment, the first lengthwise zone overlaps at least one of the 1-5 location and the 1-3 location and the second lengthwise zone overlaps at the 1-1 location.

13. The orthodontic archwire of claim 11 wherein, during orthodontic treatment, the force at the 1-3 location is equidistant between the force at the 1-1 location and the force at the 1-5 location.

14. The orthodontic archwire of claim 11 wherein, during orthodontic treatment, the archwire produces a difference of more than 0.5 N of force between the force at the 1-1 location and the force at the 1-3 location.

15. The orthodontic archwire of claim 11 wherein, during orthodontic treatment, the archwire produces a difference of at least 1 N of force between the 1-1 location and the 1-3 location.

16. An archwire for use in orthodontic treatment of a tooth malocclusion in a mouth of an individual comprising: a wire having a length as measured from a first end to a second end and defining a central axis comprising: a unitary piece of a shape memory alloy extending from the first end to the second end including a first lengthwise zone having a base alloy composition of at least two different metallic elements in a first ratio through the cross section of the archwire and a second lengthwise zone positioned adjacent along the central axis of the archwire from the first lengthwise zone and including a region having an alloy composition in which only the metallic elements of the base alloy composition are present and the different metallic elements are in a second ratio that is different from the first ratio, wherein the second ratio extends through the cross section of the archwire and, wherein the base alloy composition and region have different austenitic finish temperatures, wherein when the wire is installed in a lower jaw of the individual, the wire applies forces to teeth of the lower jaw of the individual comprising about 0.77N to an L1 and L2 tooth, about 0.81 N to an L3 tooth, about 1.06N to an L4 tooth, about 0.96N to an L5 tooth and about 1.9N to an L6 tooth.

17. An orthodontic archwire for use with a plurality of orthodontic brackets to apply forces to a patient's tooth, the archwire having a length as measured from a first end to a second end and defining a central axis comprising: a unitary piece of a copper aluminum nickel (CuAlNi) shape memory alloy extending from the first end to the second end including a first lengthwise zone having a base alloy composition of copper, aluminum, and nickel in respective first ratios through the cross section of the archwire and a second lengthwise zone positioned adjacent along the central axis of the archwire from the first lengthwise zone and including a region having an alloy composition of only copper, aluminum, and nickel in respective second ratios, at least one of the second ratios is different from the respective first ratios, wherein the second ratios extend through the cross section of the archwire and, wherein the base alloy composition has a first austenitic finish temperature, the region has an austenitic finish temperature that is less than the first austenitic finish temperature, and the base alloy composition is in the form of a single crystal and the region is polycrystalline.

* * * * *